(12) United States Patent
Cau et al.

(10) Patent No.: US 9,545,412 B2
(45) Date of Patent: Jan. 17, 2017

(54) COMPOSITION AND METHODS USED DURING ANTI-HIV TREATMENT

(71) Applicant: UNIVERSITE D'AIX-MARSEILLE, Marseilles (FR)

(72) Inventors: Pierre Cau, Puyricard (FR); Nicolas Levy, Marseilles (FR)

(73) Assignee: UNIVERSITE D'AIX-MARSEILLE, Marseille (FR)

( * ) Notice: Subject to any disclaimer, the term of this patent is extended or adjusted under 35 U.S.C. 154(b) by 0 days.

(21) Appl. No.: 14/733,725

(22) Filed: Jun. 8, 2015

(65) Prior Publication Data

US 2015/0342970 A1  Dec. 3, 2015

Related U.S. Application Data

(63) Continuation of application No. 12/811,474, filed as application No. PCT/FR2008/001844 on Dec. 31, 2008, now abandoned.

(Continued)

(51) Int. Cl.
*A01N 37/36* (2006.01)
*A61K 31/66* (2006.01)
(Continued)

(52) U.S. Cl.
CPC ........... *A61K 31/675* (2013.01); *A61K 31/215* (2013.01); *A61K 31/22* (2013.01); *A61K 45/06* (2013.01);
(Continued)

(58) Field of Classification Search
CPC .. A61K 31/675; A61K 31/66; A61K 31/4025; A61K 31/366; A61K 31/22; A61K 31/427; A61K 31/665
(Continued)

(56) References Cited

U.S. PATENT DOCUMENTS 5,652,227 A   7/1997 Teronen et al.
5,733,558 A   3/1998 Breton et al.
(Continued)

FOREIGN PATENT DOCUMENTS

EP   1 127 573 A1   8/2001
EP   1 566 177 A1   8/2005
(Continued)

OTHER PUBLICATIONS

Martinez et al. "Management of dyslipidaemia in HIV-infected patients receiving antiretroviral therapy," Antiviral Therapy, 2004, vol. 9, pp. 649-663.*
(Continued)

*Primary Examiner* — Shengjun Wang
(74) *Attorney, Agent, or Firm* — Arent Fox LLP

(57) ABSTRACT

This invention relates to a composition comprising an anti-HIV treatment and a treatment for side effects of said anti-HIV treatment in an HIV-infected patient. This invention is, for example, very useful in the treatment of side effects caused by certain anti-HIV treatments, for example premature aging and lipodystrophy, which can be caused by protease inhibitors or reverse transcriptase inhibitors. The composition of this invention includes at least one hydroxymethylglutaryl-coenzyme A (HMG-CoA) reductase inhibitor, at least one farnesyl-pyrophosphate synthase inhibitor, and at least one anti-HIV agent. One of the processes for treating an HIV-infected patient includes, in any order, the following steps: (i) administration of a mixture including at least one hydroxymethylglutaryl-coenzyme A (HMG-CoA) reductase inhibitor and at least one farnesyl-pyrophosphate synthase inhibitor and (ii) administration of an anti-HIV agent, in which the administrations are concomitant, successive or alternative.

15 Claims, 16 Drawing Sheets

Related U.S. Application Data

(60) Provisional application No. 61/018,688, filed on Jan. 3, 2008.

(51) Int. Cl.

| | | |
|---|---|---|
| *A61K 31/675* | (2006.01) | |
| *A61K 31/497* | (2006.01) | |
| *C07D 239/42* | (2006.01) | |
| *A61K 31/505* | (2006.01) | |
| *A61K 31/44* | (2006.01) | |
| *A61K 31/425* | (2006.01) | |
| *A61K 31/34* | (2006.01) | |
| *A61K 31/215* | (2006.01) | |
| *A61K 31/22* | (2006.01) | |
| *A61K 45/06* | (2006.01) | |
| *A61K 31/427* | (2006.01) | |
| *A61K 31/496* | (2006.01) | |
| *A61K 31/366* | (2006.01) | |
| *A61K 31/4025* | (2006.01) | |
| *A61K 31/665* | (2006.01) | |

(52) U.S. Cl.
CPC .......... *A61K 31/366* (2013.01); *A61K 31/4025* (2013.01); *A61K 31/427* (2013.01); *A61K 31/496* (2013.01); *A61K 31/66* (2013.01); *A61K 31/665* (2013.01)

(58) Field of Classification Search
USPC .......................... 514/163, 94, 75, 274, 423
See application file for complete search history.

(56) References Cited

U.S. PATENT DOCUMENTS

| 5,902,805 | A | 5/1999 | Breton et al. | |
|---|---|---|---|---|
| 8,518,914 | B2* | 8/2013 | Levy ...................... | A61K 31/22 514/108 |
| 9,072,757 | B2* | 7/2015 | Levy ...................... | A61K 31/22 |
| 2001/0036936 | A1 | 11/2001 | Day et al. | |
| 2003/0105121 | A1 | 6/2003 | Bihari | |
| 2005/0020517 | A1 | 1/2005 | Drees et al. | |
| 2006/0078531 | A1 | 4/2006 | Sota | |
| 2006/0275294 | A1 | 12/2006 | Omoigui | |
| 2010/0120720 | A1 | 5/2010 | Levy et al. | |

FOREIGN PATENT DOCUMENTS

| WO | WO 02/00168 A2 | 1/2002 |
|---|---|---|
| WO | WO 2004/024165 A1 | 3/2004 |
| WO | WO 2004/050077 A1 | 6/2004 |
| WO | WO 2005/021001 A1 | 3/2005 |
| WO | WO 2005/074916 * | 8/2005 |
| WO | WO 2005/074916 A1 | 8/2005 |
| WO | WO 2009/112653 A2 | 9/2009 |

OTHER PUBLICATIONS

Kravcik "Update on HIV lipodystrophy," HIV Clin. Trials, 2004, vol. 5, No. 3, pp. 152-167.*
Brown et al. "Osteopenia and Osteoporosis in Patient with HIV: a review of current concepts," Current Infectious Disease Reports, Mar. 2006, vol. 8, No. 2, pp. 162-170.*
Gordon, et al., "Reduced Adiponectin and HDL Cholesterol without Elevated C-Reactive Protein: Clues to the Biology of Premature Atherosclerosis in Hutchinson-Gilford Progeria Syndrome", *J. Pediatrics*, 2005, 146(3): 336-341.
Fong, et al., "A Protein Farnesyltransferase Inhibitor Ameliorates Disease in a Mouse Model of Progeria", *Science*, 2006, 311: 1621-1623.
Toth, et al., "Blocking Protein Farnesyltransferase Improves Nuclear Shape in Fibroblasts from Humans with Progeroid Syndromes", *PNAS*, 2005, 102(36): 12873-12878.
van Beek, et al., "Farnesyl Pyrophosphate Synthase is the Molecular Target of Nitrogen-Containing Bisphosphonates", *Biochemical and Biophysical Research Communications*, 1999, 264, 108-111.
Leslie B. Gordon , et al., Clinical Trial of a Farnesyltransferase Inhibitor in Children with Hutchinson-Gilford Progeria Syndrome, Oct. 9, 2012, vol. 109, No. 41, pp. 16666-16671, *PNAS*.
U.S. Appl. No. 12/811,622, filed Mar. 16, 2011.
Merideth, M.A., et al. "Phenotype and course of Hutchinson-Gilford progeria syndrome", *N. Engl. J. Med.*, 358: 592-604 (2008).
Gerhard-Herman, M., et al. "Mechanisms of premature vascular aging in children with Hutchinson-Gilford progeria syndrome", *Hypertension* 59: 92-97 (2012) (with online supplement pp. 1-5).
Ali, K. Mandy, et al., "Cardiovascular disease risk reduction by raising HDL cholesterol-current therapies and future opportunities", *Br. J. Pharmacol.* 167: 1177-1194 (2012).
Wright, R.S. "Recent clinical trials evaluating benefit of drug therapy for modification of HDL cholesterol," *Curr. Opin. Cardiol.* 28: 389-398 (2013).
Olive, M., et al. "Cardiovascular pathology in Hutchinson-Gilford progeria; correlation with the vascular pathology of aging", *Arterioscler Thromb. Vasc. Biol.*, 30: 2301-2309 (2010) (supplemental material—17 pages).
Gu, W., et al., "A highly potent and selective farnesyltransferase inhibitor ABT-100 in preclinical studies", *Anticancer Drugs*, 16(10): 1059-1069 (2005).
O'Gorman, D.S., et al., "Considering statins for cholesterol-reduction in children if lifestyle and diet changes do not improve their health; a review of the risks and benefits", *Vasc. Health Risk Manag.* 7: 1-14 (2011).
ClinicalTrial.gov, for NCT00425607, "Phase II Trial of Lonafarnib (A Farnesyltransferase Inhibitor) for Progeria", Last update: Dec. 24, 2007, pp. 1-4.
ClinicalTrial.gov, for NCT00731016, "Treatment of the Hutchinson-Gilford Progeria syndrome With a Combination of Pravastatin and Zoledronic Acid", Last update: Jul. 4, 2013, pp. 1-3.
ClinicalTrial.gov, for NCT00916747, "Study of Zoledronic Acid, Pravastatin, and Lonafarnib for Patients With Progeria", Last Update: Aug. 1, 2012, pp. 1-3.
Bénédicte Cantecor, et al., "Anti-Aging Efficacy of a New Alendronate-Pravastatin Cosmetic Combination: A Randomized Double Blind Comparative Study", *Journal of Cosmetics, Dermatological Sciences and Applications*, Sep. 2013, 3, 163-71.
Mallon, Patrick, et al., "Effect of pravastatin on body composition and markers of cardiovascular disease in HIV-infected men—a randomized, placebo-controlled study", *AIDS* (London, Eng), vol. 20, No. 7, Apr. 24, 2006, pp. 1003-1010.
Brown, Todd, "Selected Endocrine Topics in HIV; Osteoporosis and Adrenal Insufficiency", *The PRN Notebook* [online], vol. 12, Dec. 2007, pp. 1-9.
Baulch-Brown, et al., "Inhibitors of the mevalonate pathway as potential therapeutic agents in multiple myeloma", *Leukemia Research*, New York, NY, US, vol. 31, No. 3, Jan. 12, 2007, pp. 341-352.
Varela, Ignacio, "Combined treatment with statins and aminobisphosphonates extends longevity in a mouse model of human premature aging", *Nature Medicine*, Jul. 2008, No. 7, pp. 767-772.
Dayle McClintock, et al., "The Mutant Form of Lamin A that causes Hutchinson Gilford Progeria is a Biomarker of Cellular Aging in Human Skin", *PLoS ONE*, Dec. 2007, Issue 12, e1269, pp. 1-10.
Samuel Varghese, et al., "Alendronate Stimulates Collagenase 3 Expression in Osteoblasts by Posttranscriptional Mechanisms", *Journal of Bone and Mineral Research*, 15(12): 2345-2351.
H. Valleala, et al., "Regulation of MMP-9 (gelatinase B) in activated Human Monocyte/Macrophages by Two Different Types of Bisphosphonates", *Life Sciences*, 73: 2413-2420 (2003).
Basso, et al., "Farnesyl Transferase Inhibitors", *Journal of Lipid Research*, 2006, pp. 15-31, vol. 47.
Biamonti, et al., "The Gene for a Novel Human Lamin Maps at a Highly Transcribed Locus of Chromosome 19 which Replicates at the Onset of S-phase", *Molecular and Cellular Biology*,1992, pp. 3499-3506, vol. 12.

(56) References Cited

OTHER PUBLICATIONS

Bishop, et al., "Farnesyl Transferase Inhibitors: Mechanism of Action, Translational Studies and Clinical Evaluation", *Cancer Biology and Therapy*, 2003, pp. S96-S104, vol. 2, Issue 4.
Broers, et al., "Laminopathies", *Journal of Pathology*, 2004, pp. 478-488, vol. 204.
Broers, et al., "Nuclear Lamins: Laminopathies and their Role in Premature Ageing", *Physical Review*, 2006, pp. 967-1008, vol. 86.
Capell, et al., "Inhibiting Farnesylation of Progerin Prevents the Characteristic Nuclear Blebbing of Hutchinson-Gilford Progeria Syndrome", *Proceedings of the National Academy of Sciences*, USA, 2005, pp. 12879-12884, vol. 102.
De Sandre-Giovannoli, et al., "Lamin A Truncation in Hutchinson-Gilford Progeria", *Science*, 2003, p. 2055, vol. 300.
Demyanets, et al., "Hydroxymethylglutaryl-Coenzyme A Reductase Inhibitors Induce Apoptosis in Human Cardiac Myocytes in vitro", *Biochemical Pharmacology*, 2006, pp. 1324-1330, vol. 71.
Duque, et al., "Age-Related Changes in Lamin A/C Expression in the Osteoarticular System: Laminopathies as a Potential New Aging Mechanism", *Mechanisms of Aging and Development*, 2006, pp. 378-383, vol. 127.
Efuet, et at., "Farnesyl and Geranylgeranyl Transferase Inhibitors Induce G1 Arrest by Targeting the Proteasome", *Cancer Research*, 2006, pp. 1040-1051, vol. 66.
Eriksson, et al., "Recurrent de novo Point Mutations in Lamin A Cause Hutchinson-Gilford Progeria Syndrome", *Nature*, 2003, pp. 293-298, vol. 423.
Evans, et al, "The Myotoxicity of Statins", *Current Opinion in Lipidology*, 2002, pp. 415-420, vol. 13.
Flint, et al, "HMG CoA Reductase Inhibitor-Induced Myotoxicity: Pravastatin and Lovastatin Inhibit the Geranylgeranylation of Low-Molecular-Weight Proteins in Neonatal Rat Muscle Cell Culture", *Toxicology and Applied Pharmacology*, 1997, pp. 99-110, vol. 145.
Fong, et al., "Prelamin A and Lamin A Appear to be Dispensable in the Nuclear Lamina", *Journal of Clinical Investigation*, 2006, pp. 743-752, vol. 116.
Fong, et al., "Heterozygosity for LMNA Deficiency Eliminates the Progeria-like Phenotypes in Zmpste24-Deficient Mice", *PNAS*, vol. 101, No. 52, pp. 18111-18116, 2004.
Glynn, et al., "Incomplete Processing of Mutant Lamin A in Hutchinson-Gilford Progeria Leads to Nuclear Abnormalities, which are Reversed by Farnesyltransferase Inhibition", *Human Molecular Genetics*, 2005, pp. 2959-2969, vol. 14.
Goldman, et al., "Accumulation of Mutant Lamin A Causes Progressive Changes in Nuclear Architecture in Hutchinson-Gilford Progeria Syndrome", *Proceedings of the National Academy of Sciences*, USA, 2004, pp. 8963-8968, vol. 101.
Gruenbaum, et al., "The Nuclear Lamina Comes of Age", *Nature Reviews: Molecular Cell Biology*, 2005, pp. 21-31, vol. 6.
Hampton, et al., "The Biology of HMG-CoA Reductase: the Pros of Contra-Regulation", *Trends in Biochemical Sciences*, 1996, pp. 140-145, vol. 21.
Harborth, et al., "Identification of Essential Genes in Cultured Mammalian Cells Using Small Interfering RNAs", *Journal of Cell Science*, 2001, pp. 4557-4565, vol. 114.
Hegele, et al., "Sequencing of the Reannotated LMNB2 Gene Reveals Novel Mutations in Patients with Acquired Partial Lipodystrophy", *The American Journal of Human Genetics*, 2006, pp. 383-389, vol. 79.
Hildebrand, et al., "A New Method for the Model Independent Assessment of Thickness in Three-Dimensional Images", *Journal of Microscopy*, 1997, pp. 67-75, vol. 185.
Hoffmann, et al., "Clinical and Biochemical Phenotype in 11 Patients with Mevalonic Aciduria", *Pediatrics*, 1993, pp. 915-921, vol. 91.
Huang, et al., "Correction of Cellular Phenotypes of Hutchinson-Gilford Progeria Cells by RNA Interference", *Human Genetics*, Oct. 6, 2005, vol. 118, pp. 444-450.
Hutchinson, et al., "A-Type Lamins: Guardians of the Soma?", *Nature Cell Biology*, 2004, pp. 1062-1067, vol. 6.

Kusuyama, et al., "The Effects of HMG-CoA Reductase Inhibitor on Vascular Progenitor Cells", *Journal of Pharmacological Sciences*, 2006, pp. 344-349, vol. 101.
Leung, et al., "Geranylgeranylation of Rab GTPases", *Journal of Lipid Research*, 2006, pp. 467-475, vol. 47.
Levy, et al., "Anomalies du Noyau et Maladies Genetiques", *Pour la Science*, 2003, pp. 2-7, vol. 313.
Lin, et al., "Structural Organization of the Human Gene (LMNB1) Encoding Nuclear Lamin B1", *Genomics*, 1995, pp. 230-236, vol. 27.
Lin, et al., "Structural Organization of the Human Gene Encoding Nuclear Lamin A and Nuclear Lamin C". *Journal of Biological Chemistry*, 1993, pp. 16321-16326, vol. 268.
Liu, et al., "Involvement of Xeroderma Pigmentosum Goup A (XPA) in Progeria Arising from Defective Maturation of Prelamin A", *Federation of American Societies for Experimental Biology Journal*, Feb. 2008, pp. 603-611, vol. 22, No. 2.
Mattout, et al., "Nuclear Lamins, Diseases and Aging", *Current Opinion in Cell Biology*, 2006, pp. 335-341, vol. 18.
McClintock, et al., "The Mutant Form of Lamin A that Causes Hutchinson-Gilford Progeria is a Biomarker of Cellular Aging in Human Skin", *PLoS One*, 2007, vol. 2, e1269, pp. 1-10.
Navarro, et al., "Lamin A and ZMPSTE24 (FACE-1) Defects Cause Nuclear Disorganization and Identify Restrictive Dermopathy as a Lethal Neonatal Laminopathy", *Human Molecular Genetics*, 2004, pp. 2493-2503, vol. 13, No. 20.
CL Navarro, et al., "Loss of ZMPSTE24(FACE-1) causes autosomal recessive restrictive dermopathy and accumulation of Lamin A precursors", *Hum. Mol. Gen.*, 14:1503-1513 (2005).
Padiath, et al., "Lamin B1 Duplications Cause Autosomal Dominant Leukodystrophy", *Nature Genetics*, 2006, pp. 1114-1123, vol. 38 (with corrigenda—2 pages).
Pendas, et al., "Defective Prelamin A Processing and Muscular and Adipocyte Alterations in ZMPSTE24 Metalloproteinase-Deficient Mice", *Nature Genetics*, 2002, pp. 94-99, vol. 31.
Reid, et al., "Crystallographic Analysis of CaaX Prenyltransferases Complexed with Substrates Defines Rules of Protein Substrate Selectivity", *Journal of Molecular Biology*, 2004, pp. 417-433, vol. 343.
Scaffidi, et al . . . , "Lamin A-Dependent Nuclear Defects in Human Aging", *Science*, May 19, 2006, pp. 1059-1063, vol. 312, No. 5776.
Scaffidi, et al., "Reversal of the Cellular Phenotype in the Premature Aging Disease Hutchinson-Gilford Progeria Syndrome", *Natural Medicine*, 2005, vol. 11, No. 4, pp. 1-11.
Shelton, et al., "Nuclear Envelope Proteins: Identification of Lamin B Subtypes", *Biochemical and Biophysical Research Communications*, 1981, pp. 975-981, vol. 103, No. 3.
Shumaker, et al., "The Nucleoskeleton: Lamins and Actin are Major Players in Essential Nuclear Functions", *Current Opinion in Cell Biology*, 2003, pp. 358-366, vol. 15.
Stewart, et al., "Teratocarcinoma Stem Cells and Early Mouse Embryos Contain Only a Single Major Lamin Polypeptide Closely Resembling Lamin B", *Cell*, 1987, pp. 383-392, vol. 51.
Takeda, et al., "Evidence for a Role of Human Organic Anion Transporters in the Muscular Side Effects of HMG-CoA Reductase Inhibitors", *European Journal of Pharmacology*, 2004, pp. 133-138, vol. 483.
Tsai, et al., "A Mitotic Lamin B Matrix Induced by RanGTP Required for Spindle Assembly", *Science*, 2006, pp. 1887-1893, vol. 311.
Varela, et al., "Accelerated Ageing in Mice Deficient in ZMPSTE24 Protease is Linked to p53 Signaling Activation", *Nature*, 2005, pp. 564-568, vol. 437.
Vergnes, et al., "Lamin B1 is Required for Mouse Development and Nuclear Integrity", *Proceedings of the National Academy of Sciences*, USA, 2004, pp. 10428-10433, vol. 101.
Winter-Vann, et al., "Post-Prenylation-Processing Enzymes as New Targets in Oncogenesis", *Nature Reviews: Cancer*, 2005, pp. 405-412, vol. 5.
Wydner, et al., "Chromosomal Assignment of Human Nuclear Envelope Protein Genes LMNA, LMNB1 and LBR by Fluorescence in situ Hybridization", *Genomics*, 1996, pp. 474-478, vol. 32.

(56) References Cited

OTHER PUBLICATIONS

Young, et al, "Prelamin A Farnesylation and Progeroid Syndromes", *The Journal of Biological Chemistry*, 2006, pp. 39741-39745, vol. 291, No. 52.

Zastrow, et al., "Proteins that Bind A-Type Lamins: Integrating Isolated Clues", *Journal of Cell Sciences*, 2004, pp. 979-987, vol. 117.

Sullivan, et al., "Loss of A-Type Lamin Expression Compromises Nuclear Envelope Integrity Leading to Muscular Dystrophy", *Journal of Cell Biology*, 1999, pp. 913-919, vol. 147.

Mallampalli, et al., "Inhibiting Farnesylation Reverses the Nuclear Morphology Defect in a HeLa Cell Model for Hutchinson-Gilford Progeria Syndrome", *Proceedings of the National Academy of Science (PNAS)*, 2005, pp. 14416-14421, vol. 102, No. 40.

Wang, et al., Blocking Protein Farnesylation Improves Nuclear Shape Abnormalities in Keratinocytes of Mice Expressing the Prelamin a variant in Hutchinson-Gilford Progeria Syndrome Nucleus vol. 1: Issue 5, pp. 432-439; Sep./Oct. 2010.

Bifulco, et al., N6—Isopentenyladenosine Improves Nuclear Shape in Fibroblasts From Humans With Progeroid Syndromes by Inhibiting the Farnesylation of Prelaimin A, 19 pages, 2013.

Varela, et al., Combined Treatment with Statins and Aminobisphosphonates Extends Longevity in a Mouse Model of Human Premature Aging, Nature Medicine vol. 14, No. 7, Jul. 2008, pp. 767-772.

Ramirez, et al. Human progeroid syndrome, aging and cancer: new genetic and epigenetic insights into old Questions; XP-002495855; Cellular and Molecular Life Science, vol. 64 (2007) pp. 155-170.

European Search Report issue in corresponding application No. 08873368.8-1464, dated Jun. 26, 2013.

Clark, "HIV protease inhibitors and nuclear lamin processing: Getting the right bells and whistles;" PNAS, XP055067094, Aug. 28, 2007, vol. 104, No. 35, pp. 13857-13858.

Martinez, et al., "Management of dyslipidaemia in HIV-infected patients receiving antiretroviral therapy," Antiviral Therapy, 2004, vol. 9, pp. 649-663.

Kravcik, "Update on HIV lipodstrophy," HIV Clin. Trials, 2004, vol. 5, No. 3, pp. 152-167.

Brown, et al., "Osteopenia and Osteoporosis n Patient with HIV: a review of current concepts," Current Infectious Disease Reports, Mar. 2006, vol. 8, No. 2, pp. 162-170.

\* cited by examiner

COMPOSITION AND METHODS USED DURING ANTI-HIV TREATMENT

CROSS-REFERENCE TO RELATED APPLICATIONS

This application is a Continuation of U.S. patent application Ser. No. 12/811,474, filed Nov. 3, 2010, which is a National Stage entry of International Application No. PCT/FR2008/001844, filed Dec. 31, 2008, which claims priority to U.S. Provisional Application No. 61/018,688, filed Jan. 3, 2008. The disclosures of the prior applications are hereby incorporated in their entirety by reference.

RELATED APPLICATIONS

The present application relates to French Patent Application No. FR 08/50019 filed on Jan. 3, 2008. This application also relates to French Patent Application No. FR 06/06097 filed on Jul. 5, 2006 and its corresponding PCT Application filed on Jul. 5, 2007 entitled "Medicament destine au traitement des maladies avec persistence et/ou accumulation de proteins prénylées" ["Drug intended for the treatment of diseases with persistence and/or accumulation of prenylated proteins"]. The entire contents of each of the above-referenced Patent Applications are hereby incorporated by reference.

TECHNICAL FIELD

The invention relates to an anti-HIV composition and processes for treating an HIV-infected patient.

This invention is, for example, very useful in the treatment of side effects caused by certain anti-HIV treatments, for example premature aging and lipodystrophy, which can be caused by protease inhibitors or reverse-transcriptase inhibitors.

In the description below, the references between parentheses (X) refer to the list of references at the end of the examples. The references between parentheses with the author's name and the date also refer to this list of references.

PRIOR ART

The nucleus of eukaryotic cells is delimited by a porous double membrane, the nuclear envelope, which controls molecular exchanges between the two nuclear and cytoplasmic compartments. This envelope partially isolates the contents of the nucleus, i.e. the genetic material and all of the enzymatic machinery needed for the functions of the nuclear genome.

The nuclear envelope consists of two concentric membranes, the outer membrane, continuous with the endoplasmic reticulum, and the inner membrane. The latter is bordered on its inner face by a dense fibrillated mesh called the nuclear lamina. It is a protein network composed essentially of polymers of lamins and associated proteins. In the vertebrae, two subclasses of lamins are distinguished: lamins of type A (lamins A and C) and type B (lamins B1, B2 and B3), all of which are involved in the development of the lamina. The latter is held in place by the association with other proteins, attached to the inner membrane of the nuclear envelope (cf. Gruenbaum & al. 2005 (19)).

Lamins are filament-shaped proteins belonging to the family of intermediate filaments (type V), all of which have a common structure: a short globular N-terminal (head) segment separated from another globular C-terminal (tail) segment by a long central domain organized in a plurality of alpha helices (rod domain). The globular tail contains in particular a nuclear localization signal (NLS) enabling the addressing to the nucleus after synthesis. The central domain enables two parallel lamin molecules to be associated and organized in filaments by a "head-to-tail" association of dimers. This structure gives them very resistant mechanical properties.

Only lamin A and lamins B undergo maturation after the synthesis of a precursor (cf. Gruenbaum & al. 2000 (20)). Lamin C is directly synthesized in its mature form. The precursor of lamin A and lamins B is terminated by a characteristic CaaX motif (C is a cysteine, a is an amino acid with an uncharged aliphatic chain and X is any amino acid, in this case a methionine; cf. Levy & Cau 2003 (29)).

The C-terminal CaaX motif enables the attachment of a fatty acid (in general a C15 fatty acid, farnesyl) owing to a farnesyl-transferase. This prenylation (the farnesyl motif is derived from a C5-based aliphatic unit called isoprene) enables the prelamins to be inserted in the membrane of the endoplasmic reticulum after their synthesis in cytosol. They are subjected to the action of an endoprotease itself inserted into the envelope membrane of the reticulum and of which the active site is cytosolic. The specific endoprotease of prelamin A is Face1 (or ZMPSTE24, Zinc Metallo-Protease, an STE24 yeast homolog), while Face2 (or Rce1, ras-converting enzyme) is specific to prelamins B. These enzymes catalyze the hydrolysis of the peptide bond between the cysteine and the next (aliphatic) amino acid, shortening the prelamins of 3 amino acids. The carboxyl end of the farnesylated cysteine is then recognized by an iso-prenylcysteine-carboxymethyl transferase (ICMT), which attaches a methyl group thereto by esterification.

Only the maturation of the prelamin A continues with a second endoproteolytic cleavage by Face1, which releases a 15-amino acid farnesyl-peptide and the mature lamin A. This lamin A, which no longer comprises the fatty acid, becomes soluble, is imported into the nucleus owing to its nuclear localization signal, and is localized in the nuclear lamina itself as well as in the rest of the nuclear compartment, constituting a veritable nuclear skeleton (Gruenbaum & al. 2005 (19)). The mature lamin B on the other hand still has, at the C-terminal end, its farnesylated and methyl-esterified cysteine. It therefore remains inserted in the envelope membrane of the reticulum, then in the nucleoplasmic face of the nuclear envelope, hence its exclusive localization in the nuclear lamina, under the inner membrane of the nuclear envelope where it is anchored.

By prenylation, we mean the attachment to the thiol group of a cysteine, either by a farnesyl chain with 15 carbon atoms, thus farnesylation, or by a geranyl-geranyl chain of 20 carbon atoms, thus geranyl-geranylation (Reid & al. 2004 (39)), or by any other isoprene derivative.

Farnesylation, catalyzed by farnesyl-transferase (FTase), which recognizes the C-terminal consensus sequence (CaaX), preferably binds a farnesyl group to the cysteine residue of the motif.

Geranyl-geranylation is the attachment by Geranyl-geranyl-transferase (GGTase) of a Geranyl-geranyl group on the cysteine residue of the motif.

These fatty acids are produced by biosynthesis, which on the basis of hydroxymethyl-glutaryl-Coenzyme A, is used by the cells to produce in particular cholesterol, steroids, the heme of hemoglobin and ubiquinones (Hampton & al. 1996 (20)).

The family of prenylated proteins comprises around 300 members in the human genome, of which the majority can be identified by the C-terminal motif CaaX (Reid & al. 2004 (39)). The proteins of the Ras, Rho and Rab families (Leung & al. 2006 (28)), certain proteins ensuring an import function to the mitochondria (HDJ2), and certain mitotic proteins (CENPE, CENPF) are in particular prenylated (Winter-Vann & Casey 2005 (51)). In general, if in the CaaX motif, X is a serine, a methionine, a cysteine, an alanine or a glutamate, the isoprenoid preferably grafted is farnesyl. If X is a leucine, the recognition of the CaaL motif will be done preferably by GGTase, which will catalyze the transfer of a geranyl-geranyl group (Basso & al. 2006 (1)). It is probable that other groups derived from isoprene can also be bound to this cysteine, although it is not described in the literature.

In humans, there are three lamin genes. The LMNA gene, located at 1q21.2-q21.3 (Wyder & al. 1996 (52)), gives lamins A and C by alternative splicing. The LMNA gene is composed of 12 exons. The start of the exon 1 codes the globular N-terminal end common to lamins A and C; the end of exon 1 and up to the start of exon 7 code the central helical part; finally, the other exons code the globular C-terminal end (Levy & Cau 2003 (29)).

In fact, the gene codes for 4 products spliced differently, the 2 main ones being the lamins C and the prelamin A (Lin & Worman 1993 (31)). The differential production of lamins A and C is done by using an alternative splicing site at the level of the exon 10 of the pre-messenger, so that the lamin C is coded by exons 1 to 10 and lamin A is coded by exons 1 to 9, the first 90 base pairs of exon 10, and exons 11 and 12 (lamin A-specific).

Consequently, the prelamin A and lamin C peptides are identical at the level of the first 566 amino acids, while the C-terminal ends of the lamins C and the prelamin A then contain, respectively, 6 and 98 specific amino acids.

The lamins of type B include three different proteins (Shelto & al. 1981 (43)): lamins B1, B2 (the two isoforms best represented) and B3. The LMNB1 gene is located at 5q23.3-q31.1 and comprises 11 exons coding the lamin B1 (Lin & Worman 1995 (30)). The LMNB2 gene is localized at 19p13.3 and codes for lamins B2 and B3 by an alternative splicing mechanism (Biamonti & al. 1992 (2)).

Lamins B are constitutively expressed in all of the cells from the first stages of development, while lamins of type A are generally absent from the embryonic stem cells (Stewart et al. 1987 (45)) and are expressed in all of the differentiated somatic cells. Their expression is subject to regulations according to the tissue and the life course (Duque & al. 2006 (9)). It appears that their expression is not necessary, since mice in which the expression of lamin A was specifically blocked, but which still express lamin C and other lamins, do not have an apparent phenotype (Fong & al. 2006 (14)).

Lamins interact with a very large number of protein partners having a wide variety of functions; they are consequently involved in a large number of nuclear processes, including DNA replication and repair, control of transcription and splicing, and organization of the chromatin structure (cf. Shumaker & al. 2003 (44), Zastrow & al. 2004 (54), Hutchison & al. 2004 (26), Gruenbaum & al. 2005 (19)). The alterations of the structure of the lamina are at the origin of numerous human hereditary pathologies. They are due to mutations of genes coding the lamins, or other proteins of the lamina. These pathologies have been grouped together under the generic term laminopathies (Broers & al. 2006 (5), Mattout & al. 2006 (33)). Recently, mutations in the genes of the enzymes responsible for the maturation of lamins (Face1 in particular) have been identified, leading to pathologies also belonging to the group of laminopathies (Navarro & al. 2004 (36) and 2005 (35)). At present, the only pathology in humans associated with mutations of the LMNB1 or 2 genes is a leukodystrophy caused by a complete duplication of the LMNB1 gene (Padiath & al. 2006 (37)). Doubt remains as to the potential involvement of variations of sequences found in LMNB2 in patients with Barraquer-Simon syndrome (Hegele & al. 2006 (22)). However, it has been demonstrated in vitro by RNAi (RNA-interference) experiments, as well as in the murine model (Vergnes & al. 2004 (50)), that lamins of type B are essential for cell development and integrity. Indeed, a lamin B1 deficiency causes perinatal lethality in mice. Moreover, the nuclei of the embryonic fibroblasts of the same LMNB1-deficient mice show remarkable alterations in nuclear morphology, similar to those observed in patients with LMNA gene mutations. Moreover, it has recently been shown that lamins B are necessary for the formation of the division spindle during mitosis, which tends to prove that they have a dynamic and multifaceted role over the course of the cell cycle, and that their role is not restricted to maintaining the nucleus architecture (Tsai & al. 2006 (48)). On this last role, a recent article demonstrates the structural function of lamins B: cells artificially deprived of lamins B1 have a "floating" nucleus in the cell, which turns around (Liu & al. 2007 (45)). The functional redundancy existing between the two lamins B1 and B2 is undoubtedly also a direct reflection of their importance, exerting a strong selection pressure and masking the effect of any potential mutations in the sequence of the corresponding genes.

The functional alterations of lamins A/C, due to mutations of the LMNA gene, are the origin of at least 15 disorders including a wide range of pathologies in a clinical spectrum ranging from mild forms, affecting a single tissue in isolation, to systemic forms that are lethal in the perinatal period.

A number of mutations of the LMNA gene notably modify the assembly of proteins in the nuclear envelope and disrupt its functioning. In the cells of various tissues, the morphology of the nuclei is altered: they often have bulges that extrude genetic material into the cytoplasm (Goldman & al. 2004 (18)).

The proteins normally associated with the nuclear envelope, lamins B, certain nuclear pore proteins and LAP2 proteins, are absent from the edge these bulges. These morphological abnormalities are followed by functional alterations, and end by causing cell death. Among all of the pathologies included under the term laminopathies, only those associated with the abnormal accumulation of a prenylated protein form are concerned by this invention.

These primarily include Hutchinson-Gilford or Progeria syndrome (De Sandre-Giovannoli & al. 2003 (7), (Eriksson & al. 2003 (11)), and restrictive dermopathy (Navarro & al. 2004 (36)). In these 2 syndromes, the physiopathological cause is an accumulation and persistence of immature farnesylated prelamin in the cells of patients.

Restrictive dermopathy, lethal around the natal period, is characterized by clinical signs that are almost always the consequence of a cutaneous deficit that restricts in utero movements. This pathology is very rare. The skin is rigid and taut, and gives way in places, causing, for example, tears at the armpits or the neck. The eyelashes, the eyebrows and the skin down are absent or very sparse. Hydramnios is often present, and the decrease in fetal movements is observed from the $6^{th}$ month of pregnancy. At the skeletal level, the radiography shows contractures of all joints, congenital convex pes valgus, thin, dysplasic and bi-partite clavicles, thin ribs, long tubular arm bones and demineralization of the skull. The transmission of lethal restrictive dermopathy is recessive autosomal. LMNA and ZMPSTE24/Face1 mutations have been reported for this pathology (Navarro & al. 2004 (36)). In both cases, the physiopathological mechanism is the same: the prelamin A cannot mature (null mutation of Face1 or disappearance of the cleavage site by mutation of prelamin A) and remains farnesylated, and therefore inserted in the nuclear membrane. The accumulation and persistence in the cells of these abnormal precursors, which probably prevent the normal interactions of lamins B and C with their partners, causes the death of the cells and, after a short time, of the patient. It has clearly been demonstrated that it is the persistence of the farnesyl group, and not the absence of mature lamin A, as might initially be thought, that is responsible for the cell toxicity (Fong & al. 2004 (16)).

In April 2003, based on an overlap of symptoms common to acromandibular dysplasia and certain diseases causing premature aging, the inventors showed that Progeria, the most typical and serious form of premature aging, results from a mutation of the LMNA gene (De Sandre-Giovannoli & al. 2003 (7)). The children affected by this disease, also called Hutchinson-Gilford syndrome, suffer from accelerated aging, which occurs up to ten times faster than that of a normal individual, and have a life expectancy of no more than 13 years. In Europe, one in around six million children is affected. The symptoms are skin aging, baldness, reduced jaw size and ageing-related problems such as joint stiffness and cardiovascular disorders. The latter, including myocardial infarction or atherosclerosis, are often the cause of death.

The mutation considered responsible, located at exon 11 of the LMNA gene, activates a cryptic splicing site of the pre-mRNA, leading to an mRNA with 150 nucleotides deleted (De Sandre-Giovannoli & al. 2003 (7), Eriksson & al. 2003 (11)). This deleted mRNA involves an abnormal prelamin A, progerin, which cannot mature into a normal lamin A: the absence of 50 amino acids of the exon 11 comprising the protease recognition site blocks the $2^{nd}$ cleaving of the progerin, of which the C-terminal end preserves its farnesyl group. It therefore remains inserted in the nucleoplasmic face of the nuclear envelope, which has characteristic alterations, bulges of the nucleoplasm in the cytosol and abnormalities in the distribution of peripheral heterochromatin (Goldman & al. 2004 (18)). Again, it is the persistence of the farnesyl group, which is also necessary for anchoring to the envelope membrane of the reticulum in which some of the enzymes responsible for maturation (cleavage, methylation) are located, that is responsible for the cell toxicity of progerin (Fong & al. 2004 (16)).

These systemic pathologies have the special feature of being associated with the premature appearance of signs normally associated with aging. Their common physiopathological characteristic is that they generate a prenylated lamin, with the consequences described.

Two recent studies have shown that a reduction in the intranuclear accumulation farnesylated prelamin, truncated or not, effectively prevents the appearance of the cellular phenotype. The first study was conducted on the Face1 protease-deficient progeroid murine model (Pendas & al. 2002 (38)). When they are crossed with mice expressing half the amount of lamin A (mouse Lmna +/−), the effects of the absence of Face1 are reduced (Varela & al. 2005 (49)). The second study shows that the treatment of cells of HGPS patients by morpholino (antisense oligonucleotides) targeting the cryptic splicing site eradicates the mutant phenotype (Scaffidi & Misteli 2005 (43)).

A number of recent studies (see Scaffidi & Mistelli 2006 (42)) show the involvement of lamin A in the physiological aging process. In particular, it has been demonstrated that during physiological aging, progerin is synthesized by the cells in the absence of any LMNA gene mutation due to the quiet use of the cryptic splicing site of exon 11. This progerin is localized in the lamina, at the periphery of the cell nuclei. Cell nuclei in patients aging "normally" can have bulges characteristic of a laminopathy caused by accidental splicing events, which lead to abnormal cell functions and probably at least partially responsible for their aging.

In the skin in vivo, progerin is also synthesized by a subpopulation of dermal fibroblasts and keratinocytes, cells in which it accumulates with age. Progerin could therefore be a marker of skin aging (McClintock et al. 2007 (34)).

It appears that identical molecular mechanisms are responsible for signs of premature aging in individuals with Progeria and, at a much lower level, are involved in the physiological aging of individuals who do not have mutations.

The prior art describes two therapeutic approaches to improving the cell phenotype caused by the pathological production of progerin. The first of these solutions is very simply to prevent the use by the spliceosome of this cryptic splicing site in exon 11, by "masking" it by a treatment with an antisense oligonucleotides (Scaffidi & Misteli 2005 (41)), or with a retrovirus producing an siRNA (Huang & al. 2005 (25)). The results are promising in vitro, but this is "gene" therapy, and the development of a drug based on this approach is extremely long and complicated, with all of the inconveniences associated with OAS vectorization in order to obtain an in vivo effect. The second solution consists of inhibiting farnesyl-transferase, the enzyme that catalyzes the transfer of the farnesyl group to the prelamins from farnesyl-pyrophosphate. When such inhibitors (FTI) are used, a "normal" nuclear envelope is only partially restored on HGPS (Progeria) cells in culture, and the survival of RD mice (KO ZMPSTE24) is improved (Glynn & Glover 2005 (17), Capell & al. 2005 (6), Toth & al. 2005 (47), Fong & al. 2006 (15)).

However, the blocking of farnesylation can induce compensatory geranyl-geranylation (Bishop & al. 2003 (3), Varela & al. 2008 (54 bis)).

In addition, it was recently reported that FTIs caused the cell cycle to stop by blocking proteasome (Demyanets & al. 2006 (8), Efuet & Keyomarsi 2006 (10)). Thus, the treatment undoubtedly causes an accumulation, in the nucleoplasm, of progerin, probably ubiquitinylated, not degraded by the proteasome.

Also, recent studies report that the reduction in the rates of farnesylation of progerin in vivo is very low, on the order of 5% (Young & al. 2006 (53)), which is not enough to explain the restoration of the nuclear morphology observed in vitro.

Finally, FTIs are specific to only one of the protein prenylation pathways, and cannot be envisaged as general post-translational prenylation inhibitors.

Additionally, it is reported that the total absence of one of the enzymes of this pathway, mevalonate-kinase, is lethal during infancy (homozygotic mutation loss-of-function of the gene coding for this enzyme, syndrome reported by Hoffmann & al. 2003 (24)).

Anti-HIV Treatments and Side Effects

1. HIV-Infected Patients Subjected to an Antiretroviral Treatment Show Clinical and Biological Signs of Accelerated Aging Comparable to that Observed in Patients with a Genetic Progeroid Syndrome.

Antiretroviral treatments, reverse-transcriptase inhibitors, nucleosidic (NRTI) or not (NNRTI), and viral protease inhibitors (PI) have made it possible to prolong the lives of AIDS-infected patients in whom the consequences of "physiological" aging appear (Casau 2005; Levy et al. 2003).

However, the infection itself and the antiretroviral treatments show the same clinical and biological signs as those seen in patients with a genetic accelerated aging syndrome (for a recent review of these syndromes, see Navarro et al. 2006).

Certain Manifestations Appear to be Related Directly to the Viral Infection:

For example, the mutated helicase in Werner syndrome (OMIM 277700), a premature aging syndrome associated with a predisposition to cancer and atherosclerosis, recruits cell protein cofactors essential for the transactivation of the LTR of HIV-1 and to the replication of the virus. The slightest availability of helicase in infected cells could lead to aging and immunosuppression (Sharma et al., 2007).

Another example is modifications of the transport of cholesterol in macrophages. The viral protein Nef inhibits permeases of the ABC family responsible for cholesterol efflux (Bukrinsky and Sviridov, 2006; Mujawar et al., 2006; Wang and Rader, 2007). The accumulation of cholesterol in macrophages transforms them into foam cells involved in the formation of atheromatous plaques in the vascular walls (Pennings et al., 2006). Antiretroviral drugs also inhibit the cholesterol efflux of macrophages and contribute to the formation of atheromatous plaque (Azzam et al., 2006; Dressman et al., 2003; Wang et al., 2007).

Numerous Clinical and Biological Manifestations Appear Also to be the Consequence of Antiretroviral Treatments:

They reproduce the signs observed in genetic progeroid syndromes, such as Hutchinson-Gilford Progeria (OMIM 176670, see Hennekam, 2006), acromandibular dysplasia (OMIM 248370) and the lethal neonatal form, restrictive dermopathy (OMIM 275210) associated with mutations in the LMNA gene coding for lamins A and C or with mutations in the ZMPSTE24 protease (FACE1) responsible for cleavage of prelamin A during its maturation into lamin A:

Alopecia (Torres et al., 2007; Wiwanitkit, 2004), independent of infectious dermatological manifestations (Maurer, 2005).
  Skeletal system abnormalities, in particular osteoporosis (Brown and Qaqish, 2006; Thomas and Doherty, 2003) for which a correction with vitamin D and a biphosphonate has been proposed (Mondy et al., 2005).
  Muscle atrophy (Restrepo et al., 2006; Restrepo et al., 2004; Tehranzadeh et al., 2004a; Tehranzadeh et al., 2004b), in relation with the ubiquitine-proteasome system (Coistelli and Baccino, 2003) or calpains (Bartoli and Richard, 2005; Costelli et al., 2005), two proteolytic systems inhibited by certain antiretroviral treatments (see below). The calpain 3 muscle mutations are responsible for a form of girdle muscular dystrophy (LGMD2A, OMIM 253600; Richard et al., 1995) of which eosinophilic myositis might be one of the first signs (Krahn et al., 2006).
  Cardiomyopathy (Barbaro, 2003; Restrepo et al., 2006), independent of cardiovascular complications (see below), in relation with the mitochondrial toxicity of NRTI (Lewis, 2003).
  Cardiovascular abnormalities (Mondy and Tebas, 2007) with lipid metabolism disorders (Hui, 2003; Jones et al., 2005; Moyle, 2007), atheroma (de Saint Martin et al., 2006; Thomas and Smart, 2007; van Wijk et al., 2006), endothelial cell lesions (Chen et al., 2005; Jiang et al., 2006; Zhong et al., 2002) and adipose cell differentiation abnormalities (Kim et al., 2006; Roche et al., 2002). Dyslypidemia was able to be treated with statins (Benesic et al., 2004; Liang et al., 2006; Malon et al., 2006) or with an inhibitor of intestinal absorption of cholesterol (Negredo et al., 2006). It should be noted that pravastatin, which partially corrects some of the parameters altered in the metabolic syndrome (Yamagishi et al., 2006) causes an increase in subcutaneous adipose tissue without a notable improvement in cholesterolemia (Gharakhanian et al., 2006; Mallon et al., 2006).
  Clinical manifestations associated with hypoandrogenemia are frequency observed in men (Cohan, 2006) and cases of premature menopause in HIV-positive women are the subject of a number of publications (Cohan, 2006; Ferreira et al., 2007).

Virus Protease Inhibitors (PI) have a Plurality of Cell Targets, Including Proteases:

The inhibition of proteasome (Piccinini et al., 2005) has highly varied consequences due to the role of this proteolytic assembly on numerous cell functions, protein turnover, cell cycle control, apoptosis, gene transcription, signal transduction, senescence, stress response, and so on (Naujokat et al., 2007). For example, one of the ways in which PIs block adipocyte differentiation involves non-production of the NFkB transcription regulation factor, which controls the transcription of the gene coding for metalloprotease (zinc) MMP9 involved in adipocyte differentiation (Bourlier et al., 2005; De Barros et al., 2007).

Another example is the signaling pathway involved by insulin (Rudich et al., 2005; Schutt et al., 2004). The PIs inhibit the activity of insulin-degrading enzyme (Hamel et al., 2006), block the potassium channels responsible for insulin secretion (Neye et al., 2006), interact with Glut4 glucose transporters (Hertel et al., 2004) and prevent their insertion in the plasma membrane (Hruz, 2006; Parker et al., 2005).

Similarly, the PIs block the signaling pathway via Akt kinase involved by the activation of tyrosine-kinase activity receptors (Gupta et al., 2005), including IGF1. IGF1 directly controls muscle atrophy or hypertrophy (Glass, 2003).

The PIs exert an anti-apoptotic effect by calpain inhibition, Ca-dependent cytosolic proteases (Ghibelli et al., 2003; Lichtner et al., 2006), and which control the apoptosis-autophagy balance by ATG5 cleavage, essential for the formation of the autophagic vacuole (Yousefi et al., 2006).

Two other enzymatic systems are blocked by the PIs: certain P450 cytochromes of the subfamily 3A, intestinal or hepatic (Granfors et al., 2006), while other P450 cytochromes of the subfamily 2A are induced (Yeh et al., 2006) at the same time as other transporters (Dixit et al., 2007; Yeh et al., 2006); glucuronide conjugation in the RE, in particular bilirubin (Zhang et al., 2005).

The inhibition of a plurality of enzymatic activities in which the proteasome induces endoplasmic reticulum stress, the activation of the UPR (Unfolded Protein Response) and the involvement of the signaling mechanism of the reticulum of the nucleus with the appearance of transcription regulation factors (Zhou et al., 2006). Numerous publications show the increase in the amount of SREBP (Sterol Response Element Binding Protein) isoforms, which control the activation of genes regulating the lipid metabolism, including cholesterol (Colgan et al., 2007; Miserez et al., 2002; Nguyen et al., 2000; Williams et al., 2004; Zhou et al., 2006; Zhou et al., 2005). The induction by the PIs of SREBP transcription has also been shown by a study of the transcriptome (chips, quantitative PCR) of adipocytes in the process of differentiation (Pacenti et al., 2006) and the effect is increased by the absence of SREBP degradation by the ubiquitine-proteasome system.

The PIs induce the nuclear accumulation of SREBP in the hepatocytes and the adipocytes and its consequences on the lipid metabolism (increased synthesis of fatty acids and cholesterol) (Hui, 2003; Riddle et al., 2001).

Three articles by the same Parisian team analyzing the in vitro differentiation of adipocytes successively show that the PIs cause an insulin resistance syndrome, the abnormal localization of SREBP in the nucleoplasm, in relation with an abnormality in the localization of lamin A (Caron et al., 2001); the inhibition of SREBP cleavage (by the Golgi proteases S-1P and S-2P, see Seidah et al., 2006), and its consequences on the synthesis of lipid metabolism enzymes, on abnormal maturation of lamin A, while the maturation of lamin B is not modified (Caron et al., 2003); the similarity between the mitochondrial stress observed in lipodystrophies associated with a mutation of the LMNA gene and that resulting from treatment with PIs (Caron et al., 2007).

One of the benefits of these studies is that they strongly suggest that certain PIs block the protease (FACE1 or ZMPSTE24) involved in the maturation of prelamin A, data that has been confirmed by an American team (Coffinier et al., 2007). These PIs, on the contrary, have no effect on the activity of the protease FACE2 (or Rce1, Ras converting enzyme 1), responsible for the cleavage of prelamins B, but also that of the Ras monomer protein G, cleavage necessary for its maturation (Wright and Philips, 2006). A recent quantitative RT-PCR study shows that PIs cause a decrease in the amount of mRNA coding for lamin A without modifying the amount of mRNA coding for lamin C (Miranda et al., 2007).

PIs inhibit the mitochondrial proteases responsible for the cleavage of mitochondria addressing signals, mitochondrial protein renewal, and the control of certain mitochondrial GTPases (OPA1) involved in the fusion of mitochondriae and apoptosis (Mukhopadhyay et al., 2002; Roehl White and Lauring, 2007).

Independently of their action on calpains (see above), PIs exert an anti-apoptic effect for T-lymphocytes by blocking, via the protein UCP2, the depolarization of the inner membrane caused by pro-apoptotic stimuli (Matarrese et al., 2003; Matarrese et al., 2005).

It should therefore be noted that PIs therefore inhibit different enzymes of aspartyl-protease specific to the AIDS virus (Dunn et al., 2002). Although the literature is currently silent on this point, PIs may also inhibit certain eukaryotic aspartyl-proteases (see the site "Degradome": http://www.uniovi.es/degradome/) such as presenilin, the peptidase peptide signal, or Ddil (DNA damage inducible protein), capable of binding both to the proteasome and ubiquitinylated proteins in order to degrade the latter (Sirkis et al., 2006).

The Nucleoside Reverse Transcriptase Inhibitors (NRTI) of the Virus Also have a Plurality of Cell Targets, of which the Mitochondria is One of the Most Important:

Non-nucleoside reverse transcriptase inhibitors of the virus, less often studied, appear to have a more specific action on the viral enzyme while inducing the apoptosis of a T-cell line (Pilon et al., 2002).

NRTIs are incorporated into the nuclear DNA (Olivero et al., 1999) and their mutagenic effect can cause a blockage of the cell cycle (Olivero et al., 2005). A mutation of the gamma polymerase DNA has been reported (Yamanaka et al., 2007), responsible for mitochondrial DNA replication and repair (Hudson and Chinnery, 2006).

A small number of publications show that NRTIs inhibit N-glycosylation (in the endoplasmic reticulum), O-glycosylation and the modification of arborizations incorporating sugars (in the Golgi), by interfering with the nucleotide transporters in the Golgi of the precursors of arborizations incorporating sugars (Lizzi et al., 2007). A number of muscular dystrophies are associated with genetic abnormalities of glycosylation (Muntoni et al., 2004; Percival and Froehner, 2007).

The NRTIs are transported in the mitochondrial matrix by a family of specialized transporters into that of the deoxynucleoside diphosphates, which are phosphorylated by a mitochondrial kinase before being incorporated in the mitochondrial DNA by the DNA polymerase gamma (Palmieri, 2004).

The genotoxicity of NRTIs causes an increase in the rate of mitochondrial DNA mutations and a decrease in the number of its copies in the mitochondria (Kohler and Lewis, 2007; Olivero, 2007).

The abnormalities of the mitochondrial DNA and those of the functioning of DNA polymerase gamma have consequences on the synthesis of the 13 proteins of the inner membrane constituting, with proteins coded by the nuclear genome and imported, the complexes of the respiratory chain and ATP synthase. The disruptions of the mitochondrial DNA and its polymerase cause, for example, a reduction in the amount of cytochromes oxidase II (Vidal et al., 2006), the production of reactive oxygen species (ROS) (Jiang et al., 2007) with consequences on the hepatocytes, adipocytes, cardiomyocytes and endothelial cells involved in lipodystrophy and cardiovascular complications.

The increase in the plasma lactic acid level is one of the criteria of mitochondrial dysfunction caused by antiretroviral treatments (2007; John et al., 2001).

NRTIs also inhibit telomerase activity and cause telomere shortening (Olivero, 2007; Yamaguchi et al., 2001).

In conclusion, antiretroviral treatments have an impact on metabolic mechanisms and pathways grouped together in a number of cell theories attempting to explain normal or accelerated aging:

the "mitochondrial theory",
the "nucleus and lamin" theory, which appeared in 2003 with the discovery that the LMNA gene is responsible for Progeria,
the "telomeric" theory,
the "gene transcription regulation" theory, in particular with proteins p53, NF-kB,
the "metabolic" theory with involvement of the signaling pathways, some of which are activated by membrane receptors,
A number of animal models of premature aging or, by contrast, of increasing lifespan, show partial overlaps between the metabolic pathways involved in each of these theories and interrelations, on a cellular scale, between the cytosol and in particular the protein degradation mechanisms (Grillari et al., 2006), the mitochondria, the nucleus and the plasma membrane (Irminger-Finger, 2007; Kenyon, 2005; Martin and Loeb, 2004; Quarrie and Riabowol, 2004).

A number of animal models of premature aging or, by contrast, for increasing lifespan, show partial overlaps between the metabolic pathways involved in each of these theories and interrelations, on a cellular scale, between the cytosol and in particular the protein degradation mechanisms (Grillari et al., 2006), the mitochondria, the nucleus and the plasma membrane (Irminger-Finger, 2007; Kenyon, 2005; Martin and Loeb, 2004; Quarrie and Riabowol, 2004).

2. The "Mitochondrial" Theory of Aging (Appended FIG. 6)

The three main components of the mitochondrial theory of aging are i/the increase in production of reactive oxygen species (ROS) by complexes I and II of the respiratory chain, ii/progressive dysfunctioning thereof, and iii/accumulation of mitochondrial DNA lesions (Balaban et al., 2005; Meissner, 2007; Wallace, 2005). The mitochondrial DNA is more sensitive than nuclear DNA to the effects of ROS, which target the DNA polymerase gamma (Graziewicz et al., 2002; Richter et al., 1988). Two murine models expressing a DNA polymerase gamma defective in its proofreading function show accelerated aging with mutations of the mitochondrial DNA (Kujoth et al., 2005; Trifunovic et al., 2004). The mitochondrial toxicity of ROS can be eradicated by the overexpression of peroxysomal catalase addressed to the mitochondria in a transgenic murine model in which the lifespan is increased (Schriner et al., 2005).

In humans, aging is accompanied by a decrease in mitochondrial functions, including those of the respiratory chain (Short et al., 2005; Trifunovic et al., 2005), and an increase in deletions in the mitochondrial DNA, very specifically observed in neurodegenerative diseases (Bender et al., 2006; Kraytsberg et al., 2006). A mitochondria-to-nucleus signaling mechanism, which is not yet understood, causes the protein p32 to become involved, in particular during aging or in ROS-induced pathologies (Jiang et al., 1999; Storz, 2006). This protein, coded by the nuclear genome, then imported into the mitochondrial matrix, is re-exported to the nucleoplasm (Brokstad et al., 2001) where it controls transcription (Chattopadhyay et al., 2004) and splicing (Petersen-Mahrt et al., 1999) of mRNA. It interacts with the lamin B receptor, localized the nucleoplasmic face of the nuclear envelope (Mylonis et al., 2004; Simos and Georgatos, 1994).

The nucleus-to-mitochondria signaling mechanism involves the around 1500 proteins coded by the nuclear genome, which are synthesized in the cytosol, then imported into the mitochondria (Calvo et al., 2006; Truscott et al., 2003).

Among these proteins, p53 is involved in accelerated aging in a murine model (Tyner et al., 2002) and participates in deregulations in the context of the "nuclear" theory (see below). Protein p53 controls mitochondrial respiration (Matoba et al., 2006), and exerts pro- and anti-oxidant effects owing to the control of nuclear gene transcription (Bensaad and Vousden, 2005; Sablina et al., 2005). It maintains the stability of the mitochondrial DNA by interacting with DNA polymerase gamma (Achanta et al., 2005).

Finally, mitochondrial fission (division) and fusion mechanisms, involving a plurality of GTPases of the outer mitochondrial membranes (Drp1, mitofusins, etc.) and inner mitochondrial membranes (OPA1) and a plurality of associated proteins (Fis1, etc.) modulate the cell aging process: the elongation of the mitochondrial network by permanent fusion induces a cell aging process with a decrease in the difference in potential between the two faces of the inner membrane, and increase in the production of ROS and DNA lesions. These phenotype modifications are neutralized by fragmentation of the mitochondrial network (Lee et al., 2007).

3. The Mechanisms of Genetic Accelerated Aging Syndromes in the Context of the "Nucleus and Lamin" Theory Lamins are proteins forming intermediate filaments localized exclusively in the nucleoplasm. The LMNA gene codes primarily for lamins A and C, produced by alternative splicing. Two other genes code for lamins B1 and B2.

Lamins A and B are synthesized in the cytosol in the form of a precursor that is subject to a plurality of maturation steps. The 3 proteins have, at their C-terminal end, the CaaX box (a cysteine, two aliphatic amino acids, one indifferent amino acid). This CaaX sequence enables the farnesylation of lamins A and B (and around 300 other proteins of the human genome). The farnesyl residue (isoprenoid with 15 carbon atoms) is synthesized in an intermediate step of the cholesterol synthetic pathway (appended FIG. 7). A cytosolic enzyme, farnesyl-transferase, binds the farnesyl residue to the cysteine.

The presence of the fatty acid residue enables the anchoring of prelamins A and B in the cytosolic layer of the envelope membrane of the endoplasmic reticulum (ER). The prelamins A and B are then cleaved by FACE1 (ZMPSTE24) or FACE2 (Rce1), respectively, and lose their last three C-terminal amino acids aaX. The proteins still anchored in the envelope membrane of the ER are subjected to the action of a second enzyme, ICMT, which binds a methyl group to the already-farnesylated cysteine.

The maturation of lamins B ends with this step. These proteins glide in the plane of the envelope membrane of the ER, then of the cytosolic face of the nuclear envelope, pass through the nuclear pore and are localized in the nucleoplasmic layer of the nuclear envelope, where they become involved in the formation of the nuclear lamina and where they interact with a plurality of proteins, including the lamin B receptor. The anchoring to the envelope results in the absence of lamins B in the nuclear matrix, inside the nucleoplasm and at a distance from the envelope.

The farnesylated and carboxymethylated prelamin A on the same C-terminal cysteine is subjected to a final maturation step by proteolytic cleavage of the last 15 amino acids by FACE1 (and perhaps by Rce1). The lamin A loses its anchoring to the ER, becomes soluble, and is imported into the nucleoplasm (like lamin C) through the nuclear pore, like all of the soluble proteins, owing to its nuclear localization signal, which recruits the necessary importation complex (appended FIG. 8).

In the nucleoplasm, lamin A (and lamin C) is localized in the nuclear lamina, under the nuclear envelope, where it interacts with numerous proteins inserted in the nucleoplasmic layer of the envelope. Lamins A and C (unlike lamins B) are also dispersed in the rest of the nucleoplasm where they become involved in the formation of the nuclear matrix or nucleoskeleton (appended FIG. 6).

The nuclear matrix controls the functioning of the nuclear genome: replication, DNA repair, RNA transcription, mRNA splicing, maturation of other RNA, etc., and its constituents, including lamins A and C, interact with a large number of proteins imported into the nucleoplasm (p53, SREBP, etc.) as shown by the abnormalities observed in genetic laminopathies (Broers et al., 2006; Vlcek et al., 2001; Vlcek and Foisner, 2006). The nucleoplasmic slope of the nuclear envelope and its transmembrane proteins, as well as the lamins of the lamina, contributes to the storage of transcription regulation factors, before their use and in gene expression regulation (Heessen and Fornerod, 2007; Shaklai et al., 2007).

The first laminopathies discovered from 1999 presented as diseases predominantly in a given tissue, skeletal muscle, cardiac muscle, etc., whereas lamins are ubiquitous proteins (Vlcek and Foisner, 2007a; Vlcek and Foisner, 2007b; Worman and Bonne, 2007). The lipodystrophies associate lipid metabolism abnormalities and insulin-resistance with disorders in the bodily distribution of adipose tissue, matching the lipodystrophy observed during antiretroviral treatments (Capeau et al., 2005). "Systemic" laminopathies were discovered after 2002: acromandibular dysplasia (OMIM 248370; (Agarwal et al., 2003; Novelli et al., 2002); Hutchinson-Gilford progeria, (OMIM 176670; (De Sandre-Giovannoli et al., 2003; Eriksson et al., 2003); restrictive dermopathy (OMIM 275210; (Navarro et al., 2005; Navarro et al., 2004). They involve all of the patient's body tissue, skin and appendages, skeletal and cardiac muscle, bone and cartilage tissue, adipose tissue and its metabolic consequences, but, in particular, they are accompanied by accelerated aging, the most severe being restrictive dermopathy, lethal at birth. These three diseases are associated either with a mutation in the LMNA gene coding for lamins A and C, or in the FACE1 gene (ZMPSTE24) coding for the protease of the ER, which in two stages cleaves the prelamin A. The mutation of the LMNA gene causes a disappearance of the site of recognition by FACE1 of prelamin A: the protein is not cleaved, and therefore preserves its farnesyl residue, and is imported into the nucleoplasm by gliding along the envelope membranes like lamins B (Pan et al., 2007). The farnesylated prelamin A remains anchored in the nucleoplasmic face of the nuclear envelope where it disrupts the organization of the lamina and the interactions between the lamina and the membrane proteins of the envelope, which involves characteristic nuclear deformations (Goldman et al., 2004).

The rest of the nuclear matrix is free of lamin A, with multiple functional consequences, for example the activation of pathways downstream of p53 (Varela et al., 2005), abnormalities of mitosis (Cao et al., 2007; Dechat et al., 2007), and of DNA repair (Liu et al., 2005; Liu et al., 2006; Liu et al., 2007b), etc., leading to cell aging (Kudlow et al., 2007). The analysis of the transcriptome of cells of progeria patients has shown abnormalities in the expression of genes involved in atherosclerosis (Csoka et al., 2004).

It appears to be likely that accelerated aging in patients treated with certain antiretrovirals, in particular PIs that inhibit ZMPSTE24 (FACE1), obeys the same mechanisms.

The mutation of the LMNA gene responsible for progeria unmasks a cryptic splicing site that leads to the synthesis of an mRNA deleted of 150 nucleotides coding for progerin, a prelamin A deleted of 50 amino acids and which preserves its farnesyl group. This same protein is produced during physiological aging, in the absence of any mutation of the LMNA gene, due to an error, associated with age, of the splicing machinery (Scaffidi and Misteli, 2006). Progerin is accumulated in dermal fibroblasts localized under the basal lamina, as well as in the keratinocytes. It could be a marker of cutaneous aging (McClintock et al., 2007).

The nuclear modifications (bulges of the nucleoplasm into the cytosol, breaching of the envelope, nuclear contour irregularities, etc.) observed in the cells of patients with progeria are also similar to the transient modifications induced by the viral protein Vpr, which facilitates the entrance, by transient breaching of the nuclear envelope and the lamina, of the pre-integration complex of the AIDS virus, which complex is too large to be imported into the nucleoplasm via the nuclear pores (de Noronha et al., 2001). For a recent review of these nuclear importation mechanisms (Suzuki and Craigie, 2007). It has also been demonstrated that a plurality of proteins of the nucleoplasmic face of the nuclear envelope, including emerin, mutated into Emery-Dreiffus muscular dystrophy, are essential for penetration of the AIDS virus into the nucleoplasm and for the infection of cells that do not divide (Jacque and Stevenson, 2006).

The term genetic laminopathy therefore covers the pathologies resulting from mutations in the genes coding for the lamins, very specifically LMNA coding for lamins A and C, but also those caused by mutations of associated proteins, including those participating in lamin maturation.

The abnormalities induced by PIs at the level of the nuclear matrix therefore represent an acquired and iatrogenic laminopathy. Whether they are genetic or acquired, these abnormalities in the nuclear matrix result in genomic instability and cell aging (Mehta et al., 2007; Oberdoerffer and Sinclair, 2007).

4. The "Telomeric" Theory of Aging

Cell aging is controlled by a "clock" measuring the length of telomeres, which are shortened in each mitosis, a phenomenon that can be counterbalanced by the activity of the catalytic telomerase subunit (Gilson and Geli, 2007; Stewart and Weinberg, 2006).

Before the appearance of quantitative PCR, which enables direct measurement of telomere length in particular in mononucleated blood cells (Cawthon, 2002; Gil and Coetzer, 2004; Njajou et al., 2007), the measurement of telomerase activity (TRAP assay) was performed on cells of patients treated with antiretrovirals, with variable results, in particular depending on the T-lymphocyte subtype analyzed (Effros, 2000).

The NRTIs inhibit telomerase activity (Olivero, 2007; Yamaguchi et al., 2001).

Abnormalities in lamin A cause a reduction in telomerase activity, resulting in accelerated telomere shortening. These effects are observed in the cells of patients with progeria, whether or not the cells had been transfected to overexpress the catalytic telomerase subunit (Wallis et al., 2004). Comparable results were obtained in fibroblasts of healthy subjects overexpressing, after transfection, lamin A, normal, mutated or deleted, as in progeria (Huang et al., 2008). The nuclear matrix and the proteins of the nuclear envelope associated with it at the level of the lamina therefore directly or indirectly control telomerase activity (Pandita et al., 2007).

5. Certain Transcription Regulation Factors, in Particular p53 and NF-$_k$B, are Involved in Aging or Regulation Thereof.

Two families of proteins, p53 (Zafon, 2007) and NF-$_K$B (Hayden and Ghosh, 2004), control the transcription of a large number of genes and are involved in the aging phenomenon. These proteins are also involved in the mechanisms described in the other theories of aging and are related to one another.

Next to its well-characterized functions in the control of the cell cycle, the stress response, oncogenesis, and DNA lesion repair (Fuster et al., 2007; Helton and Chen, 2007; Sengupta and Harris, 2005), p53 is involved in cell aging (see, for example: (Bauer and Helfand, 2006; Ben-Porath and Weinberg, 2005; Papazoglu and Mills, 2007; Sharpless and DePinho, 2002; Tyner et al., 2002). The protein p53 is also involved in the abnormalities induced by laminopathies (Varela et al., 2005), in the functioning of helicase, the mutation of which is responsible for Werner syndrome (Brosh et al., 2001; Sommers et al., 2005), telomere regulation (Wynford-Thomas, 1996), and control of mitochondrial respiration (Matoba et al., 2006) independently of the role of p53 in the activation of apoptosis by its interaction with apoptogenic molecules of the outer membrane (Manfredi, 2003; Mihara et al., 2003; Moll et al., 2005). p53 also regulates the "insulin-IGF1-klotho" metabolic pathway (see below).

NF-$_\kappa$B is also involved in many metabolic pathways. Its inactivation by RNA interference in fibroblasts in culture protects them from aging (Hardy et al., 2005).

Similarly, the blockage that can be induced by the expression of NF-$_\kappa$B in mouse epidermal cells slows their aging via variations in the expression of numerous genes analyzed by microarray (Adler et al., 2007).

6. The "Metabolic" Theory of Aging Via Caloric Restriction and the Signaling Pathways of Insulin, IGF1 and the Klotho Hormone Links the Plasma Membrane, the Nucleus and the Mitochondria Caloric restriction increases the lifespan of rodents (Borone and Guarente, 2005). It activates deacetylase sirtuin, which targets histones (with remodeling of the chromatin) (Vijg and Suh, 2006), numerous other nuclear proteins (transcription factors including p53, proteins involved in DNA repair, etc.) as well as cytosolic (tubulin) and mitochondrial proteins (Guarente and Picard, 2005; North and Verdin, 2004; Porcu and Chiarugi, 2005).

Caloric restriction causes biogenesis of mitochondria via the expression of endothelial NO-synthase, eNOS (Nisoli and Carruba, 2006; Nisoli et al., 2005), resulting in an increase in ROS production (Gredilla and Barja, 2005). The insulin and IGF signaling pathways, involved in aging (Bartke, 2005; Russell and Kahn, 2007) are inhibited by caloric restriction (Holzenberger et al., 2004; Masoro, 2004).

Caloric restriction also inhibits the signaling pathways regulated by the klotho hormone (Kurosu et al., 2005; Unger, 2006), of which mutations are accompanied by premature aging in the mouse (Kuro-o et al., 1997). Klotho is a regulator of the response induced by the FGF-receptor (Kurosu et al., 2006). The mutations of klotho and FGF-23 induce the same premature aging phenotype, which is known to be caused by hypervitaminosis D and which is corrected by the deletion of a gene increasing the effect of vitamin D (Razzaque and Lanske, 2006). Klotho also blocks the response of Wnt receptors (Liu et al., 2007a), which shows the diversity of the metabolic pathways involved in aging. Finally, insulin stimulates, via phosphatidyl-inositol 3 kinase, the cleavage of the transmembrane precursor of klotho by metalloproteases of the ADAM family and the release of klotho into the extracellular medium (Chen et al., 2007). The protein p53 is also involved in the regulation of these metabolic pathways (Campisi, 2004; de Oliveira, 2006; Kim et al., 2007; Schmid et al., 2007).

The protein p66$^{shc}$ represents one of the communication signals between the plasma membrane receptors for insulin and for IGF1, the nucleus and the mitochondria (Martin and Friedman, 2004). KO p66$^{shc-/-}$ mice show high resistance to stress and an increase in their lifespan (Migliaccio et al., 1999). P66$^{shc}$ is a target of p53, localized in the mitochondria of which it controls the metabolism and ROS production (Migliaccio et al., 2006; Nemoto et al., 2006; Orsini et al., 2004; Trinei et al., 2002). A deletion of p66$^{shc}$ inhibits aging of cardiac stem cells and prevents cardiac accidents, two phenomena induced by diabetes (Rota et al., 2006). P66$^{shc}$ is also a redox enzyme. In response to cell stress, p6$^{shc}$ is imported into the mitochondria and is localized in the intermembrane space where it synthesizes $H_2O_2$ (i.e. 30% cellular $H_2O_2$, with the rest being produced by peroxisome) using electrons transferred by the cytochromes C (Giorgio et al., 2005). $H_2O_2$ may represent an intracellular signal for lifespan regulation (Giorio et al., 2007).

DESCRIPTION OF THE INVENTION

After lengthy research, the inventors showed that the association of a hydroxymethylglutaryl-coenzyme A reductase inhibitor (statin family) and a farnesyl-pyrophosphate synthase inhibitor (amino-biphosphonate family, NBP), or one of their physiologically acceptable salts, is an effective treatment in situations, pathological or not, associated with the accumulation and/or the persistence, in the cells, of prenylated proteins, in the sense that it acts on the entire protein prenylation pathway, at C15 and at C20, or in non-characterized forms. The inventors also observed that the association of a hydroxymethylglutaryl-coenzyme A (HMG-CoA) reductase inhibitor and a farnesyl-pyrophosphate synthase inhibitor has an additive effect in the restoration of the normal phenotype in fibroblasts of patients with Progeria. The effect of the association is clearly superior to the effect of one or the other of the inhibitors used individually (Varela et al. 2008 (54 bis)). The use of the association on cells of patients with Progeria leads to an inhibition in the prenylation of proteins, and therefore the appearance of non-farnesylated prelamin A and the improvement of nuclear symptoms and the partial correction of anomalies of DNA repartition. The prenylation inhibition is also observed in mice model for restrictive dermopathy and partially restore the mice lifespan (Varela et al. 2008 (54 bis)). Antiretroviral treatments target a plurality of metabolic pathways and a plurality of cell compartments, the cytosol, the nucleoplasm and the mitochondria.

The side effects of these treatments reproduce some of the clinical and biological signs observed in patients with genetic laminopathies caused by mutations in the LMNA gene or in the ZMPSTE24 gene. The common point between these mutations is that they preserve the farnesyl group bound to lamin A or to prelamin A. This farnesyl group anchors the lamin A to the nucleoplasmic face of the nuclear envelope at the level of the lamina, while the rest of the nucleoplasm is free of soluble lamin A.

These two abnormalities in the distribution of lamin A cause deleterious consequences at the level of a number of nuclear metabolic pathways (DNA replication and repair, gene transcription, telomere shortening, etc.), and also have deleterious consequences in other cell compartments, including the mitochondria. The general dysfunction of the cell causes accelerated aging and a reduced lifespan thereof.

A family of retroviral treatments, the protease inhibitors, inhibit ZMPSTE24, block the maturation of prelamin A and cause the persistence in the cell of farnesylated prelamin A. The appended FIG. 9 schematically shows the aging theory developed by the present inventors and based on abnormalities in the maturation of prelamin A and their functional consequences.

In addition, the indirect effects of the viral protease inhibitors on mitochondria, a second family of antiretroviral drugs, the viral nucleotide reverse transcriptase inhibitors, directly disrupt the mitochondria, an organelle of which abnormalities of its functioning are known to be associated with aging.

The objective is therefore to analyze the mechanisms by which these two types of antiretroviral treatment cause accelerated aging in patients infected with the AIDS virus and to verify that these mechanisms are comparable to those causing accelerated aging in patients with genetic laminopathy.

The present inventors deduced that the side effects described above of the antiretroviral treatments can be minimized owing to a composition including or a treatment combining:
- at least one hydroxymethylglutaryl-coenzyme A (HMG-CoA) reductase inhibitor or one of its physiologically acceptable salts, and
- at least one farnesyl-pyrophosphate synthase inhibitor or one of its physiologically acceptable salts. This invention therefore relates to an anti-HIV composition including at least one hydroxymethylglutaryl-coenzyme A (HMG-CoA) reductase inhibitor, at least one farnesyl-pyrophosphate synthase inhibitor, or one of their physiologically acceptable salts, and an anti-HIV agent.

This composition can be intended, for example, for treating situations, pathological or not, associated with the accumulation and/or persistence in the cells of prenylated proteins. In particular, according to the invention, this composition is useful in the treatment of an HIV-infected patient.

This invention also relates to a composition according to the invention in which the anti-HIV agent is an antiretroviral agent or a mixture of antiretroviral agents.

This invention also relates to a composition according to the invention in which the anti-HIV agent is a protease inhibitor or a reverse transcriptase inhibitor.

This invention also relates to a composition according to the invention in which the anti-HIV agent is a protease inhibitor chosen from the group including fosamprenavir, lopinavir, ritonavir, amprenavir, atazanavir and indinavir.

This invention also relates to a composition according to the invention in which the anti-HIV agent is a reverse transcriptase inhibitor chosen from the group including zidovudine, lamivudine, didanosine and epzicom.

In the composition of this invention, the anti-HIV agent can also be an association of one or more antiproteases of the virus and/or one or more reverse transcriptase inhibitors of the virus and/or one or more inhibitors of the entrance of the virus into the cells and/or one or more integrase inhibitors and/or any other treatment having an antiviral effect, in particular any treatment recognized by the national and/or international regulatory institutions and the scientific community.

This invention also relates to a composition according to the invention in which compounds are used that are both hydroxymethylglutaryl-coenzyme A (HMG-CoA) reductase inhibitors and farnesyl-pyrophosphate synthase inhibitors. Very specifically, the composition according to the invention is intended to treat an HIV-infected patient developing side effects associated with the accumulation and/or persistence of progerin in the cells; even more specifically, the treatment of situations associated with the accumulation and/or persistence, in the cells, of farnesylated prelamin A, whether or not it is truncated or modified.

According to the invention, any farnesyl-pyrophosphate synthase inhibitor or one of its physiologically acceptable salts can be used in the preparation of the composition according to the invention.

The physiologically acceptable salts can be, for example, salts formed with hydrochloric, hydrobromic, nitric, sulfuric or phosphoric acid, carboxylic acids such as, for example, acetic, formic, propionic, benzoic, maleic, fumaric, succinic, tartric, citric, oxalic, glyoxylic, aspartic acid, sulfonic alkanes acid such as sulfonic methane or ethane acids, and arylsulfonic alkanes such as sulfonic benzene or paratoluene acid.

In particular, the farnesyl-pyrophosphate synthase inhibitor can be one of the members of the family of polyphosphonates, particularly aminobiphosphonates (NBP), or one of its physiologically acceptable salts.

Polyphosphonates are synthetic molecules commonly used in the treatment of osteoporosis and bone regeneration.

The term phosphonate applies to molecules very similar to phosphate:

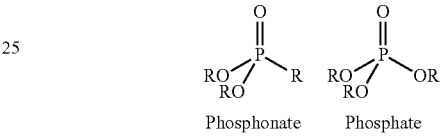

Phosphonate   Phosphate

The core of the biphosphonates (BP) is equivalent to a P—O—P bond as in ATP, for example, but in which the oxygen is replaced by a carbon. This confers a very specific stability on these molecules.

A simple biphosphonate would be equivalent to ADP, with the 2 phosphate groups ($O_3P^-$) being replaced by the biphosphonate group.

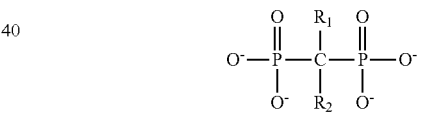

The central carbon, unlike the oxygen of the phosphates, can again be involved in 2 bonds, and it is the nature of the groups grafted onto this carbon that constitutes the specificity of the biphosphonates.

When the "lateral" chains (R1 and R2) comprise an amine function (NH), or more generally one or more nitrogen atoms, we refer to amino-biphosphonate, or NBP.

Of course, other substituents can be bound to oxygens. Pyrophosphoric acid, or pyrophosphate in solution (PPi)

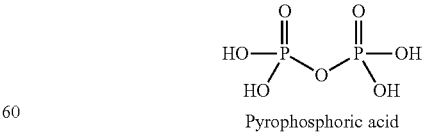

Pyrophosphoric acid is used in numerous metabolic reactions as a substrate transporter, and it is restored at the end of the reaction. One of the metabolic pathways using molecules coupled to pyrophosphate is that of protein prenylation. The grafting of an isopentenyl-PP (C5-based unit) onto a geranyl-PP (C10)

to give farnesyl-PP, a reaction catalyzed by the farnesyl-pyrophosphate synthase (FPS) enzyme, releases a PPi.

It is this step that is specifically inhibited by the NBPs.

In this regard, and as an example, the aminobiphosphonate (farnesyl-pyrophosphate synthase inhibitor) can be chosen from:

alendronic acid or its ionic form, alendronate;
clodronic acid or its ionic form, clodronate;
etidronic acid or its ionic form, etidronate;
ibandronic acid or its ionic form, ibandronate;
medronic acid or its ionic form, medronate;
neridronic acid or its ionic form, neridronate;
olpadronic acid or its ionic form, olpadronate;
pamidronic acid or its ionic form, pamidronate;
risedronic acid or its ionic form, risedronate;
tiludronic acid or its ionic form, tiludronate;
zoledronic acid or its ionic form, zoledronate;
4-N,N-dimethylaminomethane diphosphonic acid or its ionic form, dimethylaminomethanediphosphonate;
α-amino-(4-hydroxybenzylidene) diphosphonate.

Preferably, according to the invention, it is preferable to use zoledronic acid (also called zolendronic acid) or its ionic form, zoledronate (also called zolendronate). According to the invention, any HMG-CoA reductase inhibitor, or one of its physiologically acceptable salts, can be used in the preparation of the composition.

In particular, the HMG-CoA reductase inhibitor can be a molecule of the statin family, whether it is liposoluble or hydrosoluble, or one of its physiologically acceptable salts.

Statins have been identified in fungi. They have an inhibiting activity on HMG-CoA reductase, a key enzyme in the biosynthesis of cholesterol and steroids, which catalyze the reduction of hydroxymethylglutarate coupled to Coenzyme A in mevalonic acid (mevalonate in solution). This inhibition is ensured by their structural similarity with the hydroxymethylglutarate skeleton. The metabolic pathway involved is admittedly that of cholesterol biosynthesis, but it is also that of the synthesis of prenyl groups, polymers of the 5 isoprene carbon base unit used to modify around 300 proteins in the cells and attach a lipophilic tail, enabling in particular their anchoring in the membranes.

The main polyprenes, all from pyruvate and HMG-CoA, are geranyl (C10), farnesyl (C15) and geranyl-geranyl (C20).

All of the statins are globally hepatoselective, but all do not have the same mode of entry into the cells. Indeed, pravastatin and rosuvastatin are both hydrophilic, and therefore hydrosoluble, unlike all of the others, which are lipophilic, and therefore can diffuse freely through the plasma membranes (lipid bilayers), which undoubtedly explains their higher toxicity. The hydrosoluble statins need a specific transporter in order to enter the cell, *Organic Anion Transporter* 3, or OAT3, or SLC22A8 (Takedaa & al. 2004 (46)).

They are commonly used to treat hypercholesterolemia, and their side effects, which are rare, have been characterised in detail. These are in particular cases of rhabdomyolysis (1 to 7% of cases according to the molecule used, Evans & al. 2002 (12)), of which the early signs, muscle pain in the patient being treated, results in immediate discontinuation of the treatment.

In this regard, and as an example, a statin can be chosen from atorvastatin, simvastatin, pravastatin, rivastatin, mevastatin (or compactin), fluindostatin, velostatin, fluvastatin, dalvastatin, cerivastatin, pentostatin, rosuvastatin, lovastatin, pitavastatin, or one of their physiologically acceptable salts.

Lovastatin, pravastatin and simvastatin are molecules derived from fungal metabolites, while the others (atorvastatin, cerivastatin, fluvastatin, pitavastatin and rosuvastatin) are entirely synthetic. Preferably, according to the invention, pravastatin, a semi-natural, hydrosoluble statin, is used.

Of course, it is possible according to the invention to use one, two or more farnesyl-pyrophosphate synthase inhibitors associated with one, two or more HMG-CoA reductase inhibitors.

According to a specific form of the invention, the composition can be intended both for the treatment of an HIV-infected patient and the treatment of side effects of the anti-HIV treatment, for example skin aging, body or head hair loss, osteoporosis and lipodystrophy.

According to the invention, the farnesyl-pyrophosphate synthase inhibitor and the HMG-CoA reductase inhibitor are advantageously present in the composition at physiologically effective doses.

Generally, the amounts to be administered can be adapted according to the patient, the pathology, the mode of administration, and so on. It is understood that repeated uses are possible, optionally in combination with other active ingredients or any carrier.

In general, the daily dose of inhibitors will be the minimum dose needed to obtain the desired effect.

According to the invention, the hydroxymethyl-glutaryl-coenzyme A (HMG-CoA) reductase inhibitor, the farnesyl-pyrophosphate synthase inhibitor, and the anti-HIV agent can be used in the composition, in a mixture with one or more inert, i.e. physiologically inactive and non-toxic, excipients or carriers. It is possible to cite, for example, the ingredients normally used in drugs intended to treat HIV-infected patients and accompanying the anti-HIV agent.

The composition of this invention can also include at least one other active ingredient, particularly another therapeutically active ingredient, for example for a simultaneous or separate use or a use spread out over time according to the galenic formulation used. This other ingredient can be, for example, an active ingredient used, for example, in the treatment of opportunistic diseases that can develop in an HIV-infected patient.

The composition of this invention is a composition that can be used both to treat an HIV-infected patient and to prevent and/or treat skin disorders caused by the use of the anti-HIV agent. This composition can be used as part of a multitherapy for an HIV-infected patient. The anti-HIV agent can be a single agent or multiple agents (a mixture of a plurality of anti-HIV agents). In the case of multitherapy (for example, di-, tri- or quadritherapy), the mixture of inhibitors can accompany one or more of the anti-HIV agents.

The anti-HIV agent can also be an association of one or more antiproteases of the virus and/or one or more reverse transcriptase inhibitors of the virus and/or one or more inhibitors of the entry of the virus into the cells and/or one or more integrase inhibitors and/or any other treatment having an antiviral effect, in particular any treatment recognized by the national and/or international regulatory institutions and the scientific community.

This invention therefore also relates to a process for treating an HIV-infected patient, including the administration of a composition according to the invention. The composition of the invention is as defined above.

According to the invention, the administration can be performed according to any of the routes known to a person skilled in the art for administering an anti-HIV composition. It can be, for example, an oral administration or an injection.

As indicated above, the administered dose of the composition of the invention depends upon the patient's needs and is also determined by taking into account what is physiologically acceptable by the patient.

The quantity of inhibitors in the composition of this invention can be such that it enables, as an example, the administration of a dose of hydroxymethylglutaryl-coenzyme A (HMG-CoA) reductase inhibitor of 0.01 to 2 mg/kg of body weight and a dose of farnesyl-pyrophosphate synthase inhibitor of 0.01 to 40 mg/kg of body weight.

According to the invention, as an example, in the composition of the invention, the ratio of farnesyl-pyrophosphate synthase inhibitor to hydroxymethyl glutaryl coenzyme A reductase inhibitor, or one of their physiologically acceptable salts, can be between 0.01 and 0.2, and preferably 0.05 to 0.35.

The quantity of anti-HIV agent in the composition of this invention is conventionally determined according to the current knowledge of a person skilled in the art in the treatment of HIV-infected patients. It can be chosen, for example, from those conventionally used in HIV-infected patients.

Examples of anti-HIV agent concentrations for each of the anti-HIV agent examples described in this document and each of the mixtures or associations of anti-HIV agents described in this document are provided in the VIDAL Dictionary (registered trademark), for example Edition 2007. The concentrations indicated in this Dictionary are also those authorized for humans.

This invention also relates to a process for treating side effects of premature aging and/or lipodystrophy caused in a patient undergoing an anti-HIV treatment, which process includes the administration of a mixture including at least one hydroxymethylglutaryl-coenzyme A (HMG-CoA) reductase inhibitor and at least one farnesyl-pyrophosphate synthase inhibitor.

The conditions, quantities and routes of administration can be as described in this document, for example above. The anti-HIV agent is, for example, an anti-HIV agent or an association as defined above.

This invention relates in general to an application of the mixture of inhibitors mentioned above as an adjuvant for treatments having an iatrogenic effect, for example premature aging, including, for example, the application of an "adjuvant to the anti-HIV therapies comprising at least one anti-protease" in particular causing this iatrogenic effect. Thus, any treatment causing the side effects cited in this document is concerned by this invention.

This invention also relates to a process for treating an HIV-infected patient including, in any order, the following steps:
administration of a mixture including at least one hydroxymethylglutaryl-coenzyme A (HMG-CoA) reductase inhibitor and at least one farnesyl-pyrophosphate synthase inhibitor,
administration of an anti-HIV agent.
in which the administrations are concomitant, successive or alternative.

According to the invention, said mixture and said anti-HIV agent can be co-administered. This involves the process of the invention defined above.

According to the invention, the anti-HIV agent can be as defined above.

According to the invention, at least one of the administrations can be performed orally or by injection. The two administrations can be performed in the same way or differently.

In other words, even if in this description we refer to a composition, it is understood that each compounds of the composition may be administered concomitantly with the other compounds (for example in a single composition or in two compositions or in three compositions, each of these compositions including one or several of the above mentioned compound, the mode of administration of each compounds or composition(s) may be identical or different), or independently from one another, for example successively, for example independent administration of a hydroxymethylglutaryl-coenzyme A (HMG-CoA) reductase inhibitor, independent administration of at least one farnesyl-pyrophosphate synthase inhibitor and independent administration of an anti-HIV agent, these administrations are performed on the same patient, concomitantly or successively or alternatively, in the above mentioned order or another order. These different administrations may be performed independently from each other or in a combined manner (composition or co-administration), by an identical or different mode of administration (injection, ingestion, topical application, etc.), one or several times daily, for one or several successive, or not, days.

According to the invention, the administration of said mixture of inhibitors can be performed, for example, with a dose of the hydroxymethylglutaryl-coenzyme A (HMG-CoA) reductase inhibitor of 0.01 to 2 mg/kg of body weight and with a dose of the farnesyl-pyrophosphate synthase inhibitor of 0.01 to 40 mg/kg of body weight.

The administration of the anti-HIV agent can be performed as indicated above.

As an example only, dosages are described in the following table for the implementation of one or the other of the processes of the invention defined above. Examples of amounts of inhibitors and anti-HIV agent in a composition according to this invention can be derived from this table.

|  | Dosage 1 | Dosage 2 | Route | Wide range anti-HIV |
|---|---|---|---|---|
| Pravastatin | 10 to 20 mg/d | 20 to 40 mg/d | Oral | 1 to 100 mg/d |
| Simvastatin |  | 10 mg/d | 10 to 40 mg/d Oral | 1 to 100 mg/d |
| Alendronate |  | 10 mg/d | 20 to 40 mg/d Oral | 1 to 50 mg/d |
| Zolendronate | 4 mg/3 s | or 0.20 mg/d | IV | 0.01 to 0.50 mg/d |
| Pamidronate | 15 to 90 mg/d | — | IV | 1 to 100 mg/d |
| Clodronate | 1600 mg/ | two times | Oral | 100 mg to 2 g/d |

"IV" means intravenously
"d" means "day".
Dose/d = dose/day.

According to the invention, the dosages concerning the anti-HIV agent that can be used to implement this invention may be known to a person skilled in the art. They can be, for example the dosages described in the VIDAL Dictionary (registered trademark), for example in Edition 2007. For each of the examples of anti-HIV agent described above and each of the mixtures or associations of anti-HIV agents described above, one will also find, in the VIDAL Dictionary (registered trademark), for example Edition 2007, dosages that can be used to implement this invention.

Other advantages may also appear to a person skilled in the art from the examples below, provided for illustrative purposes and shown in the appended figures.

EXAMPLES

Example 1

Figure 1:
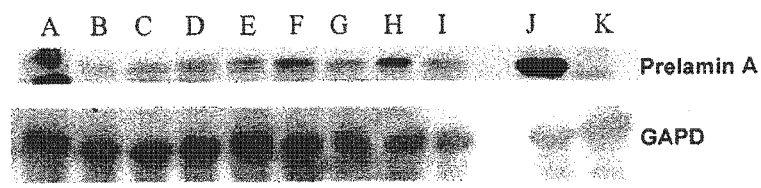
FIG. 1 shows the results obtained with a Western Blot on "normal" control fibroblasts treated with increasing doses of a hydrosoluble statin (pravastatin P, 20 to 100 µM), and an aminobiphosphonate (NBP, zoledronate Z, 20 to 100 µM) (tracks A to I, respectively P20/Z20, P20/Z60, P20/Z100, P60/Z20, P60/Z60, P60/Z100, P100/Z20, P100/Z60, P100/Z100). Track J is a positive test for the presence of prelamin A (fibroblasts of DR patients), and track K is the negative test, treated with the solvent alone (PBS).

Additive Effect of the Association of a Hydrosoluble Hydroxymethylglutaryl-Coenzyme a (HMG-CoA) Reductase Inhibitor (a Hydrosoluble Statin: Pravastatin) and a Farnesyl-Pyrophosphate Synthase Inhibitor (an Aminobiphosphonate: Zoledronate) on Normal and Progeroid Cell Cultures A. Protocols A.1 Cells and Cell Culture The cell lines are either control fibroblasts AG16409 from the Coriell Institute or fibroblasts from biopsies of patients with restrictive dermopathy. They are cultivated at 37° C. under 5% $CO_2$ in room P2.

The usual complete culture medium is:
RPMI (Invitrogen) complemented with
Fetal bovine serum 20% (Invitrogen)
L-Glutamine 200 mM (Invitrogen)
Mixture of Penicillin/Streptomycin/Fungizone 1× (Stock 100×, Cambrex)

A.2 Cell Harvesting

The harvesting of cells is performed by trypsinization as follows (protocol for a large flask, 75 cm$^2$, BD Falcon):

The medium is suctioned;
The cells are washed with 10 ml of PBS 1× (Invitrogen);
5 ml of a solution of Trypsin/EDTA 1× (Cambrex) are added;
The flask is incubated for around 6 minutes at 37° C., the time that it takes for the cells to detach;
The trypsin is inhibited by dilution in 15 ml of complete medium;
The cells are pelleted by centrifugation for 10 minutes at 1000 rpm at 16° C.
The pellet is resuspended in 2 ml of PBS 1× and re-centrifuged under the same conditions.

The cells obtained are either frozen for later use or are subcultured from this washed pellet.

A.3 Treatments

The pravastatin solution (hydrosoluble statin) used is prepared as follows:

40 mg of pravastatin (Sigma Aldrich, P4498) are placed in sterile water to form a 10 mM stock solution.

The final concentrations tested were 500 nM, 1, 5, 50 and 100 μM, obtained by diluting the stock solution in the complete medium.

The zoledronate solution (NBP) used is prepared as follows:

A (1-hydroxy-2-imidazol-1-yl-1-phosphono-ethyl) phosphonic acid stock solution (0.8 mg/ml, Novartis) is adjusted to a concentration of 2 mM.

The final concentrations tested were 500 nM, 1, 5, 50 and 100 μM, obtained by diluting the stock solution in the complete medium.

A.4 Western Blot

A.4.1 Preparation of Cells

For a Western blot experiment, the cells are treated as follows:

Around 7.5×10$^5$ cells are seeded in a large flask and cultivated under the conditions above until close to confluency (4 days).

After 4 days, the cells are washed with PBS 1× and placed in the complete medium substituted with the treatment.

The cells are incubated for the treatment time (6 to 72 hours, sequentially or simultaneously) in the incubator at 37° C.

After the treatment, the cells are trypsinized (protocol above) and the pellet obtained is stored at −80° C. until protein extraction.

A.4.2 Protein Extraction for Western Blot

The cell pellet is placed in 300 μl of lysis buffer

| | |
|---|---|
| Triton X100 | 1% |
| SDS | 0.1% |
| Sodium deoxycholate | 0.5% |
| NaCl | 50 mM |
| EDTA | 1 mM |
| TrisHCl pH 7.4 | 20 mM |
| Protease inhibitor (Roche 11697498001) | 1 tablet for 50 ml |

Extemporaneously, the following are added:

| | |
|---|---|
| Sodium orthovanadate | 1 mM |
| PMSF | 1 mM |

The cells are exposed to sonication 2 times for 30 seconds (Brandson Sonifier Cell Disruptor B15).

The cell debris is centrifuged for 10 minutes at 10,000 rpm at 4° C.

The protein supernatant is preserved at −80° C. until its use.

The protein assay is performed upon thawing.

A.4.3 Western Blot

Gel

An 8% acrylamide gel is conventionally used to detect the various forms of lamins A/C.

| | |
|---|---|
| Acrylamide/bisacrylamide 37/1 | 8% |
| TrisHCl pH 8.8 | 375 mM |
| SDS | 0.1% |
| APS | 0.1% |
| TEMED | 0.01% |

A concentration gel is poured over the separation gel.

| | |
|---|---|
| Acrylamide/bisacrylamide 37.5/1 | 3% |
| TrisHCl pH 6.8 | 375 mM |
| SDS | 0.1% |
| APS | 0.1% |
| TEMED | 0.01% |

The protein concentration of the samples is assayed, and fractions are adjusted to 50 μg per tube in the lysis buffer in a qsf 15 μl.

5 μl of loading buffer are added to each sample.

| | |
|---|---|
| SDS | 4% |
| TrisHCl pH6.8 | 100 mM |
| Glycerol | 20% |
| β-mercaptoethanol | 20% |
| Bromophenol blue | Traces |

The samples are denatured by heating for 5 minutes at 95° C. and deposited in wells.

The migration takes place at 50, then 100 volts, in a buffer:

| | |
|---|---|
| Tris-Base | 0.3% |
| Glycine | 1.44% |
| SDS | 0.1% |

Transfer

The transfer membrane (Hybon P, Amersham Bioscineces) is prepared by soaking in ethanol, followed by a 5-minute bath in sterile water, and 10 minutes in the transfer buffer:

| | |
|---|---|
| Tris-Base | 12 mM |
| Glycine | 96 mM |
| Ethanol | 20% |

The gel is humidified for 20 minutes in the transfer buffer, then the sandwich is assembled (Miniprotean system, Biorad).

The transfer generally takes place overnight, in a cold chamber, at 10 volts.

The membrane is rinsed in PBS 1×, preserved in a humid environment, and used as is for detection.

Detection

The membrane is incubated for 1 hour at room temperature in a saturation solution:

| | |
|---|---|
| Casein | 10% |
| Tween 20 | 0.1% |
| PBS | 1X |

It is rinsed 2 times for 10 minutes in the washing buffer (Tween 20 0.1%/PBS 1×).

The primary antibody is diluted in the saturation buffer (details and dilution, see immunolabeling below).

The membrane is incubated with the primary antibodies for 1 hour at room temperature while stirring.

It is then rinsed 3 times with the washing buffer, then washed 3 times for 15 minutes with the same buffer.

The secondary antibody (system coupled to peroxidase, Jackson Immunoresearch) is diluted to 1/10000 in the saturation buffer.

The membrane is incubated with this solution for 30 to 45 minutes at room temperature while stirring.

It is then rinsed 3 times with the washing buffer, then washed 3 times for 15 minutes with the same buffer.

The detection is performed with the ECL Plus Western Blotting System kit of Amersham Bioscience, according to the manufacturer's instructions.

After detection, the membrane is exposed on a Biomax MR film (Kodak), for the amount of time necessary to have a satisfactory signal.

A.5 Immunolabeling

A.5.1 Cell Preparation

A cell culture is trypsinized, and the cells are counted on a Neubauer cytometer.

Labtech culture wells (Nunc, ref. 177399) are seeded in an amount of $5 \times 10^4$ cells per well.

The complete culture medium is supplemented by the treatment(s) (statin, NBP, both), and the cells are cultivated for the ad hoc time.

The culture medium is then suctioned, and the wells are disassembled.

The slides are washed in PBS 1×.

The cells are fixed in a paraformaldehyde 4% solution (in PBS) for 10 minutes at room temperature.

A 10 minute washing in PBS 1× is performed.

The cells are dehydrated by a series of 3 minute baths in solutions with increasing ethanol percentages (70, 90, 100%, with the last bath being repeated).

After drying, the slides are stored at −80° C. until use.

A.5.2 Labeling

After thawing, the cells are incubated for 5 minutes at room temperature in a humidity chamber in 50 μl of permeabilization solution:

| | |
|---|---|
| PBS | 1X |
| Triton X100 | 0.5% |
| RNS(Rabbit Normal Serum, Vector S5000) | 5% |
| Protease Inhibitor (Roche 11697498001) | 1 tablet for 50 ml |

3 pre-incubation baths, each for 15 minutes, are performed in 50 μl of the incubation solution:

| | |
|---|---|
| PBS | 1X |
| RNS | 5% |
| Protease Inhibitor (Roche 11697498001) | 1 tablet for 50 ml |

The primary antibody is diluted to 1/100 in 50 μl of incubation solution and placed in contact with the cells for 1 hour at room temperature in a humidity chamber.

The primary antibodies used are of two types:

Mouse anti-lamin A/C (N-terminal side), clone 4A7, donated by G. Morris (Oswestry, UK)

Goat anti-prelamin A (C-terminal end 15 aa), product SC6214, Santa Cruz Biotchnology, Inc.

3 rinsings in 50 μl of PBS 1× are performed for 15 minutes each.

The incubation with the secondary antibody takes place for 1 hour in 50 ml of incubation solution at room temperature in a humidity chamber. The secondary antibodies are of two types:

Donkey anti-mouse, Jackson Immunoresearch, dilution to 1/100,

Donkey anti-goat, Jackson Immunoresearch, dilution to 1/200.

3 rinsings in 50 μl of PBS 1× are performed for 15 minutes each.

Incubation with 100 μl of DAPI 50 ng/ml solution (SERVA, ref. 18860) is performed for 15 minutes at room temperature in a humidity chamber.

3 rinsings in PBX 1× are performed in slide-holder tanks for 5 minutes each.

A final rinsing is performed for 5 minutes in a solution of Tween 20 at 0.1% in PBS.

A.5.3 Presentation

The cells are immersed in one drop of VectaShield (Vector), covered with an object-cover slide and observed under a fluorescence microscope (Leica DMR, Leica Microsystems), equipped with a coolSNAP camera (Princeton).

B. Results

B.1. Western Blot (FIG. 1)

"Normal" control fibroblasts were treated with a hydrosoluble statin (pravastatin P, 20 to 100 µM), and with an aminobiphosphonate (NBP zoledronate Z, 20 to 100 µM) in association (Tracks A to I, respectively P20/Z20, P20/Z60, P20/Z100, P60/Z20, P60/Z60, P60/Z100, P100/Z20, P100/Z60, P100/Z100). The Western blot shows the "appearance" of a band corresponding to the size of the non-mature prelamin A (non-truncated) as a function of the increase in concentration of the two molecules, confirming that farnesylation is necessary for maturation of lamin A. This result shows that the blockage of the farnesyl-PP synthesis at 2 points of the metabolic pathway is more effective than a blockage at only one point on the inhibition of the farnesylation of prelamin A, at least ex vivo.

Figure 2:
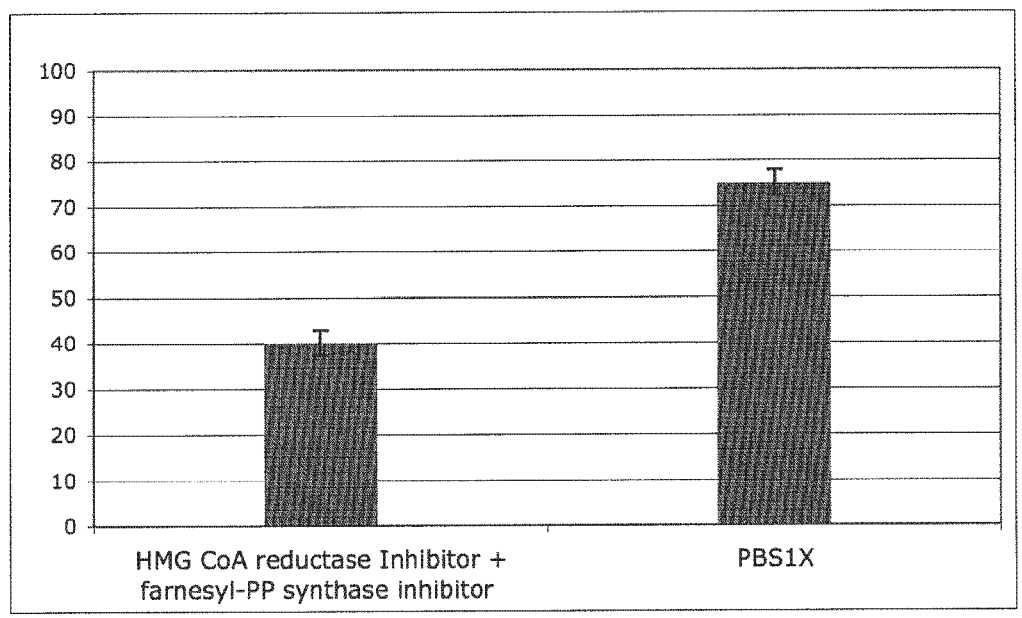
FIG. 2 shows the results obtained at effective doses of each of the products.

B.2 Response Dose and Time in Immunohistochemistry (FIG. 2)

Response dose and response time curves made it possible to determine maximum efficacy by measuring two parameters on healthy control cells, then on HGPS patient cells.

The most effective association of pravastatin (hydrosoluble)/zoledronate (NBP) was obtained for an administration of 1 µM of pravastatin over 24 hours, and zoledronate over 12 hours on the healthy cells. No toxicity was observed. On the HGPS cells (sells with nuclear abnormalities), using the same administration protocol, the number of "deformed" nuclei decreased from 75% to 40%. The prelamin A level obtained on healthy cells was measured. This measurement showed a maximal level.

Figure 3:
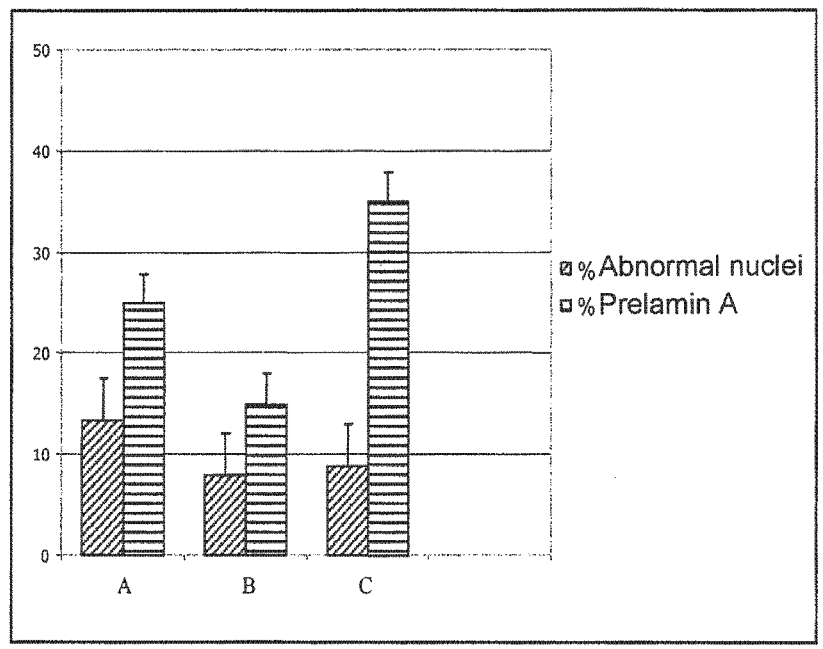
FIG. 3 shows the superior effect obtained with the administration of the two products together.

B.3 Effect of the Immunohistochemistry Treatment (FIG. 3)

The combined action of pravastatin and zoledronate, treatment: Pravastatin 100 µM for 12 hours, Zoledronate 20 µM for 6 hours, shows better efficacy, since the prelamin A level produced in healthy cells treated (estimated at 35%) is much higher in association than if the molecules are added alone (respectively 25% and 15%). Moreover, the rate of deformed nuclei (sign of toxicity on healthy cells) is minimal (below 10%), and below what it is on cells treated with pravastatin alone (around 12%).

Figure 4:
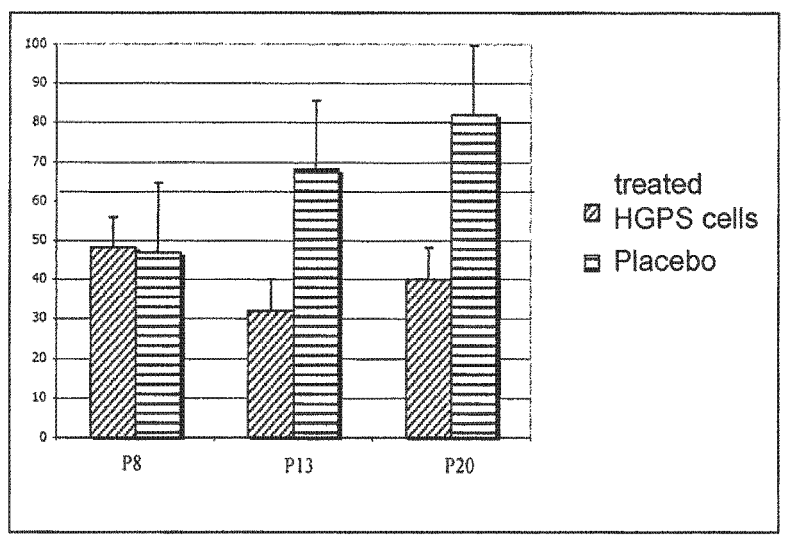
FIG. 4 shows the action of the association of the two products on aged cells.

B.4 Action on Aged Cells by Immunohistochemistry (FIG. 4)

As a function of the number of "passages" (number of cell subcultures), therefore the age of the cells, the proportion of abnormal nuclei increases. This characteristic is typical of non-treated HGPS cells. If HGPS cells are treated with Pravastatin 1 µM for 24 hours and Zoledronate 1 µM for 12 hours, this proportion is maintained, and even decreases slightly (less than 40% by comparison with more than 80% in cells treated with a placebo).

B.5 Conclusion

The pravastatin/zoledronate association is effective at doses for which almost no effect is observed when the molecules are administered separately.

The physiological effect of blocking the prenylation pathway is therefore obtained with doses much lower than those used in a single treatment in the articles published on cell cultures (Kusuyama & al., 2006 (27), 10 µM of pravastatin alone on vascular cell progenitors; Flint & al., 1997 (13), 25 µM of pravastatin alone on neonatal rat muscle cells).

Example 2

Effect of a Composition According to the Invention Including a Hydrosoluble Hydroxymethylglutaryl-Coenzyme a (HMG-CoA) Reductase Inhibitor and a Farnesyl-Pyrophosphate Synthase Inhibitor on the Division of Aged Human Fibroblasts and on Young Human Fibroblasts A. Example Objective In this example, the evaluation of the in vitro effect of a composition according to the invention including a hydrosoluble hydroxymethylglutaryl-coenzyme A (HMG-CoA) reductase inhibitor and a farnesyl-pyrophosphate synthase inhibitor on the rate of cell division (mitotic index) of fibroblasts was measured. A comparison of the effect of the composition on aged human fibroblasts with respect to young human fibroblasts was also performed. The number of active agents used in this experiment is four, and the products were used in pair combinations. The active agents used are:

A1: Zolendronate
A2: Alendronate
B1: Pravastatin
B2: Simvastatin

The specific associations that were used in this example are: A1B1, A1B2, A2B1, A2B2.

B. Protocol

In this example, two batches of fibroblasts, aged fibroblasts (batch no. 9052) and young fibroblasts (batch no. 7080) were placed in culture in a RPMI (Invitrogen) medium containing 10% fetal bovine serum without antibiotics for 24 hours after trypsinization of the dishes provided.

The various active agents were added at a final concentration of 1 µM, each for 24 hours (a 1000 dilution of a stock solution in water for compounds A1, A2 and B1, or in Ethanol 100% for compound B2, was produced).

The mitotic index was evaluated by incorporating Bromodeoxyuridine (BrdU) over 45 minutes after 24 hours of incubation of the cells with one of the active agent combinations. An immunohistochemical detection showed the cells in the DNA synthesis phase (pre-division cell).

Staining of the nuclei (genetic material) was performed by incorporating diamino-phenylindole (DAPI).

Six microscopic fields (OLYMPUS IX 70) were obtained, enabling the mitotic index to be measured by image analysis (OLYMPUS AnalySIS). The mitotic index corresponds to the ratio of the number of nuclei having incorporated BrdU over the number of nuclei having incorporated DAPI. An average index is statistically calculated with a standard deviation of between 0.005 and 0.061.

A bilateral Student test enabled the statistical significance of the results obtained to be measured.

C. Results

C.1 General Visual Observation of the Cells

These results show a very low division capacity among aged fibroblasts in the absence of any treatment, prior to the study.

The young fibroblasts showed a division capacity superior to that of the aged fibroblasts. The division capacity of aged fibroblasts was below 5%, while the division capacity of young fibroblasts was 15.6%. The difference in division capacity between the aged non-treated fibroblasts and the young non-treated fibroblasts was therefore equal to 3.

In this example, no toxicity was visually observed after 24 hours of incubation of the fibroblasts with the active agent combinations tested.

In this example, no toxic effect of ethanol (0.1% final) was observed after 24 hours of incubation.

D. Evaluation of the Mitotic Index (FIG. 5)

Figure 5:
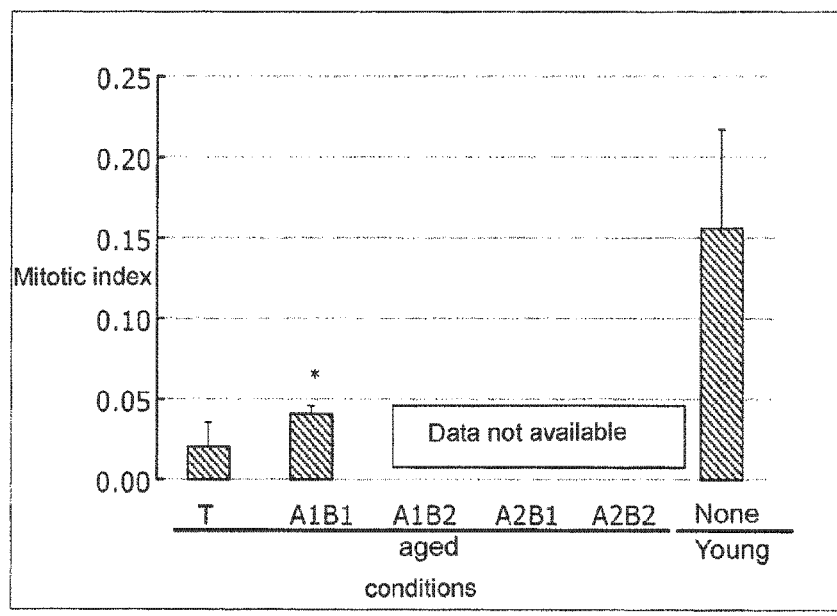
FIG. 5 shows the cell multiplication of fibroblasts by a measurement of the mitotic index as a function of cell culture conditions. The mitotic index corresponds to the ratio between the number of nuclei marked (entering the division process) with respect to the number of total nuclei of the field observed as a function of each treatment.
Figure 6:
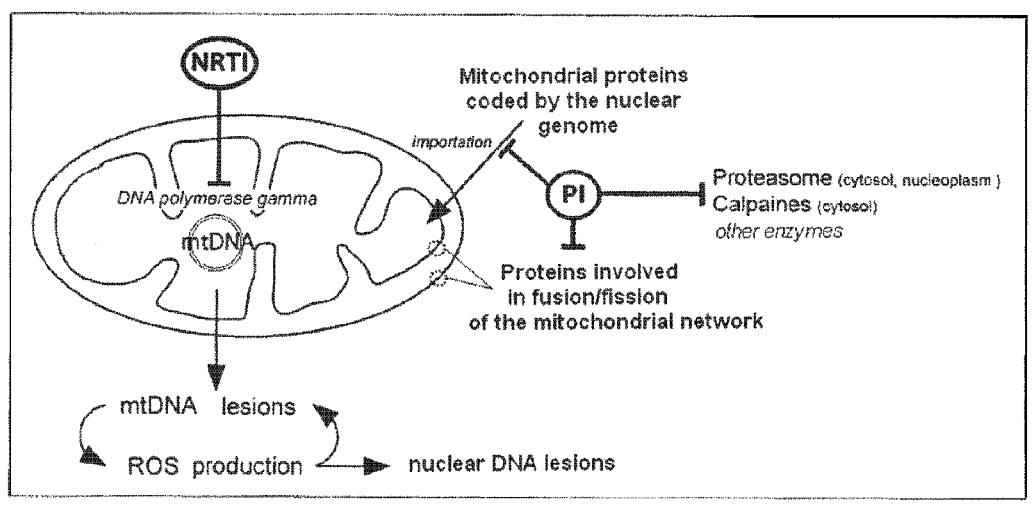
FIG. 6: Schematic representation of the mitochondrial theory of aging. The mitochondrial targets of the antiretroviral treatments. Legend: NRTI: nucleosides inhibitors of inverse transcriptase, PI: protease inhibitors, mtDNA: mitochondrial DNA and ROS: Reactive oxygen species
Figure 7:
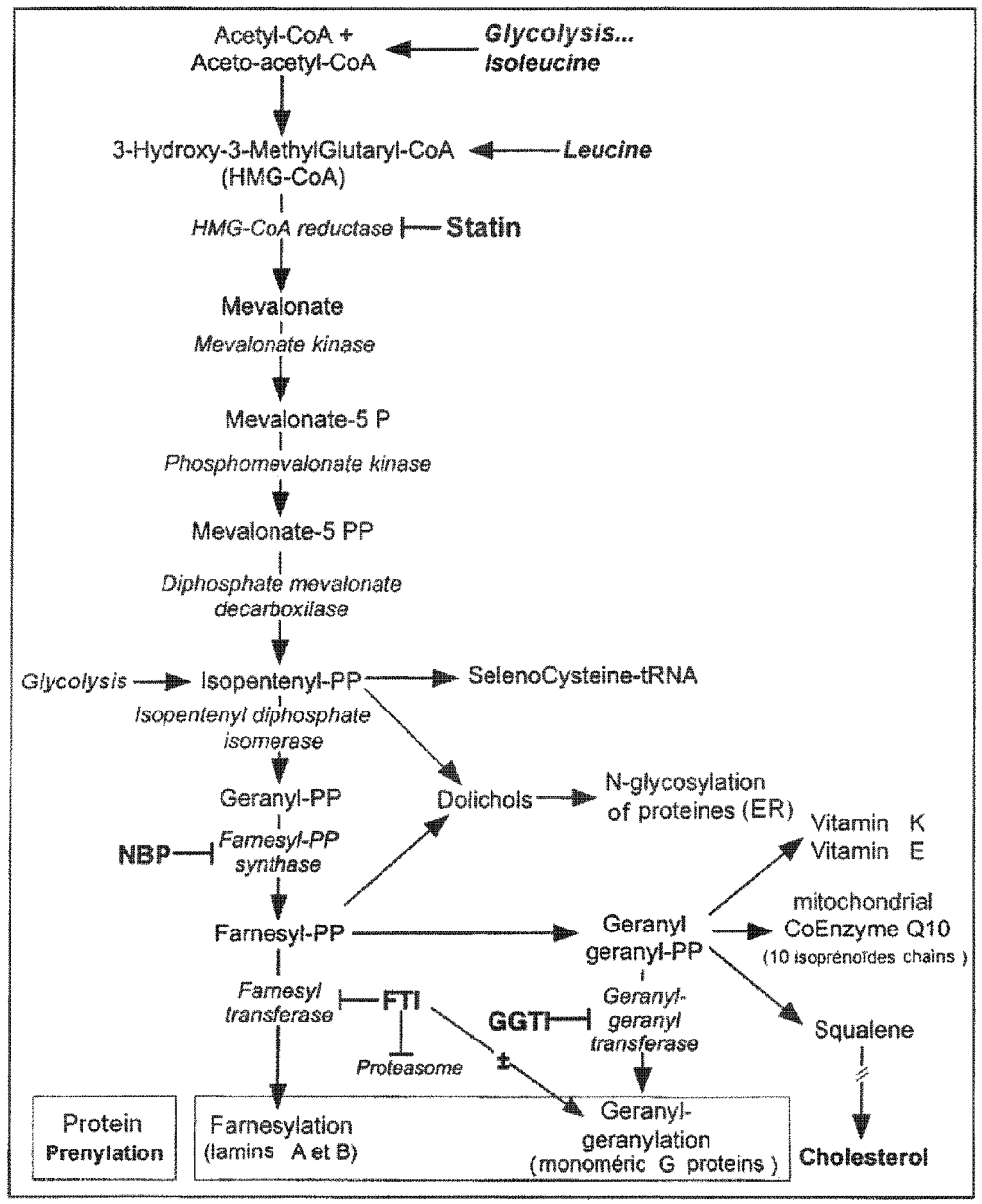
FIG. 7: Schematic representation of the biosynthetic pathway of isoprenoids and inhibitors thereof.
NBP: aminobiphosphonate
FTI: farnesyl-transferase inhibitor
GGTI: geranyl-geranyl transferase inhibitor
Figure 8:
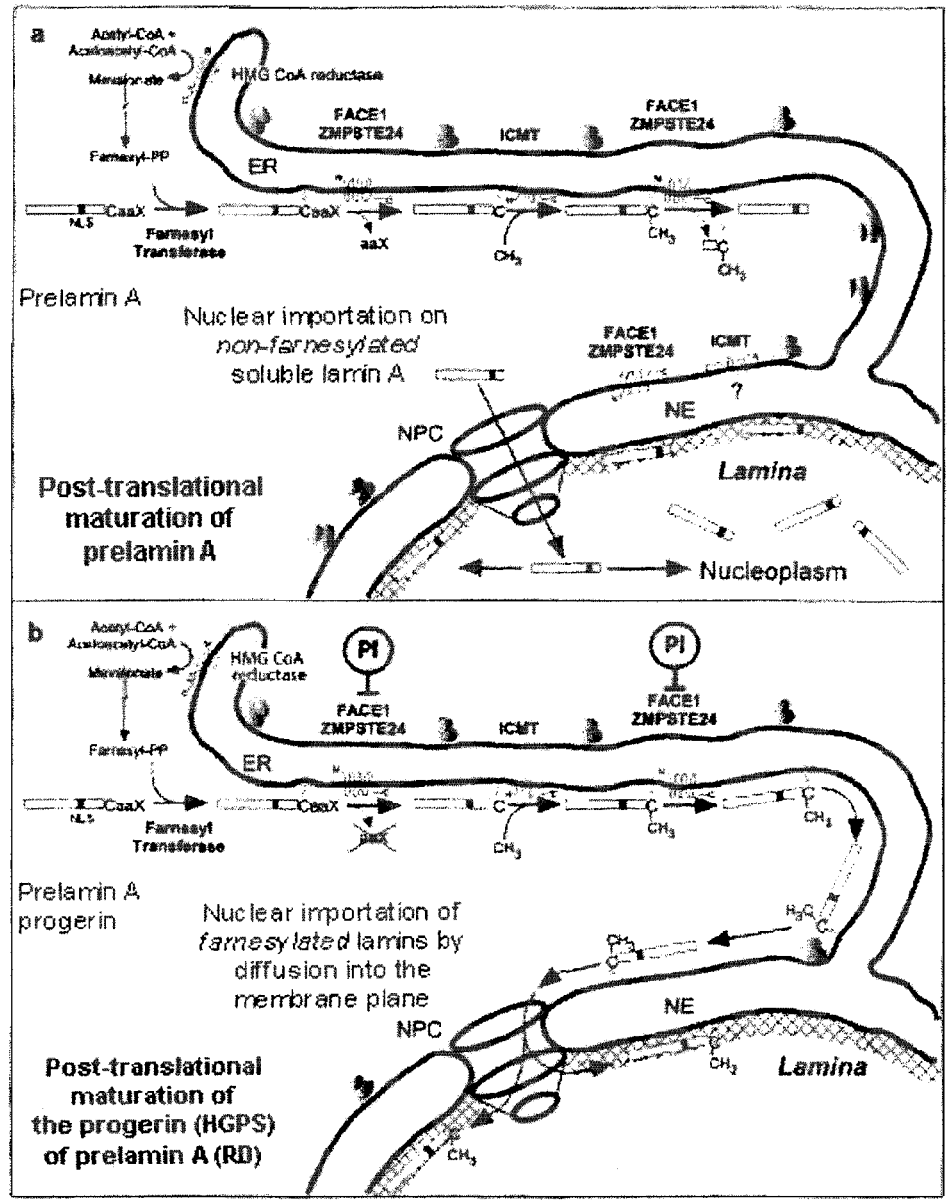
FIG. 8: Schematic representation of the post-translational maturation of prelamin A, its nuclear importation and its localization in the nucleoplasm.
a: normal prelamin A
b: maturation of prelamin A deleted in the progeria (progerin) or during a mutation of the ZMPSTE24 protease in restrictive dermopathy. The protease inhibitors of the AIDS virus (PI) inhibit ZMPSTE24.
NPC: nuclear pore
NE: Nuclear envelop
HGPS: Hutchinson-Gilford progeria Syndrom
RD: restrictive dermopathie
Figure 9:
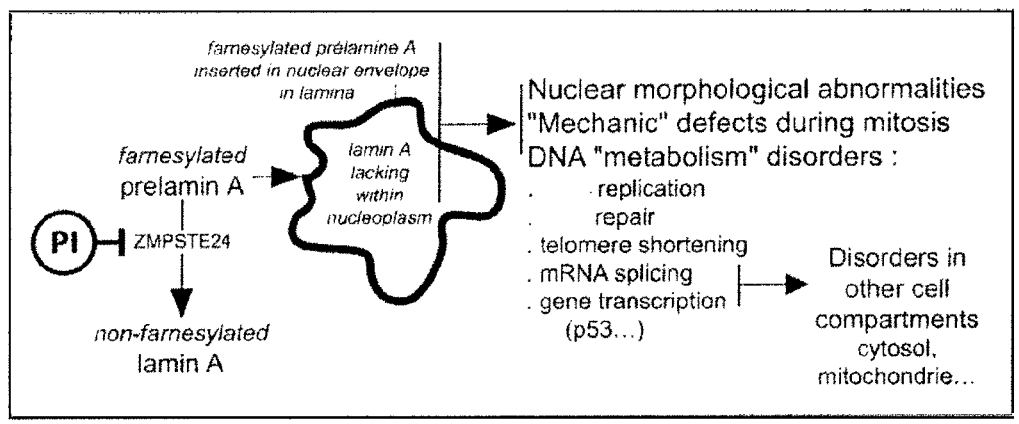
FIG. 9: Schematic representation of the theory of aging based on abnormalities of lamins and their functional consequences. Legend: PI: viral protease inhibitors

In general, the number of aged fibroblasts without any treatment in the DNA synthesis phase was extremely low: less than 5% (see FIG. 5, column 1).

The mitotic index was also not very high for the young fibroblasts: on the order of 15% (see FIG. 5, column 6). By comparison with the aged control fibroblasts without any treatment, the control fibroblasts exposed to ethanol (0.1%-24 hours) show no significant difference (p=0.11, n=6) in their mitotic index. The values were then combined (control, n=12).

The results shown in FIG. 5, column 2 show, on the mitotic index of aged fibroblasts, an A1B1 (Zolendronate-Pravastatin) activating effect with respect to the control (maximum stimulation by a factor of 2) ($p<0.001$, $n\geq 6$).

This example therefore shows that the application of the Zolendronate-Pravastatin combination has an activating effect on the cell division of fibroblasts in an aged subject.

Example 3

Effect of the Association of a Hydrosoluble Hydroxymethylglutaryl-Coenzyme A (BMG-CoA) Reductase Inhibitor and a Farnesyl-Pyrophosphate Synthase Inhibitor on a Mouse Model Having a Progeroid Syndrome The Zmpste24$^{-/-}$ KO mice used here are those described in the cited article of Varela & al., 2005 (49). Evidence of efficacy of the association of the two molecules (pravastatin and zoledronate) was reported in collaboration with a Spanish laboratory (C. Lopez-Otin).

The efficacy is obtained at combined doses that do not have an effect when the products are used separately, demonstrating an additive effect.

The two molecules (Zoledronic acid (Zometa (registered trademark)) 100 µg/kg/day and Pravastatin 100 mg/kg/day) were diluted in PBS 1× and injected intraperitoneally, on a daily basis, in 1-month-old mice until their death. The controls are wild mice of the same range, treated with PBS 1× alone.

The survival of the treated mice was significantly improved, and was maximal for females, with an average lifespan increase of around 80%. The clinical symptoms of the disease were all considerably reduced with respect to the individuals treated with PBS alone. In particular, an effect was observed of the treatment on the skin and the regrowth of fur on these mice with respect to the mice treated with PBS, which showed large bald areas.

Example 4

Effects of the Association of a Hydrosoluble Hydroxymethylglutaryl-Coenzyme A (HMG-CoA) Reductase Inhibitor and a Farnesyl-Pyrophosphate Synthase Inhibitor on Ex-Vivo Human Skin Extracts A. Protocol In this example, the tests are performed on skin from a donor around 60 years of age. A preparation of 21 explants of human skin is produced and kept alive in a BEM medium (BIO-EC's Explants Medium).

The explants are distributed into three batches of six explants and one batch C0 of three explants, as follows:
C0—Control plasty: 3 explants
C—Non-treated control: 6 explants
R—Positive control: 6 explants
P—Explants treated by the composition of the invention 6 explants A.1 Treatment The treatment is performed on a different day, the first day (D0), 2 hours after preparation of the explants, then D+1 day, D+2 days, D+4 days, D+6 days, D+8 days and D10+ days.

The products are applied to the explants as follows:
C—the explants do not receive any treatment,
R—the explants each receive, on D0, D+2 and D+4, 1 mg of the positive control (retinol cream),
P1—the explants each receive, and at each treatment time, 2 mg of product P.

The treatment is performed by topical application of the composition of the invention. The composition is then distributed over the entire surface of the explant, using a spatula. Half of the culture medium is renewed every two days and the explants are kept alive at 37° C. in a humid atmosphere enriched with 5% $CO_2$.

A.2. Sampling for Histology

At D0, the three explants of batch C0 are obtained.

At D+6 days and D+11 days, three explants of each batch are obtained. The samples are cut in two, and one half is fixed in formaldehyde while the other half is frozen at −80° C., according to the BIO-EC procedure "P006-PPEH".

B. Histological Study

After 24 hours of fixation in the formaldehyde, the samples are dehydrated, impregnated and coated with paraffin. 5 µm cross-section cuts are produced for morphological observation.

B.1. First Step: Morphological Study

The morphological study of the epidermal and dermal structures is performed on cross-section cuts with Masson's trichrome staining, a variant of Goldner's.

B.2. Second Step:

B.2.1 Immunolabeling of KI67:

The immunolabeling of cells in mitosis is performed on frozen cross-section cuts with the anti-KI 67 polyclonal antibody (Novo Castra) detected in DAB. The positive cells are counted over the entire epidermal length and averages are returned for the number of cells labeled per cm.

B.2.2 Immunolabeling of Collagen I:

The immunolabeling of collagen I will be performed on frozen cross-section cuts with the anti-collagen I polyclonal antibody detected in FITC. The nuclei are counterstained with propidium iodide.

B.2.3 Immunolabeling of Collagen III:

The immunolabeling of collagen III is performed on frozen cross-section cuts with the anti-collagen III polyclonal antibody detected in DAB. The nuclei are counterstained with Masson's hemalun.

B.2.4 Immunolabeling of Collagen IV:

The immunolabeling of collagen IV is performed on frozen cross-section cuts with the anti-collagen IV polyclonal antibody (Cliniscience) detected in FITC. The nuclei are counterstained with propidium iodide.

B.2.5 Immunolabeling of Collagen VII:

The immunolabeling of collagen VII is performed on frozen cross-section cuts with the anti-collagen VII monoclonal antibody detected in FITC. The nuclei are counterstained with propidium iodide.

B.2.6 Immunolabeling of PECAM1:

Endothelial cells can be viewed by immunolabeling of PECAM-1, performed on frozen cross-section cuts with the anti-PECAM-1 monoclonal antibody detected in Fast-red.

Example 5

Effect of the Association of a Hydrosoluble Hydroxymethylglutaryl-Coenzyme a (HMG-CoA) Reductase Inhibitor and a Farnesyl-Pyrophosphate Synthase Inhibitor on In Vitro Skin-Forming Cell Cultures This example uses the same combinations of active agents used in example 2 above. These various combinations of active agents are used in vitro in order to evaluate their effect on physiological parameters involved in skin aging.

The combinations used in this example are A1B1, A1B2, A2B1, A2B2, respectively. These four combinations are tested at a plurality of concentrations, and the experiments are performed in triplicate (representing at least 36 experimental points).

The concentrations of the four combinations are proposed by the applicant, and, therefore in vitro cytotoxicity is not envisaged at this stage of the study (unless as a simple test). The experimentation is performed on cell cultures of a fibroblast line as shown in example 1. This test is also applied to keratinocytes cultures. The following parameters are examined for the four combinations of active agents at the concentrations indicated.

Measurement of the mitotic index;
Measurement of remodeling of the extracellular matrix by contraction of collagen lattices;
Measurement of the DNA genome repair after irradiation with UVB (photoinduced stress similar to sunbathing conditions).

The measurement of the mitotic index is performed after exposure of the cells to the active agents in a single time. The index is evaluated by an image analysis count of the cell nuclei having incorporated a thymidine analog rendered fluorescent, over the total number of nuclei. A plurality of fields are analyzed. The photos are archived for iconography.

The remodeling of the extracellular matrix induced by the fibroblasts exposed to the active agents is evaluated by incorporating these cells into the collagen lattices and by quantifying their capacity to retract these lattices. The retracted surface evaluation gives a remodeling index. The photos are archived for iconography.

The measurement of DNA genome repair is performed after irradiation of the cells at a UV-B dose mimicking sun exposure conditions. The objective is first to evaluate the effect of the active agents during DNA repair monitored over a period of 3 times. The quantification is performed by cyclobutane pyrimidine dimer image detection and analysis by UVB irradiation using an immunohistochemical technique.

The photos are archived for iconography.

Example 6

Main Objective: Measurement of the Impact of the HIV Virus and Antiretroviral Therapies on Nuclear, Mitochondrial and Cytosolic Markers of Cell Aging Secondary Objectives To analyze the prevalence of alterations of nuclear, mitochondrial and cytosolic functions in HIV-infected patients;
To measure the incidence of appearance of these abnormalities;
To analyze the type and frequency of these abnormalities according to the duration of exposure to the antiretrovirals, overall, by class and by molecule (cumulative exposure time);
To analyze the type and frequency of these abnormalities according to the intracellular HIV viral load;
To analyze the type and frequency of these abnormalities according to the HIV-infection follow-up duration.

A. Experimental Plan

Choice of Experimental Plan

This observational study includes three groups of patients:
Group A: HIV1-infected patients without any antiretroviral treatment;
Group B: HIV1-infected patients under antiretroviral treatment for at least 12 months;
Group C: HIV-negative controls matched by age and sex.

B. Eligibility Criteria:

Inclusion Criteria:
age >18 years and <65 years:
having signed an informed consent form;
HIV1 positive confirmed with Elisa and Western blot for at least 5 years;
HIV2 negative;
Never having received antiretroviral treatment, or as a first line of treatment for at least 12 months.

Non-Inclusion Criteria:
age <18 years and >65 years:
not having signed the informed consent form;
HIV2 positive
patients treated with statins or amino-biphosphonates
unauthorized concomitant treatments: testosterone, insulin-dependent diabetes treatment.

C. Study Procedure

Number of Patients Evaluated:
200 patients including:
  Group A: n=50
  Group B: n=100
  Group C: n=50

The patients of group A needing, during their follow-up, to start an antiretroviral treatment have an additional evaluation when starting the treatment and are analyzed starting on that date with the patients of group B.

The data measured over the period during which they were included in Group A makes it possible to measure the possible direct role of the HIV virus on nuclear and mitochondrial functions.

The patients of group B needing an antiretroviral treatment modification during the studies have a clinical and paraclinical evaluation identical to those provided in the context of the follow-up when there is a change in treatment. The follow-up data on these patients is taken into account to calculate the incidence of disruptions of nuclear and mitochondrial functions observed in patients exposed to antiretrovirals.

Study Duration:
The study duration is 36 months.
For Patients of Groups A and B
History of HIV Infection:
Date of HIV infection diagnosis
Mode of contamination
CDC stage
For stage C: diagnosis of AIDS-defining condition
Antiretroviral treatments in progress (start date, molecules administered)

Clinical Exam:
Weight, height, body mass index
Waist circumference, hip circumference, waist-to-hip ratio
Blood Tests:
Measurement of the HIV viral load (detection threshold 40 copies/ml)
Assay of CD4 and CD8 lymphocyte levels
Glycemia, insulinemia, HOMA calculation
Total cholesterol, LDL, HDL cholesterol
Triglycerides
Sampling of 3 EDTA tubes of 7.5 ml for analysis of nuclear and mitochondrial functions, measurement of HIV proviral DNA and cell library
Analysis of Antiretroviral-Target Nuclear, Mitochondrial and Cytosolic Proteins:
Western blot and immunolabeling:
Production of NF B and I B as controls of proteasome activity;
Maturation of lamins A and B, nuclear protein models;
Production of SREBP isoforms and their nuclear importation;
N- and O-glycosylation of purified and deglycosylated CD36 (±30 kDa of sugar) (Abcam);
importation, into the mitochondria, of Hsp70 having a cleaved addressing signal, as a measurement of the mitochondrial protease activity (Abcam);
mitochondrial "respiratory" functions; ROS production, study of subunits II and IV of the cytochrome oxidase (Molecular Probes)

The search for possible susceptibility to antiretroviral treatments is performed by genotyping certain targets, as was shown for the sensitivity of viral protease to PIs (Baxter et al., 2006):
ZMPSTE24 and Rce1 involved in maturation of prelamins A and B1/B2 (routine at the Molecular Genetics Laboratory);
S1-P and S2-P proteases enabling production of the SREBP domain active on lipid metabolism gene transcription;
The mitochondrial deoxynucleoside transporters.
For Control Group C:
Clinical Exam:
Weight, height, body mass index
Waist circumference, hip circumference, waist-to-hip ratio
Sampling of 3 EDTA tubes of 7.5 ml for analysis of nuclear, mitochondrial and cytosolic functions, and placement in DNA and libraries.
Follow-Up Visits
The evaluation includes:
A Clinical Exam:
Weight, height, body mass index
Waist circumference, hip circumference, waist-to-hip ratio
A Blood Test:
Measurement of the HIV viral load (detection threshold 40 copies/ml)
Assay of CD4 and CD8 lymphocyte levels
Glycemia, insulinemia, HOMA calculation
Total cholesterol, LDL, HDL cholesterol
Triglycerides
Sampling of 3 EDTA tubes of 7.5 ml for analysis of nuclear, mitochondrial and cytosolic proteins, measurement of HIV proviral DNA and placement in DNA and cell libraries.
Analysis of Antiretroviral-Target Nuclear, Mitochondrial and Cytosolic Proteins (See Above)
For Patients of Group A:
The patients of group A needing to start an antiretroviral treatment have a clinical and paraclinical evaluation identical to that provided in the context of the follow-up when starting the treatment. The follow-up data on these patients is analyzed from this date in the group of patients treated (group B).
For Patients of Group B:
If the antiretroviral treatment is modified during the studies, a clinical and paraclinical evaluation identical to those provided in the context of the follow-up is performed when the treatment is changed. The follow-up data on these patients is taken into account to calculate the incidence of disruptions of nuclear and mitochondrial functions observed in patients exposed to antiretrovirals.

D. Expected Results, Perspectives

Confirming, in vivo in patients infected by the AIDS virus and undergoing antiretroviral treatments, the results obtained in vitro in cell cultures: these treatments, in particular protease inhibitors, induce accelerated aging according to the same mechanisms as genetic laminopathies (with the production of farnesylated prelamin A or progerin) or "physiological" aging (with progerin production).

Reinforcing the hypothesis according to which the combination of drugs (statin and aminobiphosphonate) used in progeria might be used to fight accelerated aging in patients infected by the AIDS virus and undergoing an antiretroviral treatment and enabling the establishment of a therapeutic test.

Example 7

A Treatment Associated a Statin and an Aminobiphosphonate Increases the Lifespan of a Mouse Model Reproducing a Human Syndrome of Premature Aging This example is also published in Varela and al, Nature Medicine 2008, 7, 767 (54 bis).
Equipment and Methods
Mice:
The production of Zmpste24$^{-/-}$ and Lmna$^{-/-}$ mice has been described (Pendas and al. 2002 (38); Sullivan and al., 1999 (285). The computerised bone microtomography of the mice was carried out using the micro-CT SkyScan 1172 system (SkyScan—trademark)). All of the experiments on mice are governed by the rules set down by the Animal Experiment Committee of the University of Oviedo (Spain). The pravastatin (100 mg/kg/day) and the zoledronate (100 mg/kg/day) diluted in PBS are administered to the mice every day. The mice receiving the pravastatin-zoledronate treatment or the control mice receiving only PBS do not show any apparent damage or stress.
Cell Culture
The dermal fibroblasts of a control subject (GM00038) and of patients afflicted with progeria and carriers of the mutation G608G (AG11498 and AG01972) were obtained from the Coriell Cell Repository. The HeLa cells come from the American Type Culture Collection. The cells are cultivated in DMEM (Gibco) supplemented with 10% FBS (Gibco) and 1% antibiotic-antimycotic (Gibco). The fibroblasts come from tails of 12-day-old mice (Varela and al., 2005). The concentration and the duration of treatment with the statin and the aminobiphosphonate are indicated in the legende of the figures. During the combined statin+aminobiphosphonate treatment in the presence of farnesol and/or of geranylgeraniol, 1 mM of pravastatin and 1 mM of zoledronate were added to the culture medium with increasing concentrations of farnesol and/or of geranylgeraniol. The percentage of abnormal nuclei is measured 48 h after the beginning of the treatment.

Immunocytochemistry

The fibroblasts are cultivated in Lab Tek chambers (Nalgen Nunc International), washed in the PBS, then fixed in paraformaldhyde 4% for 15 min. The cells are dehydrated in ethanol baths in increasing concentration and are permeabilised 5 min at 25° C. in PBS containing Triton X-100 (0.5%), 5% serum (goat or rabbit). The slides are pre-incubated at 25° C. in PBS for 5 min.

The dilution of the primary antibodies is 1/100 for the goat polyclonal anti-prelamin A antibody (Sc-6214, Santa Cruz Biotechnologies), 1/40 for the anti-lamin A/C antibody (4A7 provided by G. Morris), 1/200 for the Rabbit anti-calreticulin antibody (Stressgen) and 1/100 for the B1 anti-lamin antibody (Abcam). After washing in the PBS, the slides are incubated 1 h at 25° C. with the secondary antibodies diluted in the incubation solution. The dilution of the secondary antibodies is as follows: 1/100 for the IgG of donkey anti-mouse coupled with FITC (Jackson ImmunoResearch), 1/400 for the IgG of donkey anti-goat coupled with the Alexa 488, 1/800 for the IgG of donkey anti-goat coupled with the Alexa 568 (Molecular Probes) and 1/100 for the IgG of donkey anti-rabbit coupled with tetramethylrhodamine isothiocyanate (Sigma). The cells are then washed, the nuclei coloured for 15 min at 25° C. with DAPI (100 ng/ml, Sigma-Aldrich), finally washed 3 times with PBS containing 0.5% of Tween 20. The slides are mounted in Vectashield (Vector). Digital images are recorded with a Leica DMR microscope equipped with a CoolSnap camera or with a Leica TCS SP5 confocal microscope. The nuclei are observed in the cells after marking of the lamin A/C. More than 100 nuclei were analysed in the control fibroblasts for each of the treatments. The number of nuclei of cells of patients afflicted with progeria analysed is 250 (passage 8), 198 (passage 13) and 150 (passage 20).

Irradiation X and Study of the H2AX Phosphorylated Histone.

The cells of progeria patients and the 1BR3 control cells are irradiated with an Philips X device. The X ray is produced by an tungsten anode subjected to a voltage of 200 kV under an intensity of 20 mA with a copper filter of 0.1 mm in diameter. The dose rate is 1.243 Gy/min. The H2AX phosphorylated histone is detected with antibodies that specifically recognise the phosphorylated serine 139 (Upstate Biotechnology-Euromedex, Mundolsheim, France) at the dilution 1/800 and of the anti-mouse antibodies conjugated with the FITC (1/100, Sigma-Aldrich). The number of double-strand breaks (DSB) according to the duration of the repair was adjusted with the formula $Nt=N0\,(1/1+\beta t)^{\alpha}$, where $\alpha$ and $\beta$ are adjustable parameters and Nt and N0 are the number of DSB in time t and in time 0.

Western Blot

The cells are homogenised in the following medium: 50 mM Tris (pH 7.4), 150 mM NaCl, 1% NP-40, 50 mM NaF, 1 mM dithiothreitol, 2 mg/ml pepstatin A, in the presence of protease inhibitors (Complete inhibitor cocktail, Roche) and phosphatase inhibitors (Phosphatase Inhibitor Cocktails I and II, Sigma). After electrophoresis, the proteins are transferred onto nitrocellulose membranes blocked with 5% of delipidated milk powder, using the TBS-T buffer (20 mM Tris pH 7.4, 150 mM NaCl and 0.05% Tween-20), and incubated 1 h with either a specific anti-lamin A/C antibody (4A7, 1/500), or a specific anti-lamin A (C20, Santa Cruz Biotechnology, 1/250) or an anti-beta actin (A5441, Sigma, 1/5000). The antibodies are diluted in TBS-T containing 3% of delipidated milk powder. The blots are then incubated with an antibody coupled with the peroxidase (goat anti-mouse or anti-rabbit, Jackson ImmunoResearch) in TBS-T containing 1.5% of delipidated milk powder, then washed, finally revealed via chemiluminescence (Immobilon Western chemiluminescent HRP substrate, Millipore—trademark).

Analysis Via Mass Spectrometry

The fibroblasts of control and Zmpste24$^{-/-}$ mice as well as the cells lymphoblastoids of progeria patients have been homogenised, the nuclei isolated via ultracentrifugation and the nuclear proteins obtained as described in Blobel and Potter, V. R. Nuclei from rat liver: isolation method that combines purity with high yield, Science 154, 1662-1665, 1966. The proteins of the nuclear lamina were separated via SDS-PAGE electrophoresis, and the strips containing the lamin A, the prelamin A and the progerin were excised. The fragments of the gel were washed twice with 180 ml of a ammonium bicarbonate/acetonitrile mixture (70/30, 25 mM), dried (15 min, 90° C.) and digested (1 h, 60° C.) with trypsin (12 ng/ml, Promega) in the ammonium bicarbonate 25 mM. In a typical experiment, 1 ml of CHCA (a-cyano-4-hydroxycinnamic acid, Waters) is placed in a MALDI-ToF spectrometer. Once dried, 1 ml of the peptide solution and 1 ml of the matrix (CHCA) are placed in the spectrometer equipped with a laser source (Voyager-DE STP. (trademark), Applied Biosystems). The data collected using 200 laser firings produce spectra analysed with the Data Explorer programme (version 4.0.0.0, Applied Biosystems).

Quantitative PCR in Real-Time

The expression rate of target genes of p53 (Atf3, Gadd45g and Cdkn1a, which code p21) has been measured using the device ABI PRISM 7900HT Sequence detection system (Applied Biosystems).

Statistical Analysis

The difference between the different mouse groups and the cells, treated or not, has been analysed during the Student test. The calculations were effected using the program Microsoft Excel. The data is expressed as an average figure±standard error of the average.

Results

HeLa cells were cultivated in the presence of farnesyl transferase inhibitors (FTI-277, Sigma-Aldrich) and/or geranyl-geranyl transferase type I (GGTI-2147) at the concentrations indicated. Only the combination of the two inhibitors allows for a sufficient build-up of not prenylated prelamine A in the cells with regard to the effect of each inhibitors solely used.

Figure 10:
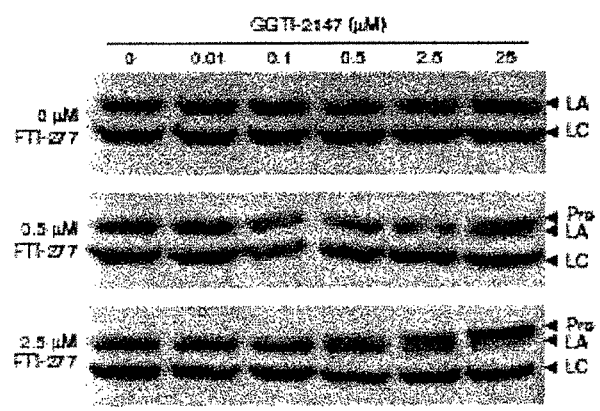
FIG. 10: Western blot showing that the blockage of prelamin A phenylation requires both the inhibition of farnesyl-transferase and type I geranyl-geranyl-transferase. Detection of lamin A/C in HeLa cells treated with farnesyl-transferase inhibitors and/or type I geranylgenarnyl transferase. LA=lamin A, LC=lamin C, Pre=prelamin A.

These results are shown in FIG. 10 which is a photography of an obtained Western blot, displaying the detection of the A/C lamine in the HeLa cells treated by the farnesyl transferase inhibitors and/or the type I geranyl-geranyl transferase. LA=lamine A, LC=lamine C, Pre=prelamin A.

These results confirm that the prenylation blockage of the prelamine A necessitates, at the same time, the inhibition of the farnesyl transferase and the geranyl-geranyl transferase type I, according to the present invention.

The farnesyl transferase (FTI) inhibitor induces the compensatory geranylation of the progerin (in the cells of patients afflicted with progeria) and in the Zmpste24$^{-/-}$ mouse fibroblasts The mass spectrometry analysis indicates, as expected, the presence of tryptic peptides of the farnesyled and carboxymethylated in Zmpste24 mouse cells but not in control mice cells. These results are shown in FIG. 13a. The farnesyled peptide lacks the 3 SIM residues which shows that the Zmpste24 is not indispensable for the first clivage during the maturing of the prelamine A. In the FTI-treated mice cells, there was observed a reduction in the quantity of farnesyled prelamine A. During the observation of the part of the spectrum for the geranyl-geranylised peptides, there was no peptide derived from the prelamine A detectable in the cells of the non-treated Zmpste24$^{-/-}$ mice. But there was detected a peptide which mass is compatible with a geranylgeranylated fragment of the prelamine A, after FTI treatment. The results are shown in FIG. 13b.

In the cells of the progeria patients, those peptides corresponding to the farnesyled and carboxymethyled progerin are detected without any treatment, as indicated in FIG. 11a. The treatment of the cells by FTI-127 fosters the appearance of peptides whose mass corresponds to that of the geranyl-geranyl peptides of the progerin, as indicated in FIG. 11b.

This data as a whole shows that the progerin and the prelamine A have been geranylgeranylated in an alternative manner under the effect of the FTI and provides an explanation of the poor efficacy of the FTI treatments in the murine models of progeroid syndrome.

The cells of the progeria patients and Zmpste24$^{-/-}$ mice were used to evaluate the therapy strategies intended to prevent crossover prenylation of the prelamine A and the progerin. We have established the hypothesis that the farnesylation of the abnormal variants of the lamine A, could be inhibited by drugs which have an effect on biosynthesis pathway of the farnesyl pyrophosphate, farnesyl transferase substrate and the geranyl-geranyl pyrophosphate precursor, substrate of the type I geranyl-geranyl transferase. We have thus tested the effects of two drugs, a statin and an aminobiphosphonate, which are known to affect the cells of the progeria patients at two step of this metabolism pathway. The mass spectrometry analysis shows that the association of pravastatin (statin) zoledronate (aminobiophosphate) stimulates the appearance of a peptide which corresponds to the C-terminal extremity not prenylated of the progerin, a peptide not detectable in the FTI-treated cells; while neither farnesylated peptides nor the geranyl-geranylated peptides are detected any more, as shows on FIG. 11c. The statin+ aminobiophosphate treatment inhibits the prenylation of the progerin. The same was observed with the prelamine A, as indicated in FIG. 12. Its C-terminal peptide, not prenylated, was detected in the cells treated by the mixture of statin and aminobiphosphonate while being free of non-treated cells; in which one detects the farnesylated and carboxymethylated peptide. Finally, the pravastatin+zoledronate treatment does not feature in the gernaylgeranylated prelamine A, this is not the case with the FTI.

Figure 13:
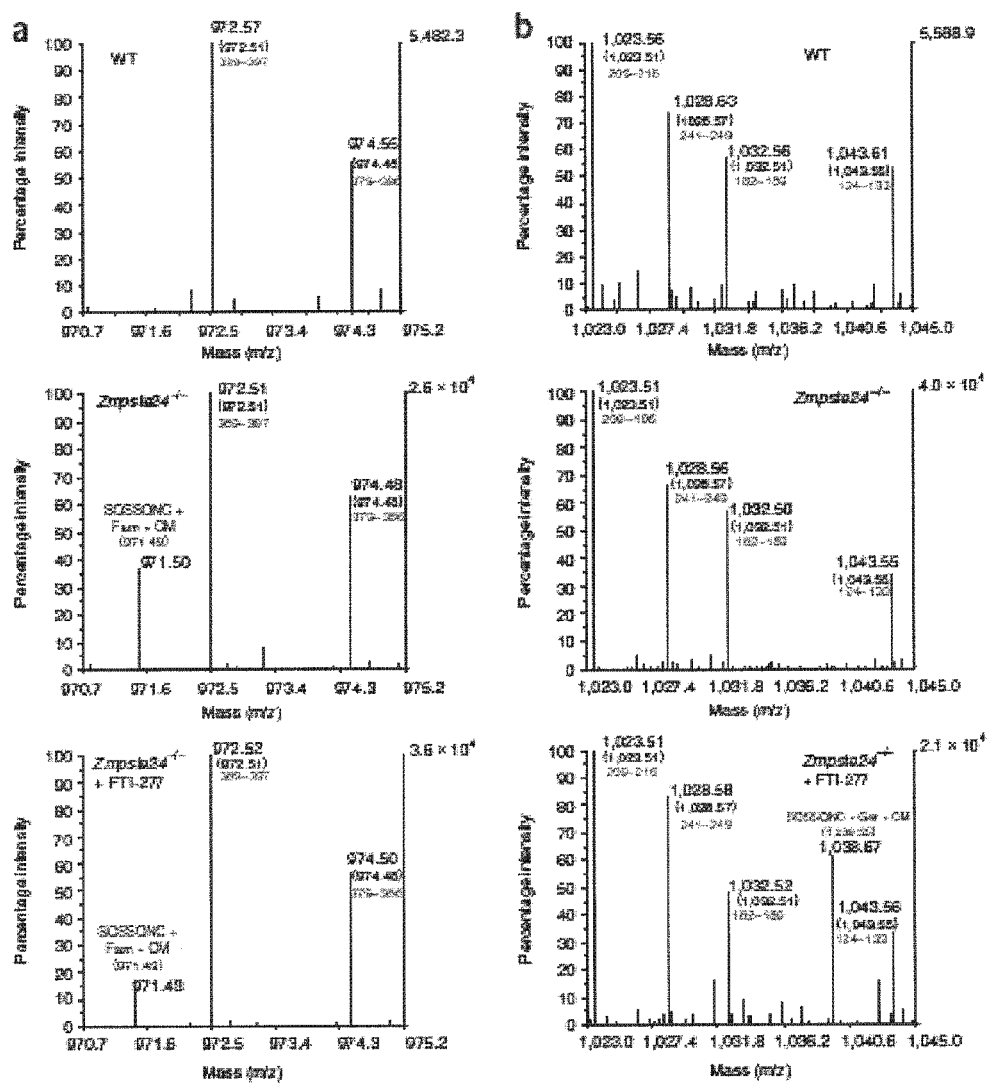
FIG. 13: Lamin A (control cells) and prelamin A (Zmpste24$^{-/-}$ mice cells) were analysed by mass spectrometry (MALDI-ToF). a, b: portions of the spectrum corresponding to farnesylated (a) and geranylgeranylated (b) tryptic peptides.

FIG. 13 legend: the lamine A (control cells) and the prelamine A (Zmpste$^{-/-}$ mouse cells) have been analysed by a mass spectrometry analysis (MALDI-ToF). a, b: portions of the spectrum corresponding to the farnesylated tryptic peptides (a) and the geranylgeranylated peptides (b). Each of the peack is marked by the theorical mass (between parentheses) of the peptide from the trypsin digestion of lamin A, or the prelamin A. The number of the residues is indicated in blue. The sequence of the peptides and their masses are indicated in red. Farn=farnesyl-treated; CM=carboxymethyl-treated; Ger=geranyl-geranyl-treated.

Figure 11:
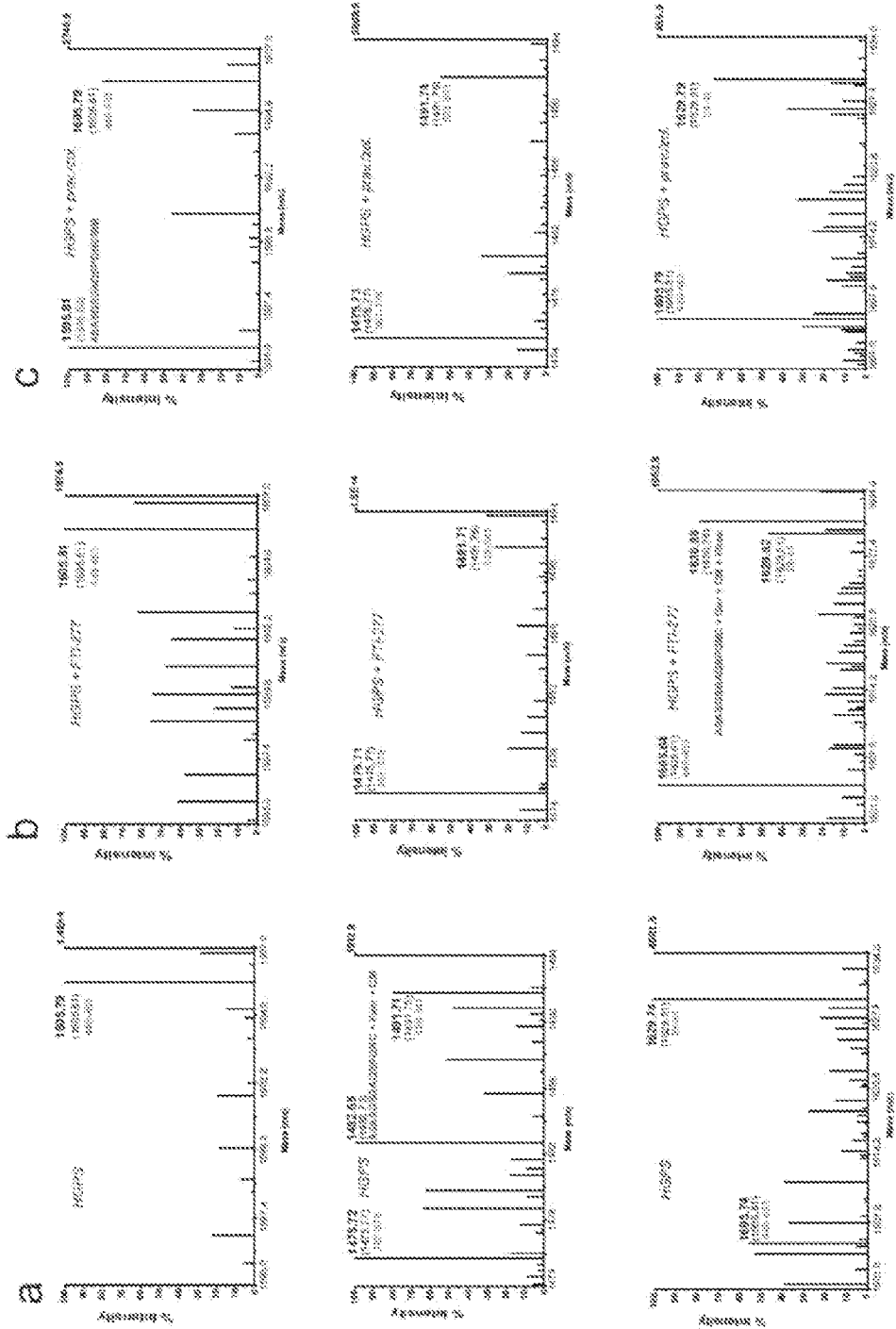
FIG. 11: Mass spectrometry analysis of proteins extracted from the nuclear envelope of untreated cells (a), cells of progeria patients treated with FTI (2.5 µM, b) or treated with the pravastatin+zoledronate mix (1 µM each, c).
Figure 12:
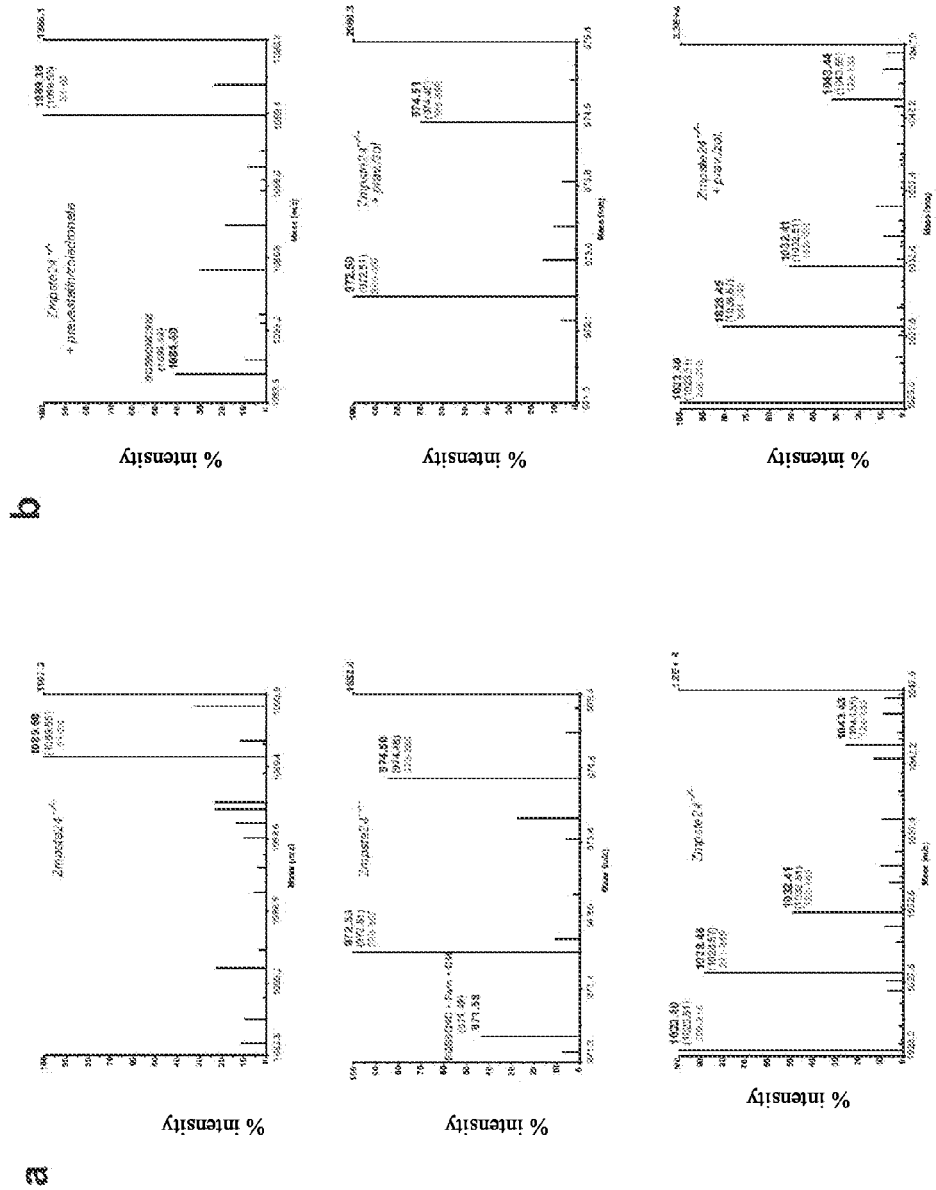
FIG. 12: Mass spectrometry analysis of proteins extracted from the nuclear envelope of untreated fibroblasts (a) or treated with the pravastatin+zoledronate mix (1 µM each, b) from Zmpste24$^{-/-}$ mice.

FIG. 11 legend: mass spectrometry analysis of the proteins extracted from the nuclear envelop of the untreated cells (a), of the cells of the progeria patients treated with FTI (2.5 μM, b) or treated with the mixture of pravastatin+ zoledronate (1 μM apiece, c). The portion of the spectra corresponding to the non-modified proteins, the farnesylated proteins and the geranylgeranylated proteins is indicated on the top, in the center and at the bottom of the figure. Each peak corresponds to the tryptic peptide of the progerin and is marked with the measured monoisotopic mass in experiment and with the theoretical mass (between parentheses). The number of the amino acid residues is indicated in blue.

The sequence of the peptides and their mass is indicated in red.

The progerin is predominantly farnesylated (F) and carboxymethylated (Cm) in the unaffected cells (a, centre panel); while, with the effect of the FTI, this peak is considerable reduced, and the progerin appears geranylgeranylated and phosphoryl (b, lower panel). After treatment with pravastatin and zoledronate, the unmodified progerin is the predominant form.

FIG. 12 legend: a mass spectrometry analysis of the proteins extracted from the nuclear envelop of the untreated fibroblasts (a) or treated with a mixture of pravastatin+ zoledronate (1 μM apiece, b) stemming from Zmpste24$^{-/-}$ mice. The portion of the spectra corresponding to the unmodified proteins, the farnesylated proteins and the geranylgeranylated proteins, is indicated on the top, in the center and on the bottom of the figure. Each peak corresponds to a tryptic peptide of the progerin and is marked with a monoisotopic mass measured the experiment and with the theoritical mass (in parentheses). The number of the amino acid residues is indicated in blue. The sequence of the peptides and their mass is indicated in red.

In this figure, one can see that the prelamine A is predominantly farnesylated (F) and carboxymethylated (Cm) in the untreated cells (a, centre panel), while the unmodified or geranylgeranylated forms are not detected. After treatment with pravastatin and zoledronate, the prenylated peptides are no longer detectable, and the non-modified form of the prelamine A is predominant (b, upper panel).

The treatment with pravastatin+zoledronate corrects the nuclear anomalies of the progeria patients cells and Zmpste24$^{-/-}$ mice cells being in culture; and partially restore the DNA lesion repair mechanisms induced by X-rays (FIGS. 14, 15, 16 and 17).

The pravastatin+zoledronate treatment causes prelamin A to appear in the nucleus of control cells (FIG. 14a), as in the cell nucleus of progeria patients cells, but with a significant improvement in nuclear morphology in the latter cells (FIG. 14b). Quantitative analysis shows an increase in nuclear anomalies in the cells of progeria patients as the number of passes increases; this number of anomalies decreases under the effects of the pravastatin+zoledronate treatment (FIG. 14c.). When observed under a confocal microscope, the cells of progeria patients contain aggregates of lamin A/C and deep invaginations of the nucleoplasmic surface of the nuclear envelope in the nucleoplasm (nuclear reticulum), marked by anti-calreticulin (FIG. 15a-f). These lamin A/C aggregates are absent from the cells of control subjects (FIG. 14j-l) and disappear from the cells of progeria patients under the effects of the pravastatin+zoledronate treatment (FIG. 14g-i). The location of the lamin B1, a farnesylated component of the nuclear lamina, is modified under the effects of the treatment, confirming that the treatment blocks the prenylation of lamins.

We checked that the improvement in the nucleus shape due to the pravastatin+zoledronate treatment was indeed related to the fact that the prenylation of progerin, by incubating cells with farnesol and/or geranylgeraniol. Supplementing cells with farnesol and geranylgeraniol enables the cells to synthesise farnesyl pyrophosphate and geranylgeranyl pyrophosphate and thus to prenylate the progerin even when pravastatin and zoledronate are present (FIG. 14d). Farnesol nullifies the effect of the pravastatin+zoledronate treatment, which provides further evidence that the effects of the treatment are caused by the inhibition of farnesyl pyrophosphate synthesis. It should be noted that geranylgeraniol also blocks the effect of the treatment, which proves that the geranylgeranylated form of progerin is also toxic for the cells (FIG. 14d). The same effects are observed in Zmpste24$^{-/-}$ cells (FIG. 16a), which suggests that the data on progerin can be extended to prelamin A, the protein accumulated in Zmpste24$^{-/-}$ cells. Neither farnesol nor geranylgeraniol have any effect on the control fibroblasts, which rules out the possibility of an artefact induced by these molecules (FIG. 16b.).

Figure 17:
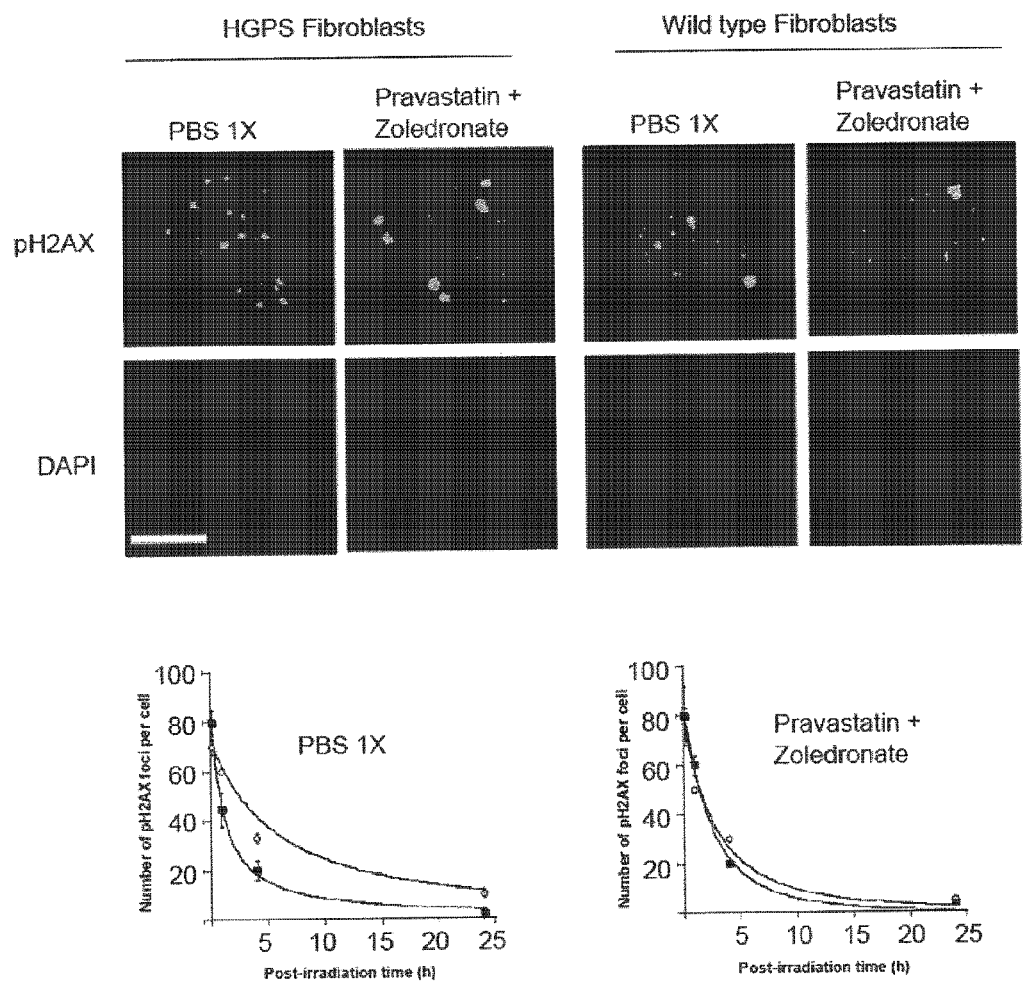
FIG. 17: Effect of the pravastatin+zoledronate treatment on the anomalies of the double-strand break repair (DSB) of the DNA in the cells of progeria patients. Immunodetection of the foci of the H2AX phosphorylated histone detected 24 h after irradiation, foci corresponding to the unrepaired double-strand breaks (images at the top). Nuclear marking of the DAPI (images at the bottom). Curves at bottom: change in the number of foci of H2AX phosphorylated histone according to time after irradiation in the control cells (solid square) and the progeria cells (empty circle) incubated with the PBS or treated with pravastatin+zoledronate. Each curve represents the mean±standard error of the mean of at least 3 experiments.

Finally, the pravastatin+zoledronate treatment causes a reduction in the number of phosphorylated histone H2AX foci; these foci are directly correlated with the number of unrepaired DNA double-strand breaks (FIG. 17).

In conclusion, the in vitro data gathered shows that the pravastatin+zoledronate combination partially inhibits farnesylation and geranylgeranylation and causes the expected changes of location within the lamina and redistribution within the nucleoplasm of non prenylated prelamin A and progerin in the Zmpste24$^{-/-}$ cells and in progeria patients. Likewise, the decreased quantity of farnesylated progerin within the lamina and its relocation to the nucleoplasm explains the beneficial effects of the treatment on the cells of progeria patients.

Figure 14:
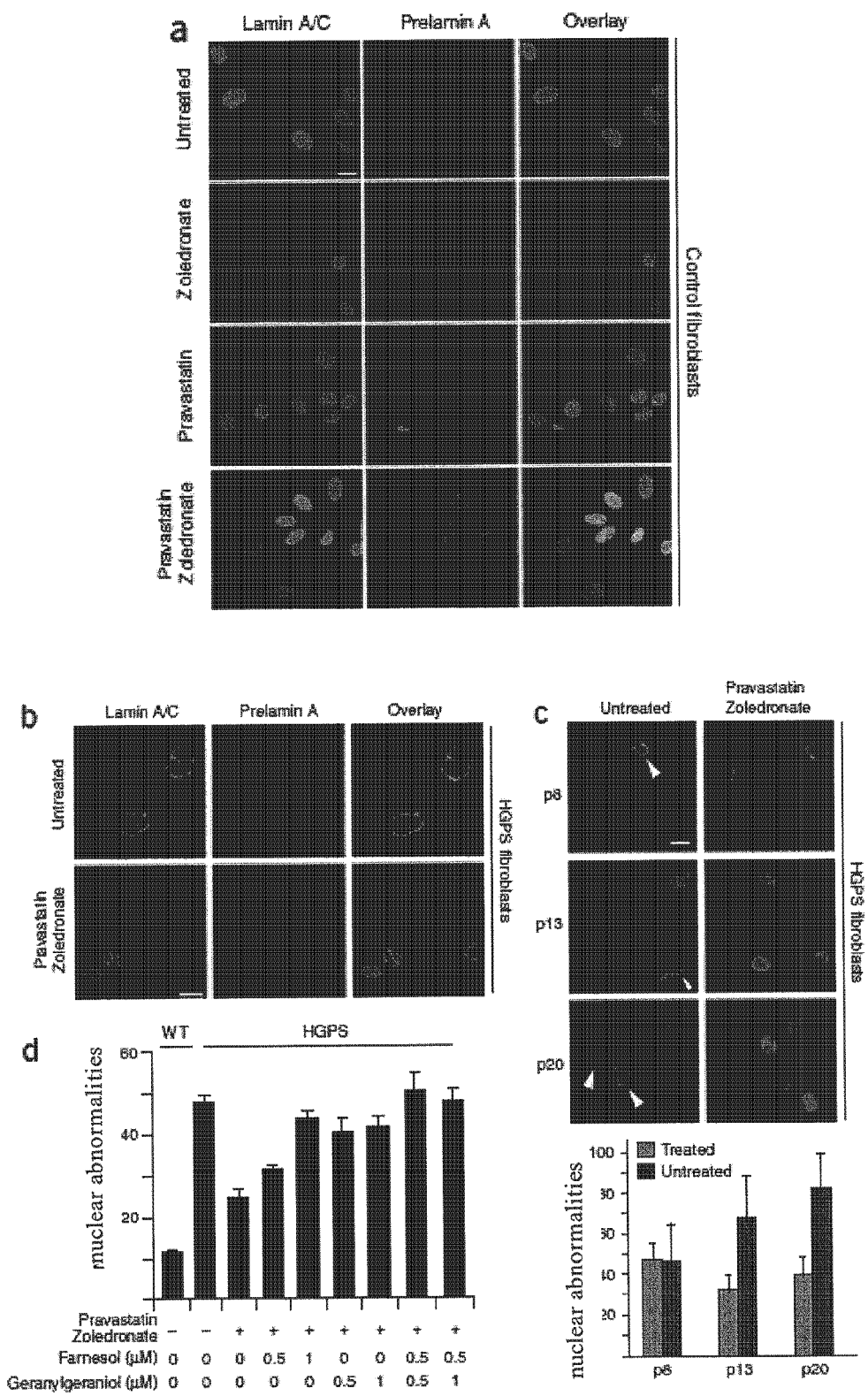
FIG. 14: representations of results of different experiments demonstrating the synergic effect of the pravastatin+zoledronate combination on the accumulation of prelamin A in control cells and progeria patients: (a) Immunocytochemical detection of lamin A/C and prelamin A in untreated human fibroblasts treated with pravastatin and/or zoledronate. (b) Immunocytochemical detection of lamin A/C and prelamin A in normal human fibroblasts and from patients with progeria treated with the pravastatin+zoledronate combination. (c) Quantitative analysis of the effect of pravastatin+zoledronate treatment on the nuclear morphology of cells from progeria patients. (d) Quantitative analysis of the effect of pravastatin+zoledronate treatment on the nuclear morphology of cells from progeria patients in the presence of farnesol, geranylgeraniol or the two compounds. Error bars=mean±standard error of the mean. Scale bar=10 µm.

Legend of FIG. 14: Synergetic effect of the pravastatin+zoledronate combination on the accumulation of prelamin A in control cells of progeria patients. (a) Immunocytochemical detection of lamin A/C and prelamin A in normal, untreated human fibroblasts that were then treated with pravastatin (60 μM, 12 h) and/or with zoledronate (60 μM, 6 h), alone or in combination. (b) Immunocytochemical detection of lamin A/C and prelamin A in normal human fibroblasts and fibroblasts from progeria patients treated for 24 hours with the pravastatin+zoledronate combination (1 μM each). (c) Quantitative analysis of the effect of the pravastatin+zoledronate treatment (1 μM each) on the nuclear morphology of the cells of progeria patients. Treated and untreated cells were immuno-marked with an anti-lamin A/C antibody in passes 8 (p8), 13 (p13) and 20 (p20). The white arrows show the abnormal nuclei. (d) Quantitative analysis of the effect of the pravastatin+zoledronate treatment (1 μM each) on the nuclear morphology of the cells of progeria patients in the presence of farnesol, geranylgeraniol or both compounds. Error bars=mean±standard error of the mean.

Scale bar=10 μm.

Figure 15:
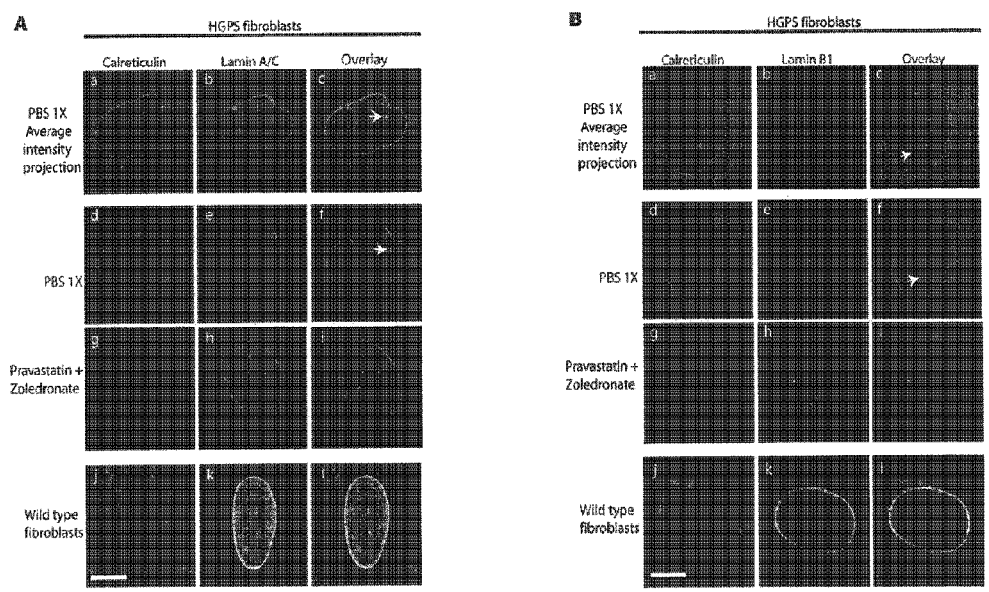
FIG. 15: representation of the results of the treatment with pravastatin+zoledronate showing the correction of the nuclear morphology and the induction of a partial relocating of the isoforms of the A/C lamin and of the 31 lamin of the nuclear lamina in the nucleoplasm, in the progeria patients cells. (A) Immunofluorescence and confocal microscopy. The images a to c of each panel are projections of the mean intensity of 27 images of the stack and show the tubules of the nuclear reticulum marked by the calreticulin in the progeria cells incubated with the PBS. Images d to 1: confocal sections isolated by 0.2 µm of thickness. Effect of the pravastatin+zoledronate treatment (g) and (h). (8) Colocalising of the B1 lamin and of the calreticulin. Scale bar=5 µm.

Legend of FIG. 15: The pravastatin+zoledronate treatment corrects the nuclear morphology and leads to a partial relocation of lamin A/C and lamin B1 isoforms from the nuclear lamina into the nucleoplasm, in the cells of progeria patients.

(A) Co-location of lamin A/C and calreticulin in these progeria cells, whether treated or untreated. Examination using immunofluorescence and confocal microscopy (Leica TCS SP5, 3D stack of 2048×2048 pixel images, intervals of 0.2 μm, average 3 rows, accumulation of 3 images, 1.7× zoom). Images a to c in each panel are mean intensity projections of 27 images from the stack and show the tubules of the nuclear reticulum marked with calreticulin in progeria cells incubated with PBS. Images d to l: isolated confocal sections of 0.2 μm thickness. The pravastatin+zoledronate treatment corrects the form of progeria cell nuclei, reduces the number of tubules of the nuclear reticulum (g) and reduces the thickness of the nuclear lamina (h).

(B) Co-location of lamin B1 and calreticulin. The pravastatin+zoledronate treatment increases the lamin B1 nucleoplasmic marking signal, which indicates that the farnesylation of this protein is partially inhibited. Scale bar=5 μm.

Figure 16:
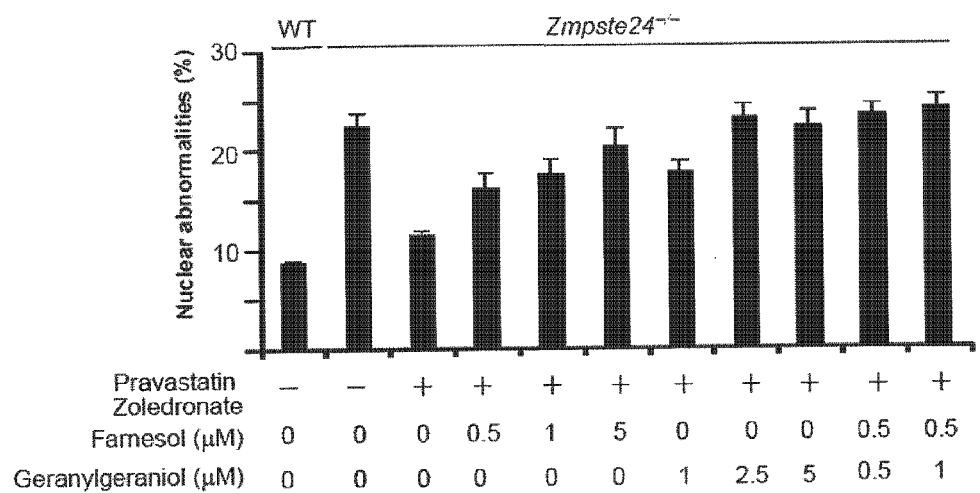
FIG. 16: representation of the effect of the pravastatin and of the zoledronate whether or not associated on the nuclear morphology of cells of Zmpste24$^{-/-}$ mice (a) and of control mice (b) in culture, in the presence of farnesol, of geranylgeraniol or of the two molecules.
Figure 16:
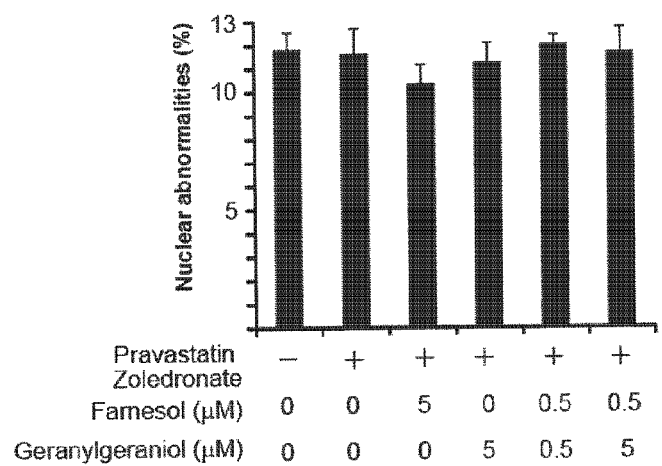

Legend of FIG. 16: The farnesyl pyrophosphate and geranylgeranyl pyrophosphate precursors nullify the effect of the pravastatin+zoledronate treatment in Zmpste24$^{-/-}$ mouse cells in culture.

Quantification of the effect of pravastatin (1 μM) and zoledronate (1 μM), alone or in combination, on the nuclear morphology of Zmpste24$^{-/-}$ mouse cells (a) and control mouse cells (b) in culture, in the presence of farnesol, geranylgeraniol or both molecules.

Farnesol, geranylgeraniol, alone or in combination, nullify the effect of the pravastatin+zoledronate treatment on nuclear morphology of Zmpste24$^{-/-}$ cells. Legend of FIG. 17: The pravastatin+zoledronate treatment partially corrects the anomalies in the repair of DNA double-strand breaks (DSBs) in the cells of progeria patients.

Control fibroblasts and fibroblasts from progeria patients were incubated with the pravastatin+zoledronate mixture (1 μM each) or with PBS and were irradiated with X rays (2 Gy). Immunodetection of phosphorylated histone H2AX foci detected 24 hours after irradiation, where the foci correspond to unrepaired double-strand breaks (top images). Nuclear marking with DAPI (bottom images). Bottom graphs: Variation in the number of phosphorylated histone H2AX foci over time after irradiation in control cells (shaded square) and progeria cells (unshaded circle) incubated with PBS or treated with pravastatin+zoledronate. Each curve shows the mean±standard error of the mean from at least 3 experiments.

Combined Pravastatin+Zoledronate Treatment Improves the Progeroid Phenotype of Zmpste24$^{-/-}$ Mice (FIGS. 18, 19 and 20):

The Zmpste24$^{-/-}$ mice and the control mice were treated on a daily basis with pravastatin and zoledronate or a combination of both drugs, at a dose that had previously been shown to be non-toxic in mice. As had already been observed for the cells of progeria patients, neither of the drugs in isolation, pravastatin or zoledronate, increases the lifespan of Zmpste24$^{-/-}$ mice (FIG. 19). However, the combination of both drugs significantly improves the progeroid phenotype of Zmpste24 mice: the treatment leads to improved weight gain, increases the quantity of subcutaneous fat, reduces the scale of kyphosis and alopecia and increases the lifespan. The survival time increased from 101 to 179 days and the maximum survival time increased from 151 to 222 days (P<0.001, FIG. 18c). It should be noted that all phenotype signs corrected by the treatment in mice are also characteristic of progeria in humans. The combined treatment corrects the decrease in bone density, which is one of the characteristics of Zmpste24$^{-/-}$ mice and of patients with progeria or a related progeroid syndrome. Computerised bone microtomography shows an increase in bone mineralisation and an increase in the thickness of the tibial cortex in the treated mice (FIG. 18d). Likewise, the quantification of nuclear morphology in the liver of Zmpste24$^{+/+}$, Zmpste24$^{-/-}$ and treated Zmpste24$^{-/-}$ mice shows that the pravastatin+zoledronate treatment normalises the shape of Zmpste24$^{-/-}$ cell nuclei (FIG. 18e). The treatment also corrects Zmpste24$^{-/-}$ mice (Varela et al., 2005 (54 bis)) (FIG. 18f). Finally, we looked at whether the treatment could have an effect on Lmna$^{-/-}$ mice that cannot accumulate prelamin A. The pravastatin+zoledronate treatment had no effect on the lifespan of these mice (FIG. 20), which provides further evidence that this treatment can only act in mice that accumulate farnelysed prelamin A in the nuclear envelope.

Figure 18:
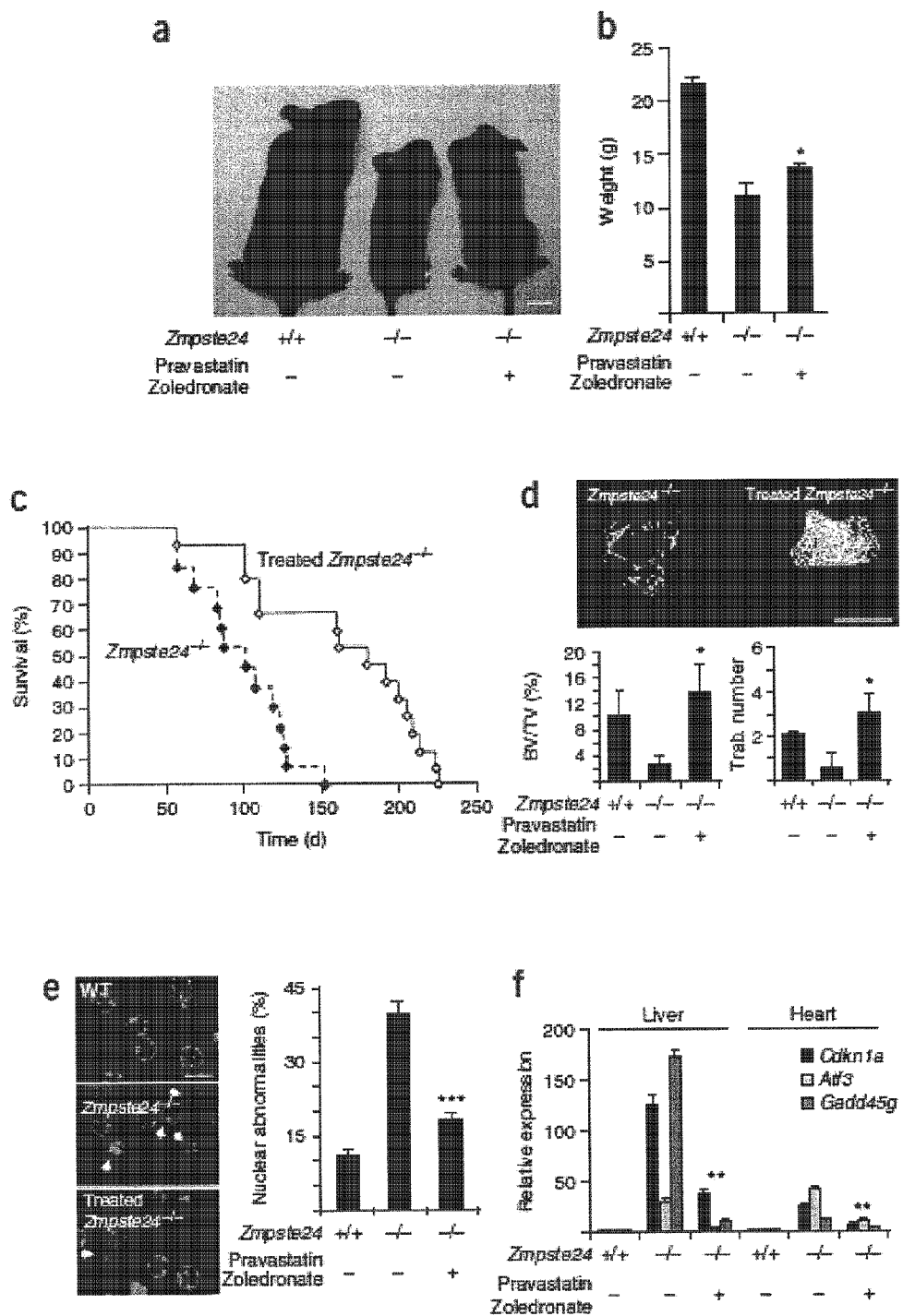
FIG. 18: Effect of the pravastatin+zoledronate treatment on the progeroid phenotype of Zmpste24$^{-/-}$ mice: (a) Photographs representing 3-month-old Zmpste24$^{+/+}$, Zmpste24$^{-/-}$ and Zmpste24$^{-/-}$ mice treated with the pravastatin+zoledronate combination. Scale bar=1 cm. (b) Weight of 3-month-old Zmpste24$^{+/+}$ (n=12), Zmpste24$^{-/-}$ (n=13) and Zmpste24$^{-/-}$ treated (n=15) mice. (c) Kaplan-Meier curves showing a significant increase in the lifespan of Zmpste24$^{-/-}$ treated mice. (d) Three-dimensional representation by computerised microtomography of the tibia of Zmpste24$^{-/-}$ treated and non-treated mice (image at the top). The panel at the bottom represents the relative bone volume and the number of bone trabecules in Zmpste24$^{-/-}$ non-treated and treated mice. (e) Quantification of the nuclear anomalies of the hepatocytes of Zmpste24$^{+/+}$, Zmpste24 and Zmpste24$^{-/-}$ treated mice. The white arrows show the abnormal nuclei. Scale bar=1 µm. (f) Relative expression of the target genes of the p53 in the liver and the heart of Zmpste24$^{+/+}$, Zmpste24$^{-/-}$ and Zmpste24$^{-/-}$ treated mice, analysed by quantitative RT-PCR. * P<0.05;  P<0.01; * P<0.001. The error bars represent the mean±standard error of the mean.
Figure 19:
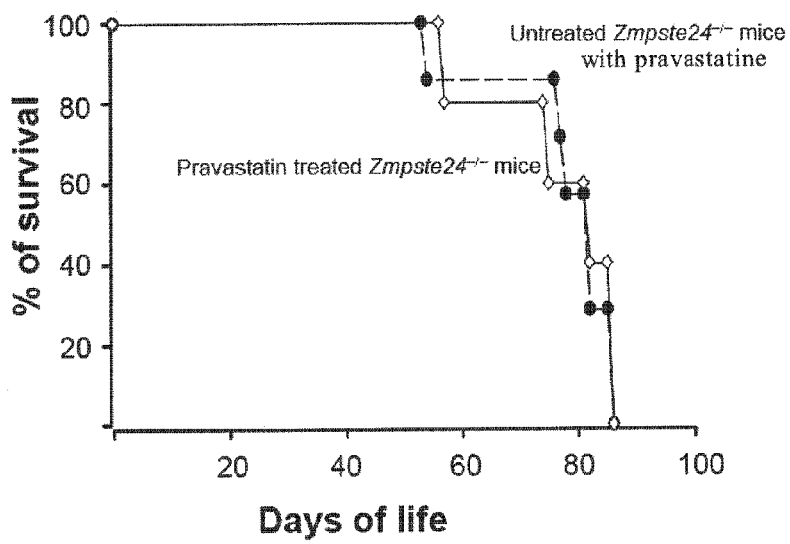
FIG. 19: Effect of the pravastatin alone or of the zoledronate on the lifespan of Zmpste24$^{-/-}$ mice: Kaplan-Meier curves pravastatin only (a) and zoledronate only (b) on Zmpste24$^{-/-}$ treated (empty diamond) and non-treated (solid circles) mice.
Figure 19:
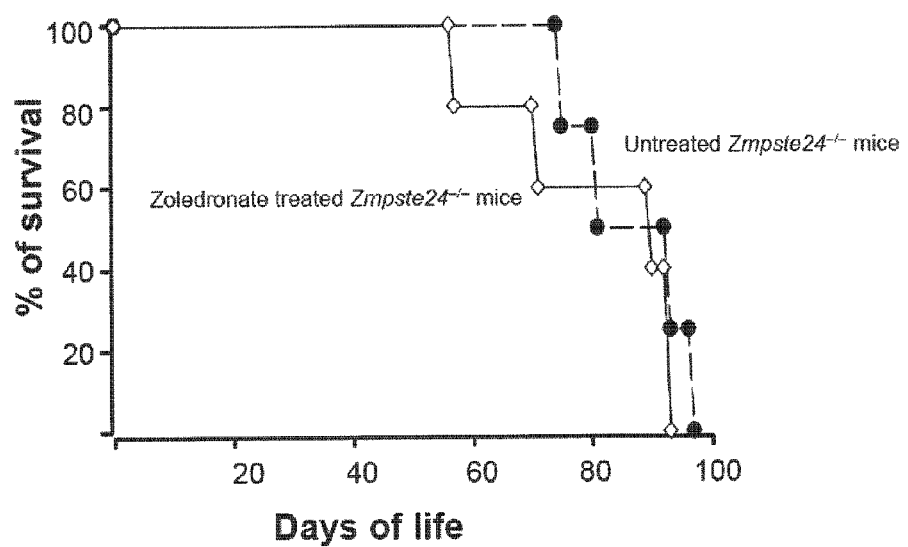

Legend of FIG. 18: The pravastatin+zoledronate treatment improves the progeroid phenotype of Zmpste24$^{-/-}$ mice (a) Photographs showing 3-month old Zmpste24$^{+/+}$ mice, Zmpste24$^{-/-}$ mice and Zmpste24$^{-/-}$ mice treated with a combination of pravastatin (100 mg/kg per day) and zoledronate (100 mg/kg per day). Scale bar=1 cm. (b) Weight of 3-month old Zmpste24$^{+/+}$ (n=12), Zmpste24$^{-/-}$ (n=13) and treated Zmpste24$^{-/-}$ (n=15) mice. (c) Kaplan-Meier curves showing a significant increase in the lifespan of treated Zmpste24$^{-/-}$ (n=15) mice compared with untreated mice (n=13). (d) 3D computerised microtomography representation of the tibia of a treated and untreated Zmpste24$^{-/-}$ mouse (top image). The bottom panel shows the relative bone volume (osseous tissue volume/volume of the tibia) and the number of bone trabeculae in untreated (n=6) and treated (n=5) Zmpste24$^{-/-}$ mice. (e) Quantification of nuclear anomalies in the hepatocytes of Zmpste24$^{+/+}$, Zmpste24$^{-/-}$ and treated Zmpste24$^{-/-}$ mice. The white arrows point to the abnormal nuclei. Scale bar=10 μm. (f) Relative expression of the target genes of the p53 in the liver and the heart of Zmpste24+/+, Zmpste24$^{-/-}$ and Zmpste24$^{-/-}$ treated mice, analysed by quantitative RT-PCR. * P<0.05;  P<0.01; * P<0.001. The error bars represent the mean±standard error of the mean.

Legend of FIG. 19: Neither pravastatin alone, or the zoledronate alone increase the lifespan of the Zmpste24-/- mice:

Kaplan-Meier curves show that the pravastin alone (n=5) (a), and the zoledronate alone (n=5) (b) do not correct the lifespan of the Zmpste24$^{-/-}$ treated (empty diamond) and non-treated (solid circles, n=11) mice.

Figure 20:
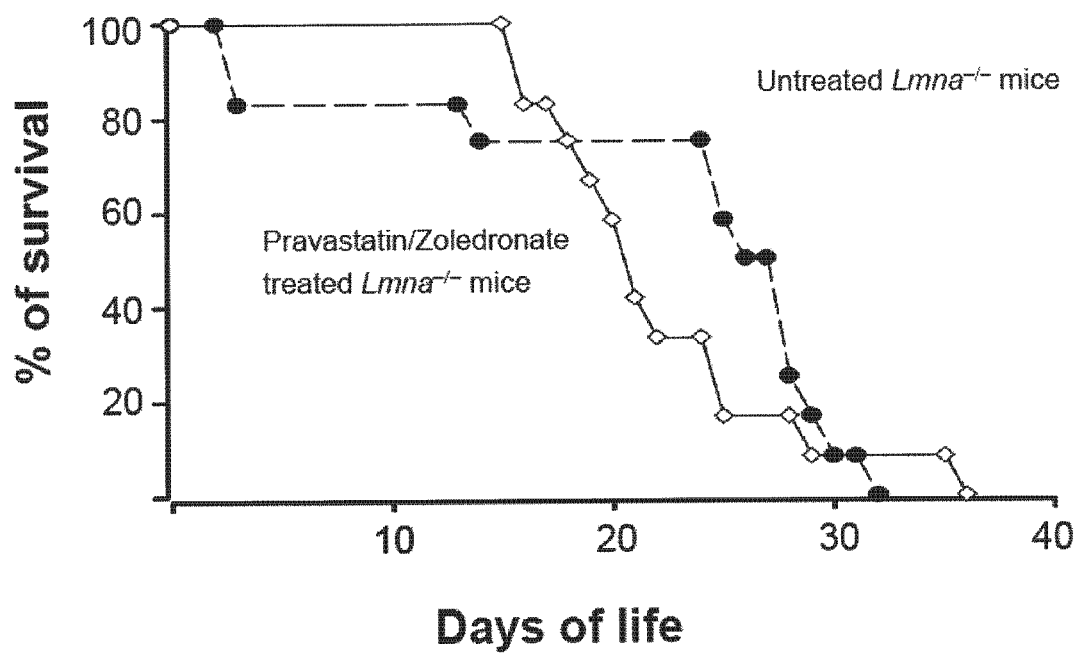
FIG. 20: Effect of a pravastatin+zoledronate treatment on the lifespan of Lmna$^{-/-}$ mice: Kaplan-Meier curves using Lmna$^{-/-}$ mice treated with pravastatin+zoledronate (n=12, empty diamond), compared to that of non-treated mice (solid circles, n=11).

Legend of FIG. 20: The pravastatin+zoledronate treatment does not correct the lifespan of Lmna$^{-/-}$ mice: Kaplan-Meier curves show that the lifespan of Lmna$^{-/-}$ mice treated with pravastatin+zoledronate (n=12, empty diamond), compared to that of non-treated mice (solid circles, n=11). The pravastatin+zoledronate treatment has no effect on mice devoid of lamin A/C.

SUMMARY/CONCLUSION/OUTLOOK

Several human progeroid syndromes, including Hutchinson-Gilford progeria, are caused by the accumulation on the nuclear envelope of a farnesylated form of prelamin A deleted (progerin) or not deleted. The progerin is also produced during the course of physiological aging. Recent studies carried out on cells of patients afflicted with progeria have shown that farnesyl-transferase inhibitors (FTI) improve the morphology of the nuclei, suggesting that these inhibitors could represent a treatment for these devastating syndromes.

The inventors show here that prelamin A and progerin undergo an alternative prenylation via the geranyl-geranyl-transferase when the farnesyl-transferase is inhibited, which could explain the low degree of efficacy of FTI in improving the phenotype of murin models of these progeroid syndromes.

They also show that the combination of a statin and an aminobiphosphonate effectively inhibit the farnesylation as well as the geranyl-geranylation of the prelamin A and of the progerin, significantly improves the phenotype of aging of mice in which has been inactivated the gene coding the metalloprotease Zmpste24 involved in the maturation of the prelamin A. The improvement of the phenotype includes that of the growth curve, weight, lipodystrophy, hair loss and bone anomalies.

In addition, the lifespan of these mice is substantially increased.

This data opens up a new therapeutic approach for human progeroid syndromes with accumulation of prenylated proteins in the nuclear envelope.

The pravastatin+aminobiphosphonate treatment is being applied in Marseille for upcoming 3 years on children afflicted with progeria within the framework of a European therapeutic test (15 children) placed under the responsibility of Nicolas Levy, financed by the Ministry of Health (PHRC 2008) and the French Association against Myopathies (AFM) and which has received authorisation from the AFSSAPS and the South Mediterranean CCP.

The same treatment will soon be given in Rome, under the responsibility of Giuseppe Novelli, to patients afflicted with acromandibular dysplasia, another progeroid syndrome with accumulation of farnesylated prelamin A.

LIST OF REFERENCES (1) Basso A D, Kirschmeier P, Bishop W R. *Farnesyl transferase inhibitors*. J Lipid Res 47:15-31, 2006.
(2) Biamonti G, Giacca M, Perini G, Contreas G, Zentilin L, Weighardt F, Guerra M, Della Valle G, Saccone S, Riva S et al. *The gene for a novel human lamin maps at a highly transcribed locus of chromosome 19 which replicates at the onset of S-phase*. Mol Cell Biol 12:3499-3506, 1992.
(3) Bishop W R, Kirschmeier P, Baun C. *Farnesyl transferase inhibitors: mechanism of action, translational studies and clinical evaluation*. Cancer Biol Ther 2:S96-104, 2003.
(4) Broers J L, Hutchinson C J, Ramaekers F C. *Laminopathies*. J Pathol 204:478-488, 2004.
(5) Broers J L V, Ramaekers F C S, Bonne G, Ben Yaou R, Hutchinson C J. *Nuclear lamins: laminopathies and their role in premature aging*. Physiol Rev 86:967-1008, 2006.
(6) Capell B C, Erdos M R, Madigan J P, Fiordalisi J J, Varga R, Conneely K N, Gordon L B, Der C J, Cox A D, Collins F S. *Inhibiting farnesylation of progerin prevents the characteristic nuclear blabbing of Hutchinson-Gilford progeria syndrome*. Proc Natl Acad Sci USA 102:12879-12884, 2005.
(7) De Sandre-Giovannoli A, Bernard R, Cau P, Navarro C, Amiel J, Boccaccio I, Lyonnet S, Stewart C L, Munnich A, Le Merrer M, Levy N. *Lamin A truncation in Hutchinson-Gilford progeria*. Science 300:2055, 2003.
(8) Demyanets S, Kaun C, Pfaffenberger S, Philipp J. Hohensinner P J, Rega G, Pammer J, Maurer G, Huber K. Wojta J. *Hydroxymethylglutaryl-coenzyme A reductase inhibitors induce apoptosis in human cardiac myocytes in vitro*. Biochem Pharmacol 71:1324-1330, 2006.
(9) Duque G, Rivas D. *Age-related changes in Lamin A/C expression in the osteoarticular system: laminopathies as a potential new aging mechanism*. Mech Aging Dev 127:378-383, 2006.
(10) Efuet E T, Keyomarsi K. *Farnesyl and geranylgeranyl transferase inhibitors induce G1 arrest by targeting the proteasome*. Cancer Res 66:1040-1051, 2006.
(11) Eriksson M, Brown W T, Gordon L B, Glynn M W, Singer J, Scott L, Erdos M R, Robbins C M, Moses T Y, Berglund P, Dutra A, Pak E, Durkin S, Csoka A B, Boehnke M, Glover T W, Collins F S. *Recurrent de novo* point mutation in lamin A cause Hutchinson-Gifford progeria syndrome. Nature 423:293-298, 2003.
(12) Evans M, Rees A. *The myotoxicity of statins*. Cur Op Lipid, 13:415-420, 2002.
(13) Flint O P, Masters B A, Gregg R E, Durham S K, *HMG CoA reductase inhibitor-induced myotoxicity: pravastatin and lovastatin inhibit the geranylgeranylation of low-molecular-weight proteins in neonatal rat muscle cell culture*. Tox Appl Pharmacol 145:99-110, 1997.
(14) Fong L G, Frost D, Meta M, Qiao X, Yang S H, Coffinier C, Young S G. *A protein farnesyltransferase inhibitor ameliorates disease in a mouse model of progeria*. Science, 311:1621-1623, 2006.
(15) Fong L G, Ng J K, Lammerding J, Vickers T A, Meta M, Coté N, Gavino B, Qiao X, Chang S Y, Young S R, Yang S H, Stewart C L, Lee R T, Bennett C F, Bergo M O, Young S G. *Prelamin A and Lamin A appear to be dispensable in the nuclear lamina*. J Clin Invest 116:743-752, 2006.
(16) Fong L G, Ng J K, Meta M, Cote N, Yang S H, Stewart C L, Sullivan T, Burghardt A, Majumdar S, Reue K, Bergo M O, Young S G. *Heterozygosity for Lmna deficiency eliminates the progeria-like phenotypes in Zmpste24-deficient mice*. Proc Natl Acad Sci USA 101:18111-18116, 2004.
(17) Glynn M W, Glover T W. *Incomplete processing of mutant lamin A in Hutchison-Gifford progeria leads to nuclear abnormalities, which are reversed by farnesyl-transferase inhibition*. Hum Mol Genet 14:2959-2969, 2005.
(18) Goldman R D, Shumaker D K, Erdos M R, Eriksson M, Goldman A E, Gordon L B, Gruenbaum Y, Khuon S, Mendez M. Varga R, Collins F S. *Accumulation of mutant lamin A causes progressive changes in nuclear architecture in Hutchinson-Gilford progeria syndrome*. Proc Natl Acad Sci USA 101:8963-8968, 2004.
(19) Gruenbaum Y, Margalit A, Goldman R D, Shumaker D K, Wilson K L. *The nuclear lamina comes of age*. Nat Mol Cell Biol 6:21-31, 2005.
(20) Hampton R, Dimster-Denk D, Rine J. *The biology of HMG-CoA reductase: the pros of contra-regulation*. Trends Biochem Sci 21:140-145, 1996.
(21) Harborth J, Elbashir S M, Bechert K, Tuschl T, Weber K. *Identification of essential genes in cultured mammalian cells using small interfering RNAs*. J Cell Sci 114; 4557-4565, 2001.
(22) Hegele R A, Cao H, Liu D M, Costain G A, Charlton-Menys V, Rodger N W, Durrington P N. *Sequencing of reannotated LMNB2 gene reveals novel mutations in patients with acquired partial lipodystrophy*. Am J Hum Genet 79:383-389, 2006.
(23) Hildebrand T, Ruegsegger P. *A new method for the model independent assessment of thickness in three dimensional images*. J Microsc 185:67-75, 1997.
(24) Hoffmann G F, Charpentier C, Mayatepek E, Mancini J. Leichsenring M, Gibson K M, Divry P, Hrebicek M, Lehnert W, Sartor K. *Clinical and biochemical phenotype in 11 patients with mevalonic aciduria*. Pediatrics 91:915-921, 1993.
(25) Huang S, Chen L, Libina N, Janes J, Martin G M, Campisi J. Oshima J. *Correction of cellular phenotypes of Hutchinson-Gilford Progeria cells by RNA interference*. Hum Genet. 2005 Oct. 6:1-7
(26) Hutchinson C J, Worman H J. *A-type lamins: guardians of the soma?* Nat Cell Biol 6:1062-1067, 2004.
(27) Kusuyama T, Omura T, Nishiya D, Enomoto S, Matsumoto R, Murata T, Takeuchi K, Yoshikawa J, Yoshi-
yama M. *The effects of HMG-CoA reductase inhibitor on vascular progenitor cells*. J Pharmacol Sci 1001:344-349, 2006.
(28) Leung K F, Baron R, Seabra M C. *Geranylgeranylation of Rab GTPases*. J Lipid Res 47:467-475, 2006.
(29) Levy N, Cau P. *Anomalies du noyau et maladies*. Pour la Science 313:2-7, 2003.
(30) Lin F, Worman H J. *Structural organization of the human gene (LMNB1) encoding nuclear lamin B1*. Genomics 27:230-236, 1995.
(31) Lin F, Worman H J. *Structural organization of the human gene encoding nuclear lamin A and nuclear lamin C*. J Biol Chem 268:16321-16326, 1993.
(32) Liu Y, Wang Y, Rusinol A E, Sinensky M S, Liu J, Shell S M, Zou Y. *Involvement of xeroderma pigmentosum group A (XPA) in progeria arising from defective maturation of prelamin A*. FASEB J. 2007 Sep. 11;
(33) Mattout A, Dechat T, Adam S A, Goldman R D, Gruenbaum Y. *Nuclear lamins, diseases and aging*. Cur Op Cell Biol 18:335-341, 2006.
(34) McClintock D, Ratner D, Lokuge M, Owens D M, Gordon L B, Collins F S, Djhabali K. The mutatnt form of lamin A that causes Hutchinbson-Gilford progeria is a biomarker of cellular aging in human skin. PloS One, 2007, 2, e1269
(35) Navarro C L, Cadinanos J, De Sandre-Giovannoli A, Bernard R, Courrier S, Boccaccio I, Boyer A, Kleijer W J, Wagner A, Giuliano F, Beemer F A, Freije J M, Cau P, Hennekam R C, Lopez-Otin C, Badens C, Levy N. *Loss of ZMPSTE24 (FACE-1) causes autosomal recessive restrictive dermopathy and accumulation of Lamin A precursors*. Hum Mol Genet 14:1503-1513, 2005.
(36) Navarro C L, De Sandre-Giovannoli A, Bernard R, Boccaccio I, Boyer A, Genevieve D, Hadj-Rabia S, Gaudy-Marquee C, Smitt H S, Vabres P, Faivre L, Verloes A, Van Essen T, Flori E, Hennekam R, Beemer F A, Laurent N, Le Merrer M, Cau P, Levy N. *Lamin A and ZMPSTE24 (FACE-1) defects cause nuclear disorganization and identify restrictive dermopathy as a lethal neonatal laminopathy*. Hum Mol Genet 13:2483-2503, 2004.
(37) Padiath Q S, Saigoh K, Schiffmann R, Asahara H, Yamada C, Koeppen A, Hogan K. Ptacek L J, Fu Y H. *Lamin B1 duplications cause autosomal dominant leukodystrophy*. Nature Genet 38:1114-1123, 2006.
(38) Pendas A M, Zhou Z, Cadinanos J, Freije J M, Wang J, Hultenby K, Astudillo A, Wernerson A, Rodriguez F, Tryggvason K, Lopez-Olin C. *Defective prelamin A processing and muscular and adipocyte alterations in Zmpste24 metalloproteinase-deficient mice*. Nat Genet 31:94-99, 2002.
(39) Reid T S, Terry K L, Casey P J, Beese L S. *Crystallographic analysis of CaaX prenyltransferases complexed with substrates defines rules of protein substrate selectivity*. J Mol Biol 343:417-433, 2004.
(40) Scaffidi P. Misteli T. *Lamin A-dependent nuclear defects in human aging*. Sciencexpress, 27 avril 2006.
(41) Scaffidi P. Misteli T. *Reversal of the cellular phenotype in the premature aging disease Hutchinson-Gilford progeria syndrome*. Nat Med 11:440-445, 2005.
(42) Scaffidi P, Misteli T, *Reversal of the cellular phenotype in the premature aging disease Hutchinson-Gifford progeria syndrome*. Nature Med 11:440-445, 2005.
(43) Shelton K R, Egle P M, Cochran D L. *Nuclear envelope proteins: identification of lamin B subtypes*. Biochem Biophys Res Comm 103:975-981, 1981.

(44) Shumaker D K, Kuczmarski E R, Goldman R D. *The nucleoskeleton: lamins an actin are major players in essential nuclear functions.* Curr Op Cell Biol 15:358-366, 2003.

(45) Stewart C, Burke B. *Teratocarcinoma stem cells and early mouse embryos contain only a single major lamin polypeptide closely resembling lamin B.* Cell 51:383-392, 1987.

(46) Takedaa M. Noshiroa R, Onozatob M L, Tojob A, Hasannejada H, Huangc X L, Narikawac S, Endoua H. Evidence for a role of human organic anion transporters in the muscular side effects of HMG-CoA reductase inhibitors. Eur J Pharm 483:133-138, 2004.

(47) Toth J I, Yang S H, Qiao X, Beigneux A P, Gelb M H, Moulson C L, Miner J H, Young S G, Fong L G. *Blocking protein farnesyltransferase improves nuclear shape in fibroblasts from humans with progeroid syndromes.* Proc Natl Acad Sci USA 102:12873-12878, 2005.

(48) Tsai M Y, Wang S, Heidinger J M, Shumaker D K, Adam S A, Goldman R D, Zheng Y. *A mitotic lamin B matrix induced by RanGTP required for spindle assembly.* Science 311:1887-1893, 2006.

(49) Varela I, Cadinanos J, Pendas A M, Gutierrez-Fernandez A, Folgueras A R, Sanchez L M, Zhou Z, Rodriguez F J, Stewart C L, Vega J A, Tryggvason K, Freije J M, Lopez-Otin C. *Accelerated ageing in mice deficient in Zmpste24 protease is linked to p53 signalling activation.* Nature 437:564-568, 2005.

(50) Vergnes L, Peterfy M, Bergo M O, Young S G, Reue K. *Lamin B1 is required for mouse development and nuclear integrity.* Proc Natl Acad Sci USA 101:10428-10433, 2004.

(51) Winter-Vann A M, Casey P J. *Post-prenylation-processing enzymes as new targets in oncogenesis.* Nat Rev Cancer 5:405-412, 2005.

(52) Wydner K L, McNeil J A, Lin F, Worman H J, Lawrence J B. *Chromosomal assignment of human nuclear envelope protein genes LMNA, LMNB1 and LBR by fluorescence in situ hybridization.* Genomics 32:474-478, 1996.

(53) Young S G, Meta M, Yang S H, Fong L G, *Prelamin A farnesylation and progeroid syndromes.* J Biol Chem 281:39741-39745, 2006.

(54) Zastrow M S, Vlcek S. Wilson K L. *Proteins that bind A-type lamins: integrating isolated clues.* J Cell Sci 117:979-987, 2004.

(54 bis) Varela, I. Pereira, S ulgade, A. P. Navarro, C. L. Suarez, M. F. Cau, P. Cardinanos, J. Osorio, F. G. Foray, N. Cobo, J. de Carlos, F. Levy, N. Freije, J M. Lopez-Otin, C. Combined treatment with statins and aminobisphosphonates extends longevity in a mous model of human premature aging. Nature Medecine 14: 767-772, 208

HIV

(55) Achanta, G., R. Sasaki, L. Feng, J. S. Carew, W. Lu, H. Pelicano, M. J. Keating, and P. Huang. 2005. Novel role of p53 in maintaining mitochondrial genetic stability through interaction with DNA Pol gamma. *Embo J.* 24:3482-92.

(56) Adler, A. S., S. Sinha, T. L. Kawahara, J. Y. Zhang, E. Segal, and H. Y. Chang. 2007. Motif module map reveals enforcement of aging by continual NF-{kappa}B activity. *Genes Dev.* 21:3244-57.

(57) Agarwal, A. K., J. P. Fryns, R. J. Auchus, and A. Garg. 2003. Zinc metalloproteinase, ZMPSTE24, is mutated in mandibuloacral dysplasia. *Hum Mol Genet.* 12:1995-2001.

(58) Azzam, R., L. Lal, S. L. Goh, K. Kedzierska, A. Jaworowski, E. Naim, C. L. Cherry, S. L. Wesselingh, J. Mills, and S. M. Crowe. 2006. Adverse effects of antiretroviral drugs on HIV-1-infected and -uninfected human monocyte-derived macrophages. *J Acquir Immune Defic Syndr.* 42:19-28.

(59) Balaban, R. S., S. Nemoto, and T. Finkel. 2005. Mitochondria, oxidants, and aging. *Cell.* 120:483-95.

(60) Barbaro, G. 2003. Pathogenesis of HIV-associated cardiovascular disease. *Adv Cardiol.* 40:49-70.

(61) Bartke, A. 2005. Minireview: role of the growth hormone/insulin-like growth factor system in mammalian aging. *Endocrinology.* 146:3718-23.

(62) Bartoli, M., andI. Richard. 2005. Calpains in muscle wasting. *Int J Biochem Cell Biol.* 37:2115-33.

(63) Bauer, J. H., and S. L. Helfand. 2006. New tricks of an old molecule: lifespan regulation by p53. *Aging Cell.* 5:437-40.

(64) Baxter, J. D., J. M. Schapiro, C. A. Boucher, V. M. Kohlbrenner, D. B. Hall, J. R. Scherer, and D. L. Mayers. 2006. Genotypic changes in human immunodeficiency virus type 1 protease associated with reduced susceptibility and virologic response to the protease inhibitor tipranavir. *J Virol.* 80:10794-801.

(65) Ben-Porath, I., and R. A. Weinberg. 2005. The signals and pathways activating cellular senescence. *Int J Biochem Cell Biol.* 37:961-76.

(66) Bender, A, K. J. Krishnan, C. M. Morris, G. A. Taylor, A. K. Reeve, R. H. Perry, E. Jaros, J. S. Hersheson, J. Betts, T. Klopstock, R. W. Taylor, and D. M. Turnbull. 2006. High levels of mitochondrial DNA deletions in substantia nigra neurons in aging and Parkinson disease. *Nat Genet.* 38:515-7.

(67) Benesic, A., M. Zilly, F. Kluge, B. Weissbrich, R. Winzer, H. Klinker, and P. Langmann. 2004. Lipid lowering therapy with fluvastatin and pravastatin in patients with HIV infection and antiretroviral therapy: comparison of efficacy and interaction with indinavir. *Infection.* 32:229-33.

(68) Bensaad, K., and K. H. Vousden. 2005. Savior and slayer: the two faces of p53. *Nat Med.* 11:1278-9.

(69) Bordone, L., and L. Guarente. 2005. Calorie restriction, SIRT1 and metabolism: understanding longevity. *Nat Rev Mol Cell Biol.* 6:298-305.

(70) Bourlier, V., A. Zakaroff-Girard, S. De Barros, C. Pizzacalla, V. D. de Saint Front, M. Lafontan, A. Bouloumie, and J. Galitzky. 2005. Protease inhibitor treatments reveal specific involvement of matrix metalloproteinase-9 in human adipocyte differentiation. *J Pharmacol Exp Ther.* 312:1272-9,

(71) Broers, J. L., F. C. Ramaekers, G. Bonne, R. B. Yaou, and C. J. Hutchison. 2006. Nuclear lamins: laminopathies and their role in premature ageing. *Physiol Rev.* 86:967-1008.

(72) Brokstad, K. A., K. Kalland, W. C. Russell, and D. A. Matthews. 2001. Mitochondrial protein p32 can accumulate in the nucleus. *Biochem Biophys Res Commun.* 281:1161-9,

(73) Brosh, R. M., Jr., P. Karmakar, J. A. Sommers, Q. Yang, X. W. Wang, E. A. Spillare, C. C. Harris, and V. A. Bohr. 2001. p53 Modulates the exonuclease activity of Werner syndrome protein. *J Biol Chem.* 276:35093-102.

(74) Brown, T. T., and R. B. Qaqish. 2006. Antiretroviral therapy and the prevalence of osteopenia and osteoporosis: a meta-analytic review. *Aids.* 20:2165-74.

(75) Bukrinsky, M., and D. Sviridov. 2006. Human immunodeficiency virus infection and macrophage cholesterol metabolism. *J Leukoc Biol.* 80:1044-51.

(76) Calvo, S., M. Jain, X. Xie, S. A. Sheth, B. Chang, O. A. Goldberger, A. Spinazzola, M. Zeviani, S. A. Carr, and V. K. Mootha. 2006. Systematic identification of human mitochondrial disease genes through integrative genomics. *Nat Genet.* 38:576-82.

(77) Campisi, J. 2004. Fragile fugue: p53 in aging, cancer and IGF signaling. *Nat Med.* 10:231-2.

(78) Cao. K., B. C. Capell, M. R. Erdos, K. Djabali, and F. S. Collins. 2007. A lamin A protein isoform overexpressed in Hutchinson-Gilford progeria syndrome interferes with mitosis in progeria and normal cells. *Proc Natl Acad Sci USA.* 104:4949-54.

(79) Capeau, J., J. Magre, O. Lascols, M. Caron, V. Bereziat, C. Vigouroux, and J. P. Bastard. 2005. Diseases of adipose tissue: genetic and acquired lipodystrophies. *Biochem Soc Trans.* 33:1073-7.

(80) Caron, M., M. Auclair, B. Donadille, V. Bereziat, B. Guerci, M. Laville, H. Narbonne, C. Bodemer, O. Lascols, J. Capeau, and C. Vigouroux. 2007. Human lipodystrophies linked to mutations in A-type lamins and to HIV protease inhibitor therapy are both associated with prelamin A accumulation, oxidative stress and premature cellular senescence. *Cell Death Differ.* 14:1759-67.

(81) Caron, M., M. Auclair, H. Sterlingot, M. Kornprobst, and J. Capeau. 2003. Some HIV protease inhibitors alter lamin A/C maturation and stability, SREBP-1 nuclear localization and adipocyte differentiation. *Aids.* 17:2437-44,

(82) Caron, M., M. Auclair, C. Vigouroux, M. Glorian, C. Forest and J. Capeau. 2001. The HIV protease inhibitor indinavir impairs sterol regulatory element-binding protein-1 intranuclear localization, inhibits preadipocyte differentiation, and induces insulin resistance. *Diabetes.* 50:1378-88.

(83) Casau, N. C. 2005. Perspective on HIV infection and aging: emerging research on the horizon. *Clin Infect Dis.* 41:855-63,

(84) Cawthon, R. M. 2002. Telomere measurement by quantitative PCR. *Nucleic Acids Res.* 30:e47.

(85) Chattopadhyay, C., D. Hawke, R. Kobayashi, and S. N. Malty. 2004. Human p32, interacts with B subunit of the CCAAT-binding factor, CBF/NF-Y, and inhibits CBF-mediated transcription activation in vitro. *Nucleic Acids Res.* 32:3632-41.

(86) Chen, C., X. H. Lu, S. Yan, H. Chai, and Q. Yao. 2005. HIV protease inhibitor ritonavir increases endothelial monolayer permeability. *Biochem Biophys Res Commun.* 335:874-82.

(87) Chen, C. D., S. Podvin, E. Gillespie, S. E. Leeman, and C. R. Abraham. 2007. Insulin stimulates the cleavage and release of the extracellular domain of Klotho by ADAM10 and ADAM17. *Proc Natl Acad Sci USA.* 104: 19796-801.

(88) Coffinier, C., S. E. Hudon, E. A. Farber, S. Y. Chang, C. A. Hrycyna, S. G. Young, and L. G. Fong. 2007. HIV protease inhibitors block the zinc metalloproteinase ZMP-STE24 and lead to an accumulation of prelamin A in cells. *Proc Natl Acad Sci USA.* 104:13432-7.

(89) Cohan, G. R. 2006. HIV-associated hypogonadism. *AIDS Read.* 16:341-5, 348, 352-4.

(90) Colgan, S. M., D. Tang, G. H. Werstuck, and R. C. Austin, 2007. Endoplasmic reticulum stress causes the activation of sterol regulatory element binding protein-2. *Int J Biochem Cell Biol.* 39:1843-51.

(91) Costelli, P., and F. M. Baccino. 2003. Mechanisms of skeletal muscle depletion in wasting syndromes: role of ATP-ubiquitin-dependent proteolysis. *Curr Opin Clin Nutr Metab Care.* 6:407-12.

(92) Costelli, P., P. Reffo, F. Penna, R. Autelli, G. Bonelli, and F. M. Baccino. 2005. Ca(2+)-dependent proteolysis in muscle wasting. *Int J Biochem Cell Biol.* 37:2134-46.

(93) Csoka, S. B. English, C. P. Simkevich, D. C. Ginzinger, A. J. Butte, G. P. Schatten, F. G. Rothman, and J. M. Sedivy. 2004. Genome-scale expression profiling of Hutchinson-Gilford progeria syndrome reveals widespread transcriptional misregulation leading to mesodermal/mesenchymal defects and accelerated atherosclerosis. *Aging Cell.* 3:235-43.

(94) De Barros. S. A Zakaroff-Girard, M. Lafontan, J. Galtzky, and V. Bourier. 2007. Inhibition of human preadipocyte proteasomal activity by HIV protease inhibitors or specific inhibitor lactacystin leads to a defect in adipogenesis, which involves matrix metalloproteinase-9. *J Pharmacol Exp Ther.* 320:291-9.

(95) de Noronha, C. M., M. P. Sherman, H. W. Lin, M. V. Cavrois, R. D. Moir, R. D. Goldman, and W. C. Greene. 2001. Dynamic disruptions in nuclear envelope architecture and integrity induced by HIV-1 Vpr. *Science.* 294: 1105-8.

(96) de Oliveira, R. M. 2006. Klotho RNAi induces premature senescence of human cells via a p53/p21 dependent pathway. *FEBS Left.* 580:5753-8.

(97) de Saint Martin, L., O. Vandhuick, P. Guillo, V. Bellein, L. Bresollette, N. Roudaut, A. Amaral, and E. Pasquier. 2006. Premature atherosclerosis in HIV positive patients and cumulated time of exposure to antiretroviral therapy (SHIVA study). *Atherosclerosis.* 185:361-7.

(98) De Sandre-Giovannoli, A., R. Bernard, P. Cau, C. Navarro, J. Amiel, I. Boccaccio, S. Lyonnet, C. L Stewart, A. Munnich, M. Le Merrer, and N. Levy. 2003. Lamin a truncation in Hutchinson-Gilford progerfa. *Science.* 300: 2055.

(99) Dechat, T., T. Shimi, S. A. Adam, A E. Rusinol. D. A. Andres, H. P. Spielmann. M. S. Sinensky, and R. D. Goldman. 2007. Alterations in mitosis and cell cycle progression caused by a mutant lamin A known to accelerate human aging. *Proc Natl Acad Sc USA.* 104:4955-860.

(100) Dixit. V., N. Hariparsad, F. Li, P. Desal, K. E. Thummel, and J. D. Unadkat. 2007. Cytochrome P450 enzymes and transporters induced by anti-human immunodeficiency virus protease inhibitors in human hepatocytes: implications for predicting clinical drug interactions. *Drug Metab Dispos.* 35:1853-9.

(101) Dressman, J., J. Kincer, S. V. Matveev, L. Guo, R. N. Greenberg, T. Guerin, D. Meade, X. A. U, W. Zhu. A. Uittenbogaard, M. E. Wilson, and E. J. Smart. 2003. HIV protease inhibitors promote atherosclerotic lesion formation independent of dyslipidemia by increasing CD36-dependent cholesteryl ester accumulation in macrophages. *J Clin Invest.* 111:389-97.

(102) Dunn. B. M., M. M. Goodenow, A Gustchina, and A. Wlodawer. 2002. Retroviral proteases. *Genome Biol.* 3:REVIEWS3006.

(103) Effros, R. B. 2000. Telomeres and HIV disease. *Microbes Infect.* 2:69-76.

(104) Eriksson, M., W. T. Brown, L. B. Gordon, M. W. Glynn. J. Singer, L. Scott, M. R. Erdos, C. M. Robbins, T. Y. Moses. P. Berglund. A. Dutra. E. Pak. S. Durkin, A. B. Csoka, M. Boehnke, T. W. Glover, and F. S. Collins. 2003.

Recurrent de novo point mutations in lamin A cause Hutchinson-Gilford progeria syndrome. *Nature.* 423:293-8.
(105) Ferreira. C. E., A. M. Pinto-Neto, D. M. Conde, L. Costa-Paiva. S. S. Morais, and J. Magalhaes. 2007. Menopause symptoms in women infected with HIV: prevalence and associated factors. *Gynecol Endocrinol.* 23:198-205.
(106) Fuster, J. J., S. M. Sanz-Gonzalez, U. M. Moll, and V. Andres. 2007. Classic and novel roles of p53: prospects for anticancer therapy. *Trends Mol Med.* 13:192-9.
(107) Gharakhanian, S., F. Boccara, and J. Capeau. 2006. Statins in HIV-associated lipodystrophy and metabolic syndrome: is them a missing ink? *Aids.* 20:1061-3.
(108) Ghibelli, L., F. Mengoni, M. Lichtner, S. Coppola, M. De Nicola, A. Bergamaschi, C. Mastroianni, and V. Vullo. 2003. Anti-apoptotic effect of HIV protease inhibitors via direct inhibition of calpain. *Biochem Pharmacol.* 66:1505-12.
(109) Gil, M. E., and T. L Coetzer. 2004. Real-time quantitative PCR of telomere length. *Mol Biotechnol.* 27:169-72.
(110) Gilson, E., and V. Gell. 2007. How telomeres are replicated. *Nat Rev Mol Cell Bol.* 8:825-38.
(111) Giorgio, M., E. Migliaccio, F. Orsini, D. Paolucci, M. Moroni, C. Contursi, G. Pellicca, L. Luzi, S. Minucci, M. Marcaccio, P. Pinton, R. Rizzuto, P. Bernardi, F. Paolucci, and P. G. Pelicci. 2005. Electron transfer between cytochrome c and p66Shc generates reactive oxygen species that trigger mitochondrial apoptosis. *Cell.* 122: 221-33.
(112) Giorgio, M., M. Trine, E. Migliaccio, and P. G. Pelicci. 2007. Hydrogen peroxide: a metabolic by-product or a common mediator of ageing signals?*Nat Rev Mol Cell Biol.* 8:722-8.
(113) Glass. D. J. 2003. Signalling pathways that mediate skeletal muscle hypertrophy and atrophy. *Nat Cell Biol.* 5:87-90.
(114) Goldman, R. D., D. K. Shumaker, M. R. Erdos, M. Eriksson, A. E. Goldman, L. B. Gordon, Y. Gruenbaum, S. Khuon, M. Mendez, R. Varga, and F. S. Collins. 2004. Accumulation of mutant lamin A causes progressive changes in nuclear architecture in Hutchinson-Gilford progeria syndrome. *Proc Natl Acad Sci USA.* 101:8963-8.
(115) Granfors, M. T., J. S. Wang, L. I. Kajosaari, J. Laitila, P. J. Neuvonen, and J. T. Backman. 2006. Differential inhibition of cytochrome P450 3A4, 3A5 and 3A7 by five human immunodeficiency virus (HIV) protease inhibitors in vitro. *Basic Clin Pharmacol Toxicol.* 98:79-85.
(116) Graziewicz, M. A., B. J. Day, and W. C. Copeland. 2002. The mitochondrial DNA polymerase as a target of oxidative damage. *Nucleic Acids Res.* 30:2817-24.
(117) Gredilla, R., and G. Barja. 2005. Minireview: the role of oxidative stress in relation to caloric restriction and longevity. *Endocrinology.* 146:3713-7.
(118) Grillari, J., H. Katinger, and R. Voglauer. 2006. Aging and the ubiquitinome: traditional and non-traditional functions of ubiquitin in aging cells and tissues. *Exp Gerontol.* 41:1067-79.
(119) Guarente, L., and F. Picard. 2005. Calorie restriction— the SIR2 connection. *Cell.* 120:473-82.
(120) Gupta, A. K., G. J. Cerniglia, R. Mick, W. G. McKenna, and R. J. Muschel. 2005. HIV protease inhibitors block Aid signaling and rediosensitize tumor cells both in vitro and in vivo. *Cancer Res.* 65:8256-65.
(121) Hamel, F. G., J. Fawcett. B. T. Tsui, R. G. Bennett, and W. C. Duckworth. 2006. Effect of nelfinavir on insulin metabolism, proteasome activity and protein degradation in HepG2 cells. *Diabetes Obes Metab.* 8:661-8.
(122) Hardy, K., L. Mansfield, A. Mackay, S. Benvenuti, S. Ismail, P. Arora, M. J. O'Hare, and P. S. Jat. 2005. Transcriptional networks and cellular senescence in human mammary fibroblasts. *Mol Biol Cell.* 16:943-53.
(123) Hayden, M. S., and S. Ghosh. 2004. Signaling to NF-kappaB. *Genes Dev.* 18:2195-224.
(124) Heessen. S., and M. Fornerod. 2007. The inner nuclear envelope as a transcription factor resting place. *EMBO Rep.* 8:914-9.
(125) Helton, E. S., and X. Chen. 2007. p53 modulation of the DNA damage response. *J Cell Biochem.* 100:883-96.
(126) Hennekam, R. C. 2006. Hutchinson-Gilford progeria syndrome: Review of the phenotype. *Am J Med Genet A.*
(127) Hertel, J., H. Struthers, C. B. Horj, and P. W. Hruz. 2004. A structural basis for the acute effects of HIV protease inhibitors on GLUT4 intrinsic activity. *J Biol Chem.* 279:55147-52.
(128) Holzenberger, M., L Kappeler, and C. De Magalhaes Filho. 2004. IGF-1 signaling and aging. *Exp Gernotol.* 39:1761-4.
(129) Hruz, P. W. 2006. Molecular Mechanisms for Altered Glucose Homeostasis in HIV Infection. *Am J Infect Dis.* 2:187-192.
(130) Huang. S., R. A. Risques, G. M. Martin, P. S. Rabinovitch, and J. Oshima. 2008. Accelerated telomere shortening and replicative senescence in human fibroblasts overexpressing mutant and wild-type lamin A. *Exp Cell Res.* 314:82-91.
(131) Hudson, G., and P. F. Chinnery. 2006. Mitochondrial DNA polymerase-gamma and human disease. *Hum Mol Genet.* 15 Spec No 2:R244-52.
(132) Hui, D. Y. 2003. Effects of HIV protease inhibitor therapy on lipid metabolism. *Prog Lipid Res.* 42:81-92.
(133) Irminger-Finger, I. 2007. Science of cancer and aging. *J Clin Oncol.* 25:1844-51.
(134) Jacque. J. M., and M. Stevenson. 2006. The inner-nuclear-envelope protein emerin regulates HIV-1 infectivity. *Nature.* 441:641-5.
(135) Jiang, B., V. Y. Hebert, Y. Li, J. M. Mathis, J. S. Alexander, and T. R. Dugas. 2007. HIV antiretroviral drug combination induces endothelial mitochondrial dysfunction and reactive oxygen species production, but not apoptosis. *Toxicol Appl Pharmacol.* 224:60-71.
(136) Jiang, B., V. Y. Hebert, J. H. Zavecz, and T. R. Dugas. 2006. Antiretrovirals induce direct endothelial dysfunction in vivo. *J Acquir Immune Defic Syndr.* 42:391-5.
(137) Jiang. J., Y. Zhang, A. R. Krainer, and R. M. Xu. 1999. Crystal structure of human p32, a doughnut-shaped acidic mitochondrial matrix protein. *Proc Natl Acad Sci USA.* 96:3572-7.
(138) John. M., C. B. Moore, I. R. James, D. Nolan, R. P. Upton, E. J. McKinnon, and S. A. Mallal. 2001. Chronic hyperlactatemia in HIV-infected patients taking antiretroviral therapy. *Aids.* 15:717-23.
(139) Jones, R., S. Sawleshwarkar, C. Michailidis, A. Jackson, S. Mandalia, J. Stebbing, M. Bower, M. Nelson, B. G. Gazzard, and G. J. Moyle. 2005. Impact of antiretroviral choice on hypercholesterolaemia events: the role of the nucleoside reverse transcriptase inhibitor backbone. *HIV Med.* 6:396-402.
(140) Kenyon. C. 2005. The plasticity of aging: insights from long-lived mutants. *Cell.* 120:449-60.
(141) Kim, K. S., Y. B. Seu, S. H. Baek. M. J. Kim, K. J. Kim, J. H. Kim, and J. R. Kim. 2007. Induction of cellular (141) ...senescence by insulin-like growth factor binding protein-5 through a p53-dependent mechanism. *Mol Biol Cell.* 18:4543-52.

(142) Kim, R. J., C. G. Wilson, M. Wabitsch, M A. Lazar, and C. M. Steppan. 2006. HIV protease inhibitor-specific alterations in human adipocyte differentiation and metabolism. *Obesity (Silver Spring).* 14:994-1002.

(143) Kohler, J. J., and W. Lewis. 2007. A brief overview of mechanisms of mitochondrial toxicity from NRTIs. *Environ Mol Mutagen.* 48:166-72.

(144) Krahn, M., A. Lopez de Munain, N. Streichenberger. R. Bernard, C. Pecheux, H. Testard, J. L Pena-Segura, E. Yoldi, A. Cabello, N. B. Romero. J. J. Poza, S. Bouillot-Emer, X. Ferrer, M. Goicoechea, F. Garcia-Bragado, F. Leturcq, J. A. Urtizberea, and N. Levy. 2006. CAPN3 mutations in patients with idiopathic eosinophilic myositis. *Ann Neurol.* 59:905-11.

(145) Kraytsberg, Y., E. Kudryavtseva, A. C. McKee, C. Geula, N. W. Kowall, and K. Khrapko. 2006. Mitochondrial DNA deletions are abundant and cause functional impairment in aged human substantia nigra neurons. *Nat Genet.* 38:518-20.

(146) Kudlow, B. A., B. K. Kennedy, and R. J. Monnat, Jr. 2007. Werner and Hutchinson-Gilford progeria syndromes: mechanistic basis of human progeroid diseases. *Nat Rev Mol Cell Biol.* 8:394-404.

(147) Kujoth, G. C., A. Hiona, T. D. Pugh, S. Someya, K. Panzer, S. E. Wohlgemuth, T. Hofer, A. Y. Seo, R. Sullivan, W. A. Jobling, J. D. Morrow, H. Van Remmen, J. M. Sedivy, T. Yamasoba, M. Tanokura, R. Weindruch, C. Leeuwenburgh, and T. A. Prolla. 2005. Mitochondrial DNA mutations, oxidative stress, and apoptosis in mammalian aging. *Science.* 309:481-4.

(148) Kuro-o, M., Y. Matsumura, H. Aizawa, H. Kawaguchi, T. Suga. T. Utsugi, Y. Ohyama, M. Kurabayashi, T. Kaname, E. Kume, H. Iwasaki, A. lida, T. Shiraki-lida, S. Nishikawa, R. Nagai, and Y. I. Nabeshima. 1997. Mutation of the mouse klotho gene leads to a syndrome resembling ageing. *Nature.* 390:45-51.

(149) Kurosu, H., Y. Ogawa, M. Miyoshi, M. Yamamoto, A Nandi, K. P. Rosenblatt, M. G. Baum, S. Schiavi, M. C. Hu, O. W. Moe, and M. Kuro-o. 2006. Regulation of fibroblast growth factor-23 signaling by klotho. *J Biol Chem.* 281:6120-3.

(150) Kurosu, H., M. Yamamoto, J. D. Clark, J. V. Pastor, A Nandi, P. Gurnani, O. P. McGuinness, H. Chikuda, M. Yamaguchi, H. Kawaguchi, I. Shimomura, Y. Takayama, J. Herz, C. R. Kahn, K. P. Rosenblatt, and M. Kuro-o. 2005. Suppression of aging in mice by the hormone Klotho. *Science.* 309:1829-33.

(151) Lactic Acidosis International Study Group. 2007. Risk factors for lactic acidosis and severe hyperlactataemia in HIV-1-infected adults exposed to antiretroviral therapy. *Aids.* 21.2455-64.

(152) Lee, S., S. Y. Jeong, W. C. Lim, S. Kim, Y. Y. Park, X. Sun, R. J. Youle, and H. Cho. 2007. Mitochondrial fission and fusion mediators, hFis1 and OPA1, modulate cellular senescence. *J Biol Chem.* 282:22977-83.

(153) Levy, J. A. M. G. Ory, and S. Crystal. 2003. HIV/AIDS interventions for midlife and older adults: current status and challenges. *J Acquir Immune Defic Syndr.* 33 Suppl 2:S59-67.

(184) Lewis, W. 2003. Defective mitochondrial DNA replication and NRTIs: pathophysiological implications in AIDS cardiomyopathy. *Am J Physiol Heart Circ Physiol.* 284:H1-9.

(155) Liang, S. L, H. Liu, and A. Zhou. 2006. Lovastatin-induced apoptosis in macrophages through the Rac1/Cdc42/JNK pathway. *J Immunol.* 177:651-6.

(156) Lichtner. M., F. Mengoni. C. M. Mastroianni, I. Sauzullo, R. Rossi. M. De Nicola, V. Vullo, and L. Ghibelli. 2006. HIV protease inhibitor therapy reverses neutrophil apoptosis in AIDS patients by direct calpain inhibition. *Apoptosis.* 11:781-7.

(157) Liu, B., J. Wang, K. M. Chan, W. M. Tjia, W. Deng, X. Guan, J. D. Huang, K. M. Li, P. Y. Chau, D. J. Chen, D. Pei, A. M. Pendas, J. Cadinanos, C. Lopez-Otin, H. F. Tse, C. Hutchison, J. Chen, Y. Cao, K. S. Cheah, K. Tryggvason, and Z. Zhou. 2005. Genomic instability in laminopathy-based premature aging. *Nat Med.* 11:780-5.

(158) Liu. H., M. M. Fergusson, R. M. Castilho, J. Liu, L. Cao, J. Chen, D. Malide, Rovira, II, D. Schimel, C. J. Kuo, J. S. Gutkind, P. M. Hwang, and T. Finkel. 2007a. Augmented Wnt signaling in a mammalian model of accelerated aging. *Science.* 317:803-6.

(159) Liu. Y., A Rusinol, M. Sinensky, Y. Wang, and Y. Zou. 2006. DNA damage responses in progeroid syndromes arise from defective maturation of prelamin A. *J Cell Sci.* 119:4844-9.

(180) Liu. Y., Y. Wang. A. E. Rusinol, M. S. Sinensky, J. Liu, S. M. Shell, and Y. Zou. 2007b. Involvement of aeroderma pigmentosum group A (XPA) in progeria arising from defective maturation of prelamin A. *Faseb J.*

(161) Lizzi, A. R., A M. D'Alessandro, A. Bozzi, B. Cinque, A. Oratore, and G. D'Andrea. 2007. Pattern expression of glycan residues in AZT-treated K562 cells analyzed by lectin cytochemistry. *Mol Cell Biochem.* 300:29-37.

(162) Mallon, P. W., J. Miller, J. C. Kovacic, J. Kent-Hughes, R. Norris, K. Samaras, M. P. Feneley, D. A. Cooper, and A. Carr. 2006. Effect of pravastatin on body composition and markers of cardiovascular disease in HIV-infected men—a randomized, placebo-controlled study. *Aids.* 20:1003-10.

(163) Manfredi, J. J. 2003. p53 and apoptosis: its not just in the nucleus anymore. *Mol Cell.* 11:552-4.

(164) Martin, F. M., and J. S. Friedman. 2004. Ticking fast or ticking slow, through She must you go? *Sci Aging Knowledge Environ.* 2004:pe32.

(165) Martin, G. M., and L. A. Loeb. 2004. Ageing: mice and mitochondria. *Nature.* 429:357-9.

(166) Masoro, E. J. 2004. Role of sirtuin proteins in life extension by caloric restriction. *Mech Ageing Dev.* 125: 591-4.

(167) Matarrese. P., L. Gambardella, A. Cassone, S. Vella, R. Cauda, and W. Malorni. 2003. Mitochondrial membrane hyperpolarization hijacks activated T lymphocytes toward the apoptotic-prone phenotype: homeostatic mechanisms of HIV protease inhibitors. *J Immunol.* 170:6006-15.

(168) Matarrese. P., A. A Tinari, L Gambardella, E. Mormone, P. Narilli, M. Pierdominici, R. Cauda, and W. Malorni. 2005. HIV protease inhibitor prevent mitochondrial hyperpolarizaton and redox imbalance and decrease endogenous uncoupler protein-2 expression in gp 120-activated human T lymphocytes. *Antivir Ther.* 10 Suppl 2:M29-45.

(169) Matoba, S., J. G. Kang, W. D. Patino, A. Wragg, M. Boehm, O. Gavnlova, P. J. Hurley, F. Bunz, and P. M. Hwang. 2006. p53 regulates mitochondrial respiration. *Science.* 312:1650-3.

(170) Maurer. T. A. 2005. Dermatologic manifestations of HIV infection. *Top HIV Med.* 13:149-54.

(171) Mehta, I. S., M. Figgitt, C. S. Clements, I. R. Kill, and J. M. Bridget. 2007. Alterations to nuclear architecture and genome behavior in senescent cells. *Ann N Y Acad Sci.* 1100:250-63.

(172) Meissner, C. 2007. Mutations of mitochondrial DNA—cause or consequence of the ageing process? *Z Gerontol Geriatr.* 40:325-333.

(173) Migliaccio. E., M. Giorgio, S. Mele, G. Pelicci, P. Reboldi, P. P. Pandolfi, L. Lanfrancone, and P. G. Pelicci. 1999. The p66shc adaptor protein controls oxidative stress response and life span in mammals. *Nature.* 402:309-13.

(174) Migliaccio, E., M. Giorgio, and P. G. Pelicci. 2006. Apoptosis and aging: role of p66Shc redox protein. *Antioxid Redox Signal.* 8:600-8.

(175) Mihara, M., S. Erster, A. Zaika, O. Petrenko, T. Chittenden, P. Pancoska, and U. M. Moll. 2003. p53 has a direct apoptogenic role at the mitochondria. *Mol Cell.* 11:577-90.

(176) Miserez, A. R., P. Y. Muller, and V. Spaniol. 2002. Indinavir inhibits sterol-regulatory element-binding protein-1c-dependent lipoprotein lipase and fatty acid synthase gene activations. *Aids.* 16:1587-94.

(177) Moll, U. M., S. Wolff, D. Spidel, and W. Deppert. 2005. Transcription-independent pro-apoptotic functions of p53. *Curr Opin Cell Biol.* 17-631-6.

(178) Mondy, K., W. G. Powderly, S. A. Claxton, K. H. Yarasheski, M. Royal, J. S. Stoneman, M. E. Hoffmann, and P. Tebas. 2005. Alendronate, vitamin D, and calcium for the treatment of osteopenia/osteoporosis associated with HIV infection. *J Acquir Immune Defic Syndr.* 38:426-31.

(179) Mondy, K., and P. Tebas. 2007. Cardiovascular risks of antiretroviral therapies. *Annu Rev Med.* 58:141-55.

(180) Moyle, G. 2007. Metabolic issues associated with protease inhibitors. *J Acquir Immune Defic Syndr.* 45 Suppl 1:S19-26.

(181) Mujawar, Z., H. Rose, M. P. Morrow, T. Pushkarsky, L. Dubrovsky, N. Mukhamedova, Y. Fu, A. Dart, J. M. Orenstein, Y. V. Bobryshev, M. Bukrinsky, and D. Sviridov. 2006. Human immunodeficiency virus impairs reverse cholesterol transport from macrophages. *PLoS Biol.* 4:e365.

(182) Mukhopadhyay, A., B. Wei, S. J. Zullo, L V. Wood, and H. Weiner. 2002. In vitro evidence of inhibition of mitochondrial protease processing by HIV-1 protease inhibitors in yeast: a possible contribution to lipodystrophy syndrome. *Mitochondrion.* 1:511-8.

(183) Muntoni, F., M. Brokington, S. Torelli, and S. C. Brown. 2004. Defective glycosylation in congenital muscular dystrophies. *Curr Opin Neurol.* 17:205-9.

(184) Mylonis, I., V. Drosou, S. Brancorsini, E. Nikolakaki, P. Sassone-Corsi, and T. Giannakouros. 2004. Temporal association of protamine 1 with the inner nuclear membrane protein lamin B receptor during spermiogenesis. *J Biol Chem.* 279:11626-31.

(185) Naujokat, C., D. Fuchs, and C. Berges. 2007. Adaptive modification and flexibility of the proteasome system in response to proteasome inhibition. *Biochim Biophys Acta.* 1773:1389-97.

(186) Navarro, C. L., J. Cadinanos, A. De Sandra-Govannoli, R. Bernard, S. Courrier, I. Boccaccio, A. Boyer, W. J. Kleijer, A. Wagner, F. Giuliano, F. A. Beemer, J. M. Freije, P. Cau, R. C. Hennekam, C. Lopez-Otin, C. Badens, and N. Levy. 2005. Loss of ZMPSTE24 (FACE-1) causes autosomal recessive restrictive dermopathy and accumulation of Lamin A precursors. *Hum Mol Genet.* 14:1503-13.

(187) Navarro, C. L., P. Cau, and N. Levy. 2006. Molecular bases of progeroid syndromes. *Hum Mol Genet.* 15 Suppl 2:R151-61.

(188) Navarro, C. L, A. De Sandre-Giovannoli, R. Bernard, I. Boccaccio, A. Boyer, D. Genevieve, S. Hadj-Rabia, C. Gaudy-Marqueste, H. S. Smitt, P. Vabres, L Faivre, A. Verloes, T. Van Essen, E. Flori, R. Hennekam, F. A. Beemer, N. Laurent, M. Le Merrer, P. Cau, and N. Levy. 2004. Lamin A and ZMPSTE24 (FACE-1) defects cause nuclear disorganization and identify restrictive dermopathy as a lethal neonatal laminopathy. *Hum Mol Genet.* 13:2493-503.

(189) Negredo, E., J. Molto. J. Puig, D. Cinquegrana, A. Bonjoch, N. Perez-Alvarez, R. Lopez-Blazquez, A. Blanco, B. Clotet, and C. Rey-Joly. 2006. Ezetimibe, a promising lipid-lowering agent for the treatment of dyslipidaemia in HIV-infected patients with poor response to statins. *Aids.* 20:2159-64.

(190) Nemoto, S., C. A. Combs, S. French, B. H. Ahn, M. M. Fergusson, R. S. Balaban, and T. Finkel. 2006. The mammalian longevity-associated gene product p66shc regulates mitochondrial metabolism. *J Bol Chem.* 281:10555-60.

(191) Neye, Y., M. Dufer, G. Drews, and P. Krippet-Drews. 2006. HIV protease inhibitors: suppression of insulin secretion by inhibition of voltage-dependent K+ currents and anion currents. *J Pharmacol Exp Ther.* 316:106-12.

(192) Nguyen. A. T., A. Gagnon, J. B. Angel, and A. Sorisky. 2000. Ritonavir increases the level of active ADD-1/SREBP-1 protein during adipogenesis. *Aids* 14:2487-73.

(193) Nisoli, E., and M. O. Carruba. 2006. Nitric oxide and mitochondrial biogenesis. *J Cell Sci.* 119:2855-682.

(194) Nisoli, E., C. Tonello, A. Cardile, V. Cozzi, R. Bracale, L. Tedesco, S. Falcone, A. Valerklo, O. Cantoni, E. Clementi, S. Moncada, and M. O. Carruba. 2005. Calorie restriction promotes mitochondrial biogenesis by inducing the expression of eNOS. *Science.* 310:314-7.

(195) Njajou, O. T., R. M. Cawthon, C. M. Demcott, S. H. Wu, S. Ott, M. J. Garant, E. H. Blackburn, B. D. Mitchell, A. R. Shuldiner, and W. C. Hsueh. 2007. Telomere length is paternally inherited and is associated with parental lifespan. *Proc Natl Acad Sci USA.* 104:12135-9.

(196) North, B. J., and E. Verdin. 2004. Sirtuins: Sir2-related NAD-dependent protein deacetylases. *Genome Biol.* 5:224.

(197) Novelli, G., A. Muchir, F. Sangiuolo, A. Helbling-Leclerc, M. R. D'Apice, C. Massart, F. Capon, P. Sbraccia, M. Federici, R. Lauro, C. Tudisco, R. Pallotta, G. Scarano, B. Dallapiccola, L. Merlini, and G. Bonne. 2002. Mandibuloacral dysplasia is caused by a mutation in LMNA-encoding lamin A/C. *Am J Hum Genet.* 71:426-31.

(198) Oberdoerffer, P., and D. A. Sinclair. 2007. The role of nuclear architecture in genomic instability and ageing. *Nat Rev Mod Cell Biol.* 8692-702.

(199) Olivero, O. A. 2007. Mechanisms of genotoxicity of nucleoside reverse transcriptase inhibitors. *Environ Mol Mutagen.* 48:215-23.

(200) Olivero, O. A., G. M. Shearer, C. A. Chougnet, A. A. Kovacs, A. L. Landay, R. Baker, A. M. Stek, M. M. Khoury, L. A. Proia, H. A Kessler, B. E. Sha, R. E. Tarone, and M. C. Poirier. 1999. Incorporation of zidovudine into leukocyte DNA from HIV-1-positive adults and pregnant women, and cord blood from infants exposed in utero. *Aids.* 13.919-25.
(201) Olivero, O. A., A. M. Tejera, J. J. Fernandez, B. J. Taylor, S. Das. R. L. Divi, and M. C. Poirier. 2005. Zidovudine induces S-phase arrest and cell cycle gene expression changes in human cells. *Mutagenesis.* 20:13946.
(202) Orsini, F., E. Migliaccio, M. Moroni, C. Contursi, V. A. Raker, D. Piccini, I. Martin-Padura, G. Pelliccia, M. Trinei, M. Bono, C. Puri, C. Tacchetti, M. Ferrini, R. Mannucci, I. Nicoletti, L. Lanfrancone, M. Giorgio, and P. G. Pelicci. 2004. The life span determinant p66Shc localizes to mitochondria where it associates with mitochondrial heat shock protein 70 and regulates trans-membrane potential. *J Biol Chem.* 279:25689-95.
(203) Pacenti, M., L. Barzon, F. Favaretto, K. Fincati, S. Romano, G. Milan, R. Vettor, and G. Palu. 2006. Microarray analysis during adipogenesis identifies new genes altered by antiretroviral drugs. *Aids.* 20:1691-705.
(204) Palmieri, F. 2004. The mitochondrial transporter family (SLC25): physiological and pathological implications. *Pflugers Arch.* 447:689-709.
(205) Pan, Y., A. Garg, and A. K. Agarwal. 2007. Mislocalization of prelamin A Tyr646Phe mutant to the nuclear pore complex in human embryonic kidney 293 cells. *Biochem Biophys Res Commun.* 355:78-84.
(206) Pandita, T. K., C. R. Hunt, G. G. Sharma, and Q. Yang. 2007. Regulation of telomere movement by telomere chromatin structure. *Cell Mol Life Sci.* 64:131-8.
(207) Papazoglu. C., and A. A. Mills. 2007. p53: at the crossroad between cancer and ageing. *J Pathol.* 211:124-33.
(208) Parker, R. A., O. P. Flint, R. Mulvey, C. Elosua, F. Wang, W. Fenderson, S. Wang, W. P. Yang, and M. A. Noor. 2005. Endoplasmic reticulum stress links dyslipidemia to inhibition of proteasome activity and glucose transport by HIV protease inhibitors. *Mol Pharmacol.* 67:1909-19.
(209) Pennings, M., I. Meurs, D. Ye, R. Out, M. Hoekstra, T. J. Van Berkel, and M. Van Eck. 2006. Regulation of cholesterol homeostasis in macrophages and consequences for atheroscerotic lesion development. *FEBS Lett.* 580:5588-96.
(210) Percival, J. M., and S. C. Froehner. 2007. Golgi complex organization in skeletal muscle: a role for Golgi-mediated glycosylation in muscular dystrophies? *Traffic.* 8:184-94.
(211) Petersen-Mahrt. S. K., C. Estmer, C. Ohrmalm, D. A. Matthews, W. C. Russell, and G. Akusjarvi. 1999. The splicing factor-associated protein, p32, regulates RNA splicing by inhibiting ASF/SF2 RNA binding and phosphorylation. *Embo J.* 18:1014-24.
(212) Piccinini, M., M. T. Rinaudo, A. Anselmino, B. Buccinna, C. Ramondetti, A. Dematteis, E. Ricotti, L. Palmisano, M. Mostert, and P. A. Tovo. 2005. The HIV protease inhibitors nelfinavir and saquinavir, but not a variety of HIV reverse transcriptase inhibitors, adversely affect human proteasome function. *Antivir Ther.* 10:215-23.
(213) Pilon, A. A., J. J. Lum, J. Sanchez-Dardon, B. N. Phenix, R. Douglas, and A. D. Badley. 2002. Induction of apoptosis by a nonnucleoside human immunodeficiency virus type 1 reverse transcriptase inhibitor. *Antimicrob Agents Chemother.* 46:2687-91.
(214) Porcu, M., and A. Chiarugi. 2005. The emerging therapeutic potential of sirtuin-interacting drugs: from cell death to lifespan extension. *Trends Pharmacol Sci.* 26:94-103.
(215) Quarrie, J. K., and K. T. Riabowol. 2004. Murine models of life span extension. *Sci Aging Knowledge Environ.* 2004:re5.
(216) Razzaque, M. S., and B. Lanske. 2006. Hypervitaminosis D and premature aging: lessons learned from Fgt23 and Klotho mutant mice. *Trends Mol Med.* 12:298-305.
(217) Restrepo. C. S., L. Diethelm, J. A. Lemos, E. Velasquez, T. A. Ovella, S. Martinez, J. Carrillo, and D. F. Lemos. 2006. Cardiovascular complications of human immunodeficiency virus infection. *Radiographics.* 26:213-31.
(218) Restrepo, C. S., D. F. Lemos, H. Gordillo, R. Odero, T. Varghese, W. Tiemann, F. F. Rivas, R. Moncada, and C. R. Gimenez. 2004. Imaging findings in musculoskeletal complications of AIDS. *Radiographics.* 24:1029-49.
(219) Richard, I., O. Broux, V. Allamand, F. Fougerousse, N. Chiannilkulchai, N. Bourg, L. Brenguier, C. Devaud, P. Pasturaud, C. Roudaut, and et al. 1995. Mutations in the proteolytic enzyme calpain 3 cause limb-girdle muscular dystrophy type 2A. *Cell.* 81:27-40.
(220) Richter, C., J. W. Park, and B. N. Ames. 1988. Normal oxidative damage to mitochondrial and nuclear DNA is extensive. *Proc Natl Acad Sci USA.* 85:6465-7.
(221) Riddle, T. M., D. G. Kuhel, L. A. Woollett, C. J. Fichtenbaum, and D. Y. Hui. 2001. HIV protease inhibitor induces fatty acid and sterol biosynthesis in liver and adipose tissues due to the accumulation of activated sterol regulatory element-binding proteins in the nucleus. *J Biol Chem.* 276:37514-9.
(222) Roche, R., I. Poizot-Martin, C. M. Yazidi, E. Compe, J. A. Gastaut, J. Torresani, and R. Planells. 2002. Effects of antiretroviral drug combinations on the differentiation of adipocytes. *Aids.* 16:13-20.
(223) Roehl White, S., and B. Lauring. 2007. AAA+ ATPases: Achieving Diversity of Function with Conserved Machinery. *Traffic.*
(224) Rota, M., N. LeCapitaine, T. Hosoda, A Boni, A. De Angelis, M. E. Padin-Iruegas, G. Esposito, S. Vitale, K. Urbanek, C. Casarsa, M. Giorgio, T. F. Luscher, P. G. Pelicci, P. Anversa, A. Led, and J. Kajstura. 2006. Diabetes promotes cardiac stem cell aging and heart failure, which are prevented by deletion of the p66shc gene. *Circ Res.* 99:42-52.
(225) Rudich, A, R. Ben-Romano, S. Etzion, and N. Bashan. 2005. Cellular mechanisms of insulin resistance, lipodystrophy and atherosclerosis induced by HIV protease inhibitors. *Acta Physiol Scand.* 183:75-88.
(226) Russell, S. J., and C. R. Kahn. 2007. Endocrine regulation of ageing. *Nat Rev Mol Cell Biol.* 8:681-91.
(227) Sablina, A. A., A. V. Budanov, G. V. Ilyinskaya, L. S. Agapova, J. E. Kravchenko, and P. M. Chumakov. 2005. The antioxidant function of the p53 tumor suppressor. *Nat Med.* 11:1308-13.
(228) Saint-Marc, T., M. Partisani, I. Poizot-Martin, F. Bruno, O. Rouviere, J. M. Lang, J. A. Gastaut, and J. L. Touraine. 1999. A syndrome of peripheral fat wasting (lipodystrophy) in patients receiving long-term nucleoside analogue therapy. *Aids.* 13:1659-67.
(229) Saint-Marc, T., M. Partisani, I. Poizot-Martin, O. Rouviere, F. Bruno, R. Avellaneda, J. M. Lang, J. A Gastaut, and J. L. Touraine. 2000. Fat distribution evaluated by computed tomography and metabolic abnormalities in patients undergoing antiretroviral therapy: preliminary results of the LIPOCO study. *Aids.* 14:3749.
(230) Scaffidi, P., and T. Misteli. 2006. Lamin A-dependent nuclear defects in human aging. *Science.* 312:1059-63.
(231) Schmid, G., M. P. Kramer, M. Maurer, S. Wandl, and J. Wesieraka-Gadek. 2007. Cellular and organismal ageing: Role of the p53 tumor suppressor protein in the induction of transient and terminal senescence. *J Cell Biochem* 101:1355-69.
(232) Schriner, S. E., N. J. Linford, G. M. Martin, P. Treuting, C. E. Ogburn, M. Emond, P. E. Coskun, W. Ladiges, N. Wolf, H. Van Remmen, D. C. Wallace, and P. S. Rabinovitch. 2005. Extension of murine life span by overexpression of catalase targeted to mitochondria. *Science.* 308:1909-11.
(233) Schutt, M., J. Zhou, M. Meier, and H. H. Klein. 2004. Long-term effects of HIV-1 protease inhibitors on insulin secretion and insulin signaling in INS-1 beta cells. *J Endocrinol.* 183:445-54.
(234) Seidah, N. G., A. M. Khatib, and A. Prat. 2006. The proprotein convertases and their implication in sterol and/or lipid metabolism. *Biol Chem.* 387:871-7.
(235) Sengupta, S., and C. C. Harris. 2005. p53: traffic cop at the crossroads of DNA repair and recombination. *Nat Rev Mol Cell Biol.* 6:44-55.
(236) Shaldai, S., N. Amariglio, G. Rechavi, and A. J. Simon. 2007. Gene silencing at the nuclear periphery. *Febs J.* 274:1383-92.
(237) Sharma, A., S. Awasthi, C. K. Harrod. E. F. Matlock, S. Khan, L. Xu, S. Chan, H. Yang, C. K. Thammavaram, R. A. Rasor, D. K. Burns, D. J. Skiest, C. Van Lint, A. M. Girard, M. McGee, R. J. Monnat, Jr., and R. Harrod. 2007. The Werner syndrome helicase is a cofactor for HIV-1 long terminal repeat transactivation and retroviral replication. *J Biol Chem.* 282:12048-57.
(238) Sharpless, N. E. and R. A. DePinho. 2002. p53: good cop/bad cop. *Cell.* 110:9-12.
(239) Short, K. R., M. L. Bigelow, J. Kahl, R. Singh, J. Coenen-Schimke, S. Raghavakaimal, and K. S. Nair. 2005. Decline in skeletal muscle mitochondrial function with aging in humans. *Proc Natl Acad Sci USA.* 102:5618-23.
(240) Simos, G., and S. D. Georgatos. 1994. The lamin B receptor-associated protein p34 shares sequence homology and antigenic determinants with the splicing factor 2-associated protein p32. *FEBS Lett.* 346:225-8.
(241) Sirkis, R., J. E. Gerst, and D. Fass. 2006. Ddi1, a eukaryotic protein with the retroviral protease fold. *J Mol Biol.* 364:376-87.
(242) Sommers, J. A, S. Sharma, K. M. Doherty, P. Karmakar, Q. Yang, M. K. Kenny, C. C. Harris, and R. M. Brosh, Jr. 2005. p53 modulates RPA-dependent and RPA-independent WRN helicase activity. *Cancer Res.* 65:1223-33.
(243) Stewart, S. A., and R. A. Weinberg. 2006. Telomeres: cancer to human aging. *Annu Rev Cell Dev Biol.* 22:531-57.
(244) Storz, P. 2006. Reactive oxygen species-mediated mitochondria-to-nucleus signaling: a key to aging and radical-caused diseases. *Sci STKE.* 2006:re3.
(245) Suzuki, Y., and R. Craigie. 2007. The road to chromatin—nuclear entry of retroviruses. *Nat Rev Microbiol.* 5:187-96.
(246) Tehranzadeh, J., R. R. Ter-Oganesyan, and L. S. Steinbach. 2004a. Musculoskeletal disorders associated with HIV infection and AIDS. Part I: infectious musculoskeletal conditions. *Skeletal Radiol.* 33:249-59.
(247) Tehranzadeh, J., R. R. Ter-Oganesyan, and L. S. Steinbach. 2004b. Musculoskeletal disorders associated with HIV infection and AIDS. Part II: non-infectious musculoskeletal conditions. *Skeletal Radiol.* 33:311-20.
(248) Thomas, C. M., and E. J. Smart. 2007. How HIV protease inhibitors promote atherosclerotic lesion formation. *Curr Opin Lipidol.* 18:561-5.
(249) Thomas, J., and S. M. Doherty. 2003. HIV infection—a risk factor for osteoporosis. *J Acquir Immune Defic Syndr.* 33 281-91.
(250) Torres, H. A., B. J. Barnett, and R. C. Arduino. 2007. Alopecia associated with ritonavir-boosted atazanavir therapy. *Aids.* 21:1391-2.
(251) Trifunovic, A., A. Hansson, A. Wredenberg, A. T. Rovio, E. Dufour, I. Khvorostov, J. N. Spelbrink, R. Wibom, H. T. Jacobs, and N. G. Larsson. 2005. Somatic mtDNA mutations cause aging phenotypes without affecting reactive oxygen species production. *Proc Natl Acad Sci USA.* 102:17993-8.
(252) Trifunovic, A., A. Wredenberg, M. Falkenberg, J. N. Spelbrink, A. T. Rovio, C. E. Bruder, Y. M. Bohlooly, S. Gidlof, A Oldfors, R. Wibom, J. Tornell, H. T. Jacobs, and N. G. Larsson. 2004. Premature ageing in mice expressing defective mitochondrial DNA polymerase. *Nature.* 429:417-23.
(253) Trinei, M., M. Giorgio, A. Cicalese, S. Barozzi, A. Ventura, E. Migliaccio, E. Milia, I. M. Padura, V. A. Raker, M. Maccarana, V. Petronili, S. Minucci, P. Bernardi, L. Lanfrancone, and P. G. Pelicci. 2002. A p53-p66Shc signalling pathway controls intracellular redox status, levels of oxidation-damaged DNA and oxidative stress-induced apoptosis. *Oncogene.* 21:3872-8.
(254) Truscott, K. N., K. Brandner, and N. Pfanner. 2003. Mechanisms of protein import into mitochondria. *Curr Biol.* 13:R326-37.
(255) Tyner, S. D., S. Venkatachalam, J. Choi, S. Jones, N. Ghebranious, H. Igelmann, X. Lu, G. Soron, B. Cooper, C. Brayton, S. Hee Park, T. Thompson, G. Karsenty, A. Bradley, and L. A. Donehower. 2002. p53 mutant mice that display early ageing-associated phenotypes. *Nature.* 415:45-53.
(256) Unger, R. H. 2006. Klotho-induced insulin resistance: a blessing in disguise? *Nat Med.* 12:56-7.
(257) van Wijk, J. P., E. J. de Koning, M. C. Cabezas, J. Joven, J. op't Roodt, T. J. Rabelink, and A. M. Hoepelman. 2006. Functional and structural markers of atherosclerosis in human immunodeficiency virus-infected patients. *J Am Coll Cardiol.* 47:1117-23.
(258) Varela, I., J. Cadinanos, A. M. Pendas, A. Gutierrez-Fernandez, A. R. Folgueras, L. M. Sanchez, Z. Zhou, F. J. Rodriguez, C. L. Stewart, J. A. Vega, K. Tryggvason, J. M. Freije, and C. Lopez-Otin, 2005. Accelerated ageing in mice deficient in Zmpste24 protease is linked to p53 signalling activation. *Nature.* 437:564-8.
(259) Vidal, F., J. C. Domingo, J. Guallar, M. Saumoy, B. Cordobilla, R. Sanchez de la Rosa, M. Giralt, M. L. Alvarez, M. Lopez-Dupla, F. Torres, F. Villarroya, T. Cihlar, and P. Domingo. 2006. In vitro cytotoxicity and mitochondrial toxicity of tenofovir alone and in combination with other antiretrovirals in human renal proximal tubule cells. *Antimicrob Agents Chemother.* 50:3824-32.
(20) Vijg. J., and Y. Suh. 2006. Ageing: chromatin unbound. *Nature.* 440:874-5.
(261) Vicek, S., T. Dechat, and R. Foisner. 2001. Nuclear envelope and nuclear matrix interactions and dynamics. *Cell Mol Life Sci.* 58:1758-65.

(262) Vicek, S., and R. Foisner. 2006. A-type lamin networks in light of laminopathic diseases. *Biochim Biophys Acta.*
(263) Vicek. S., and R. Foisner. 2007a. Lamins and lamin-associated proteins in aging and disease. *Curr Opin Cell Biol.* 19:298-304.
(264) Vicek, S., and R. Foisner. 2007b. A-type lamin networks in light of laminopathic diseases. *Biochim Biophys Acta.* 1773:661-74.
(265) Wallace, D. C. 2005. A mitochondrial paradigm of metabolic and degenerative diseases, aging, and cancer: a dawn for evolutionary medicine. *Annu Rev Genet.* 39:359-407.
(266) Wallis, C. V., A. N. Sheerin, M. H. Green, C. J. Jones, D. Kipling, and R. G. Faragher. 2004. Fibroblast clones from patients with Hutchinson-Gilford progeria can senesce despite the presence of telomerase. *Exp Gerontol.* 39:461-7.
(267) Wang. X., H. Mu, H. Chai, D. Liao, Q. Yao, and C. Chen. 2007. Human immunodeficiency virus protease inhibitor ritonavir inhibits cholesterol efflux from human macrophage-derived foam cells. *Am J Pathol.* 171:304-14.
(268) Wang, X., and D. J. Rader. 2007. Molecular regulation of macrophage reverse cholesterol transport. *Curr Opin Cardiol.* 22:388-72.
(269) Williams, K., Y. P. Rao, R. Natarajan, W. M. Pandak, and P. B. Hylemon. 2004. Indinavir alters sterol and fatty acid homeostatic mechanisms in primary rat hepatocytes by increasing levels of activated sterol regulatory element-binding proteins and decreasing cholesterol 7alpha-hydroxylase mRNA levels. *Biochem Pharmacol.* 67:255-67.
(270) Wiwanitkit, V. 2004. Prevalence of dermatological disorder in Thai HIV-infected patients correlated with different CD4 lymphocyte count statuses: a note on 120 cases. *Int J Dermatol.* 43:265-8.
(271) Worman, H. J., and G. Bonne. 2007. "Laminopathies": a wide spectrum of human diseases. *Exp Cell Res.* 313: 2121-33.
(272) Wright, L. P., and M. R. Philips. 2006. Thematic review series: lipid posttranslational modifications. CAAX modification and membrane targeting of Ras. *J Lipid Res.* 47:883-91.
(273) Wynford-Thomas, D. 1996. Telomeres, p53 and cellular senescence. *Oncol Res.* 8:387-98.
(274) Yamagishi. S., T. Matsui, T. Sato, and M. Takeuchi. 2006. Protective role of pravastatin in the pathogenesis of the metabolic syndrome. *Med Hypotheses.* 66:609-11.
(275) Yamaguchi, T., Y. Takayama. M. Saito, F. Ishikawa, and M. Saneyoshi. 2001. Telomerase-inhibitory effects of the triphosphate derivatives of some biologically active nucleosides. *Nucleic Acids Res Suppl:* 211-2.
(276) Yamanaka, H., H. Gatanaga, P. Kosalaraksa, S. Matsuoka-Aizawa, T. Takahashi, S. Kimura, and S. Oka. 2007. Novel mutation of human DNA polymerase gamma associated with mitochondrial toxicity induced by anti-HIV treatment. *J Infect Dis.* 195:1419-25.
(277) Yeh, R. F., V. E. Gaver, K. B. Patterson, N. L. Rezk, F. Baxter-Meheux, M. J. Blake, J. J. Eron, Jr., C. E. Klein, J. C. Rublein, and A. D. Kashuba. 2006. Lopinavir/ritonavir Induces the hepatic activity of cytochrome P450 enzymes CYP2C9, CYP2C19, and CYP1A2 but inhibits the hepatic and intestinal activity of CYP3A as measured by a phenotyping drug cocktail in healthy volunteers. *J Acquir Immune Defic Syndr.* 42:52-60.
(278) Yousefi, S., R. Perozzo, I. Schmid, A. Ziemiecki, T. Schaffner, L. Scapozza, T. Brunner, and H. U. Simon. 2006. Calpain-mediated cleavage of Atg5 switches autophagy to apoptosis. *Nat Cell Biol.* 8:1124-32.
(279) Zafon, C. 2007. Jekyll and Hyde, the p53 protein, pleiotropics antagonisms and the thrifty aged hypothesis of senescence. *Med Hypotheses.* 68:1371-7.
(280) Zhang, D., T. J. Chando, D. W. Everett, C. J. Patten, S. S. Dehal, and W. G. Humphreys. 2005. In vitro inhibition of UDP glucuronosyltranferases by atazanavir and other HIV protease inhibitors and the relationship of this property to in vivo bilirubin glucuronidation. *Drug Metab Dispos.* 33:1729-39.
(281) Zhong, D. S., X. H. Lu, B. S. Conklin, P. H. Lin, A. B. Lumsden, Q. Yao, and C. Chen. 2002. HIV protease inhibitor ritonavir induces cytotoxicity of human endothelial cells. *Arterioscler Thromb Vasc Biol.* 22:1560-6.
(282) Zhou, H., E. C. Gurley, S. Jarujaron, H. Ding, Y. Fang, Z. Xu, W. M. Pandak, Jr., and P. B. Hylemon. 2006. HIV protease inhibitors activate the unfolded protein response and disrupt lipid metabolism in primary hepatocytes. *Am J Physiol Gastrointest Liver Physiol.* 291:G1071-80.
(283) Zhou, H., W. M. Pandak, Jr., V. Lyall, R. Natarajan, and P. B. Hylemon. 2005. HIV protease inhibitors activate the unfolded protein response in macrophages: implication for atherosclerosis and cardiovascular disease. *Mol Pharmacol.* 68:690-700.
(284) Blobel et Potter, V. R. Nuclei from rat liver: isolation method that combines purity with high yield, Science 154, 1662-1665, 1966
(285) Sullivan, T. Escalante-Alcalde, D. Bhatt, H. Anver, M. Bhat, N. Nagashima, K. Stewart, C. L. Burke, B. *Loss of A-type lamin expression compromises nuclear envelope integrity leading to muscular dystrophy.* J. Cell Biol. 147: 913-920, 1999

The invention claimed is:
1. A pharmaceutical composition, comprising:
a synergistically effective amount of the combination of at least one hydroxymethylglutaryl-coenzyme A (HMG-CoA) reductase inhibitor or one of its physiologically acceptable salts, which is selected from the group consisting of pravastatin, atorvastatin, simvastatin, rivastatin, mevastatin, velostatin, fluvastatin, cerivastatin, rosuvastatin, pitavastatin, lovastatin, and a pharmaceutically acceptable salt thereof; and
at least one farnesyl-pyrophosphate synthase inhibitor or one of its physiologically acceptable salts, wherein the farnesyl-pyrophosphate synthase inhibitor is selected from the group consisting of a molecule of the amino-biphosphonate (NBP) family or one of its physiologically acceptable salts which is an aminobisphosphonate selected from the group consisting of alendronic acid or its ionic form, alendronate; ibandronic acid or its ionic form, ibandronate; neridronic acid or its ionic form, neridronate; olpadronic acid or its ionic form, olpadronate; pamidronic acid or its ionic form, pamidronate; risedronic acid or its ionic form, risedronate; zoledronic acid or its ionic form, zoledronate; 4-N,N-dimethylaminomethane diphosphonic acid or its ionic form, dimethylaminomethanediphosphonate; α-amino-(4 hydroxybenzylidene) diphosphonate; and a pharmaceutically acceptable salt thereof,
wherein the pharmaceutical composition further comprises at least one anti-HIV agent, and wherein the anti-HIV agent is a protease inhibitor or a reverse transcriptase inhibitor.

2. The pharmaceutical composition according to claim 1, in which the HMG-CoA reductase inhibitor is pravastatin and in which the farnesyl-pyrophosphate synthase inhibitor is zoledronic acid or its ionic form, zoledronate or is alendronic acid or its ionic form, alendronate.

3. The pharmaceutical composition according to claim 1, in which the anti-HIV agent is a protease inhibitor selected from the group consisting of fosamprenavir, lopinavir, ritonavir, amprenavir, atazanavir and indinavir.

4. A process for treating an HIV-infected patient comprising the administration of a pharmaceutical composition according to claim 1.

5. The process according to claim 4, in which the administration is performed orally or by injection.

6. A process for treating premature aging caused in a patient as a side effect of anti-HIV treatment, wherein the patient is administered an anti-HIV agent selected from the group consisting of protease inhibitors and reverse transcriptase inhibitors, which process comprises:
the administration of a synergistically effective amount of the combination of at least one hydroxymethylglutaryl-coenzyme A (HMG-CoA) reductase inhibitor or one of its physiologically acceptable salts, which is selected from the group consisting of pravastatin, atorvastatin, simvastatin, rivastatin, mevastatin, velostatin, fluvastatin, cerivastatin, rosuvastatin, pitavastatin, lovastatin, and a pharmaceutically acceptable salt thereof; and
at least one farnesyl-pyrophosphate synthase inhibitor or one of its physiologically acceptable salts which is an aminobisphosphonate selected from the group consisting of alendronic acid or its ionic form, alendronate; ibandronic acid or its ionic form, ibandronate; neridronic acid or its ionic form, neridronate; olpadronic acid or its ionic form, olpadronate; pamidronic acid or its ionic form, pamidronate; risedronic acid or its ionic form, risedronate; zoledronic acid or its ionic form, zoledronate; 4-N,N-dimethylaminomethane diphosphonic acid or its ionic form, dimethylaminomethanediphosphonate; α-amino-(4 hydroxybenzylidene) diphosphonate; and a pharmaceutically acceptable salt thereof.

7. The process according to claim 6, in which the HMG-CoA reductase inhibitor is pravastatin and the farnesyl-pyrophosphate synthase inhibitor is zoledronic acid or its ionic form, zoledronate or alendronic acid or its ionic form, alendronate.

8. The process according to claim 6, in which the administration is performed with a dose of the hydroxymethylglutaryl-coenzyme A (HMG-CoA) reductase inhibitor of 0.01 to 2 mg/kg of body weight and with a dose of the farnesyl-pyrophosphate synthase inhibitor or 0.01 to 40 mg/kg of body weight.

9. The process according to claim 6, in which the administration is performed orally or by injection.

10. A process for treating an HIV-infected patient comprising, in any order, the following steps:
i. administration of a synergistically effective amount of a mixture comprising at least one hydroxymethylglutaryl-coenzyme A (HMG-CoA) reductase inhibitor and at least one farnesyl-pyrophosphate synthase inhibitor, wherein the at least one HMG-CoA reductase inhibitor or one of its physiologically acceptable salts, is selected from the group consisting of pravastatin, atorvastatin, simvastatin, rivastatin, mevastatin, velostatin, fluvastatin, cerivastatin, rosuvastatin, pitavastatin, lovastatin, and a pharmaceutically acceptable salt thereof and wherein the at least one farnesyl-pyrophosphate synthase inhibitor or one of its physiologically acceptable salts is an aminobisphosphonate selected from the group consisting of alendronic acid or its ionic form, alendronate; ibandronic acid or its ionic form, ibandronate; neridronic acid or its ionic form, neridronate; olpadronic acid or its ionic form, olpadronate; pamidronic acid or its ionic form, pamidronate; risedronic acid or its ionic form, risedronate; zoledronic acid or its ionic form, zoledronate; 4-N,N-dimethylaminomethane diphosphonic acid or its ionic form, dimethylaminomethanediphosphonate; α-amino-(4 hydroxybenzylidene) diphosphonate; and a pharmaceutically acceptable salt thereof; and
ii. administration of an anti-HIV agent,
wherein the administrations are concomitant, successive, or alternative, and wherein the anti-HIV agent is a protease inhibitor or a reverse transcriptase inhibitor.

11. The process according to claim 10, in which said mixture and said anti-HIV agent are co-administered.

12. The process according to claim 10, in which the anti-HIV agent is a protease inhibitor selected from the group consisting of fosamprenavir, lopinavir, ritonavir, amprenavir, atazanavir and indinavir.

13. The process according to claim 10, in which at least one of the administrations is performed orally or by injection.

14. The process according to claim 10, in which the administration is performed with a dose of the hydroxymethulglutaryl-coenzyme A (HMG-CoA) reductase inhibitor of 0.01 to 2 mg/kg of body weight and with a dose of the farnesyl-pyrophosphate synthase inhibitor of 0.01 to 40 mg/kg of body weight.

15. The process according to claim 10, wherein the HMG-CoA reductase inhibitor is pravastatin and wherein the farnesyl-pyrophosphate synthase inhibitor is zolendronic acid or its ionic form, zoledronate or is alendronic acid or its ionic form, alendronate.

* * * * *